(12) United States Patent
Lim et al.

(10) Patent No.: US 11,952,433 B2
(45) Date of Patent: Apr. 9, 2024

(54) HETEROCHIRAL PEPTIDE-COMPLEX AND COMPOSITION FOR MEASURING NUCLEAR MAGNETIC RESONANCE SPECTROSCOPY RESIDUAL DIPOLAR COUPLING CONTAINING SELF-ASSEMBLED INTERMEDIATES OF HETEROCHIRAL PEPTIDE-COMPLEX

(71) Applicant: INDUSTRY-ACADEMIC COOPERATION FOUNDATION, YONSEI UNIVERSITY, Seoul (KR)

(72) Inventors: Yong-Beom Lim, Seoul (KR); Hye Soo Lee, Seoul (KR)

(73) Assignee: INDUSTRY ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 110 days.

(21) Appl. No.: 17/153,423

(22) Filed: Jan. 20, 2021

(65) Prior Publication Data
US 2021/0221844 A1   Jul. 22, 2021

(30) Foreign Application Priority Data

Jan. 22, 2020   (KR) .................. 10-2020-0008499
Jan. 15, 2021   (KR) .................. 10-2021-0005720

(51) Int. Cl.
| | |
|---|---|
| *C07K 7/06* | (2006.01) |
| *A61K 49/08* | (2006.01) |
| *A61K 49/14* | (2006.01) |
| *G01N 24/08* | (2006.01) |

(52) U.S. Cl.
CPC .............. *C07K 7/06* (2013.01); *A61K 49/085* (2013.01); *A61K 49/146* (2013.01); *G01N 24/087* (2013.01)

(58) Field of Classification Search
None
See application file for complete search history.

(56) References Cited

PUBLICATIONS

Lei et al. ('A self-assembled oligopeptide as a versatile NMR alignment medium for the measurement of residual dipolar couplings in methanol' Angew Chem Int Ed v56 2017 pp. 12857-12861) (Year: 2017).*
Garcia et al. ('Chirality effects on peptide self-assembly unraveled from molecules to materials' Chem Aug. 9, 2018 pp. 1862-1876) (Year: 2018).*
Williams T ('Design, synthesis and evaluation of innovative BODIPY-peptidic conjugates for Biological Application' LSU Doctoral Dissertations, 2017 pp. 1-251, total of 261 pages) (Year: 2017).*
Israelachvili, J. N., "Intermolecular and surface forces," 3rd ed.; Academic Press: Burlington, MA, 2011; p. 535-561.

* cited by examiner

*Primary Examiner* — Ronald T Niebauer
(74) *Attorney, Agent, or Firm* — DUANE MORRIS, LLC; Gregory M. Lefkowitz; Brandon A. Chan

(57) ABSTRACT

The present disclosure relates to a heterochiral peptide complex, a self-assembled intermediate thereof, an alignment medium composition used for nuclear magnetic resonance spectroscopy residual dipolar coupling (NMR-RDC) measurement, which includes the same, and a method for NMR measurement for a biomolecule. Since the heterochiral peptide complex contains a β-sheet peptide and has superior structural stability against environmental factors such as heat, acidity and ionic strength, it is applicable as an alignment medium for measuring RDC for various biomolecules.

9 Claims, 52 Drawing Sheets
Specification includes a Sequence Listing.

Slow motion self-assembly

PEG10-V-(vV)₂-NH₂

Cal. M.W. = 1024
Obs. M.W. = 1018

(PEG10)-f₃-F₃

Cal. M.W. = 1411
Obs. M.W. = 1405

PEG10-F-(fF)$_2$-NH$_2$

Cal. M.W. = 1264
Obs. M.W. = 1258

PEG10-(fF)$_2$-NH$_2$

Cal. M.W. = 1117
Obs. M.W. = 1111

HETEROCHIRAL PEPTIDE-COMPLEX AND COMPOSITION FOR MEASURING NUCLEAR MAGNETIC RESONANCE SPECTROSCOPY RESIDUAL DIPOLAR COUPLING CONTAINING SELF-ASSEMBLED INTERMEDIATES OF HETEROCHIRAL PEPTIDE-COMPLEX

SPONSORED RESEARCH

The claimed invention was made by, on behalf of, and/or in connection with research by Yonsei University, which was sponsored by the Ministry of Science and ICT(MSIT)'s National Research Foundation of Korea under reference number 2020R1A2C2007578.

TECHNICAL FIELD

The present disclosure relates to a heterochiral peptide complex, a self-assembled intermediate thereof, an alignment medium composition used for measuring nuclear magnetic resonance spectroscopy residual dipolar coupling (NMR-RDC) containing the same, and a method for NMR measurement for a biomolecule using the same.

BACKGROUND

The identity of peptides and the mechanism of their formation are very important information in the development of tailor-made materials. However, most studies are focused on the analysis of the final self-assembled morphology rather than the mechanism.

In comparison, many researches have been conducted on protein folding. However, since the protein folding occurs quickly within seconds, special techniques have been developed and used, such as dynamics and conformational studies based on nuclear magnetic resonance (NMR) spectroscopy or other special spectroscopic methods. But, it is difficult to characterize intermediates.

RDC can improve the quality of structural analysis by NMR. Specifically, when a sample is present in an aqueous environment, the measurement of dipolar coupling is difficult due to randomized molecular motion. Therefore, the direction of the dipole needs to be limited to have anisotropy in order to measure RDC. As existing alignment media, nematic liquid crystal molecules, compressed or stretched polymer gels, Pf1 filamentous phages, bicelles, etc. are known. Because the RDC alignment medium has its own specific characteristics such as the appropriate temperature and pH ranges, compatible solvents and the charge states of aligned media, there is an ongoing need to develop new alignment media applicable to various applications.

REFERENCES OF THE RELATED ART

Patent Documents (Non-patent document 1) (Reference 1) Israelachvili, J. N., Intermolecular and surface forces. 3rd ed.; Academic Press: Burlington, M A, 2011; p 535-561.

SUMMARY

The present disclosure is directed to providing a peptide complex including a hydrophilic segment composed of a heterochiral amino acid and a hydrophobic segment composed of a hydrophilic polymer.

The present disclosure is also directed to providing a self-assembled intermediate formed through self-assembly of the peptide complex.

The present disclosure is also directed to providing an alignment medium composition for measuring residual dipolar coupling (RDC), which includes the self-assembled intermediate.

The present disclosure is also directed to providing a novel use of a peptide complex or a self-assembled intermediate thereof for measurement of NMR spectra.

The inventors of the present disclosure have designed various heterochiral peptide complexes. They have identified that the self-assembly kinetics of racemic or asymmetric heterochiral peptide complexes are significantly slower than those of the corresponding homochiral peptide complexes. They have discovered that self-assembled intermediates of racemic or asymmetric heterochiral peptide complexes exhibiting strong anisotropy are prepared during self-assembly in solution and they can be used as alignment media for measurement of nuclear magnetic resonance spectroscopy residual dipolar coupling (NMR-RDC), and have completed the present disclosure.

The present disclosure provides a peptide complex including: a peptide represented by General Formula 1 or 2, which includes heterochiral amino acids; and a compound represented by Chemical Formula 1, which is bound to one end of the peptide.

$[Y1]_a\text{-}\{\text{---}[X1]_b\text{-}[Y2]_c\}_d\text{---}[X2]_e$  [General Formula 1]

$[X1]_f\text{---}\{\text{---}[Y1]_g\text{---}[X2]_h\}_i\text{---}[Y2]_j$  [General Formula 2]

In General Formulas 1 and 2,
each of X1 and X2, which are identical to or different from each other, is independently any one selected from D-Trp, D-Phe, D-Tyr, D-Val, D-Leu and D-Ile,
each of Y1 and Y2, which are identical to or different from each other, is independently any one selected from L-Trp, L-Phe, L-Tyr, L-Val, L-Leu and L-Ile, and
each of a, f, e and j is independently an integer selected from 0 to 2, each of b, c, g and h is independently an integer selected from 1 to 5, each of d and i is independently an integer selected from 1 to 10.

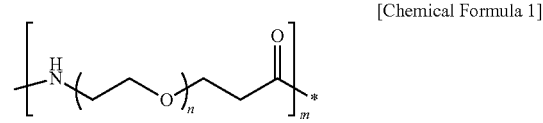

[Chemical Formula 1]

In Chemical Formula 1, each of n and m is independently an integer selected from 1 to 12.

In General Formulas 1 and 2, each of X1 and X2, which are identical to or different from each other, may be independently any one selected from D-Trp, D-Val and D-Phe, and each of Y1 and Y2, which are identical to or different from each other, may be independently any one selected from L-Trp, D-Val and L-Phe.

In General Formulas 1 and 2, X1 and X2 may be identical to each other, and Y1 and Y2 may be identical to each other.

In General Formulas 1 and 2, each of a, f, e and j may be independently an integer selected from 0 to 2, each of b, c, g and h may be independently an integer selected from 1 to 3, and each of d and i may be independently an integer selected from 1 to 4.

The peptide may be represented by SEQ ID NOS: 1 to 12.

(D)Trp-(L)Trp-(D)Trp-(L)Trp-(D)Trp-(L)Trp  [SEQ ID NO: 1]

(D)Val-(L)Val-(D)Val-(L)Val-(D)Val-(L)Val  [SEQ ID NO: 2]

(D)Phe-(L)Phe-(D)Phe-(L)Phe-(D)Phe-(L)Phe  [SEQ ID NO: 3]

(L)Trp-(D)Trp-(L)Trp-(D)Trp-(L)Trp-(D)Trp  [SEQ ID NO: 4]

(L)Val-(D)Val-(L)Val-(D)Val-(L)Val-(D)Val  [SEQ ID NO: 5]

(L)Phe-(D)Phe-(L)Phe-(D)Phe-(L)Phe-(D)Phe  [SEQ ID NO: 6]

(L)Trp-(D)Trp-(L)Trp-(D)Trp-(L)Trp  [SEQ ID NO: 7]

(L)Val-(D)Val-(L)Val-(D)Val-(L)Val  [SEQ ID NO: 8]

(L)Phe-(D)Phe-(L)Phe-(D)Phe-(L)Phe  [SEQ ID NO: 9]

(D)Trp-(L)Trp-(D)Trp-(L)Trp-(D)Trp  [SEQ ID NO: 10]

(D)Val-(L)Val-(D)Val-(L)Val-(D)Val  [SEQ ID NO: 11]

(D)Phe-(L)Phe-(D)Phe-(L)Phe-(D)Phe  [SEQ ID NO: 12]

In the peptide complex, the compound may be represented by Chemical Formula

[Chemical Formula 2]

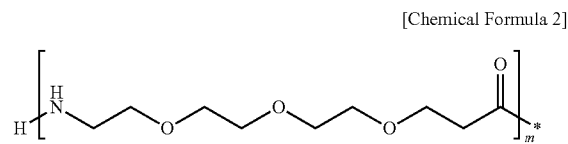

In Chemical Formula 2, m is an integer from 1 to 12.

The peptide complex may be represented by any one of Chemical Formulas 3 to 6.

[Chemical Formula 3]

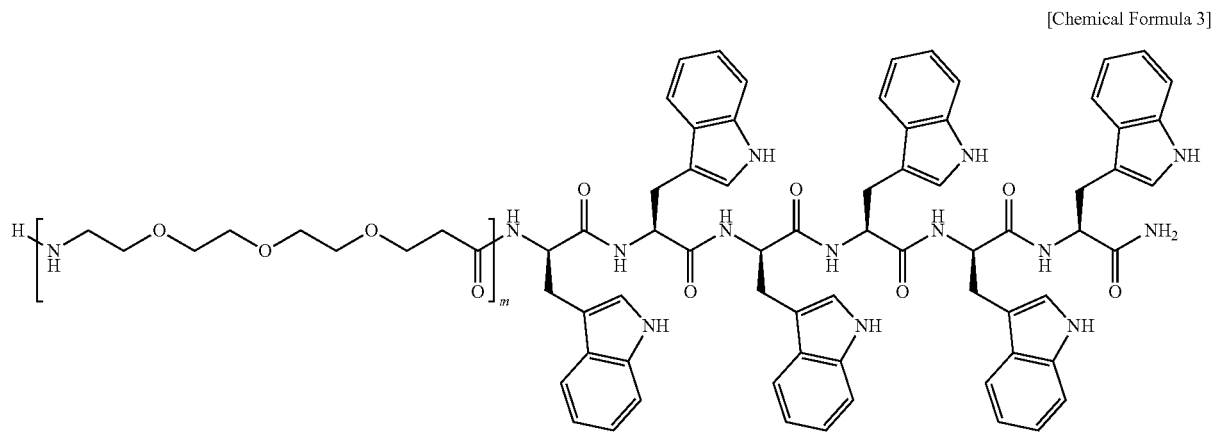

[Chemical Formula 4]

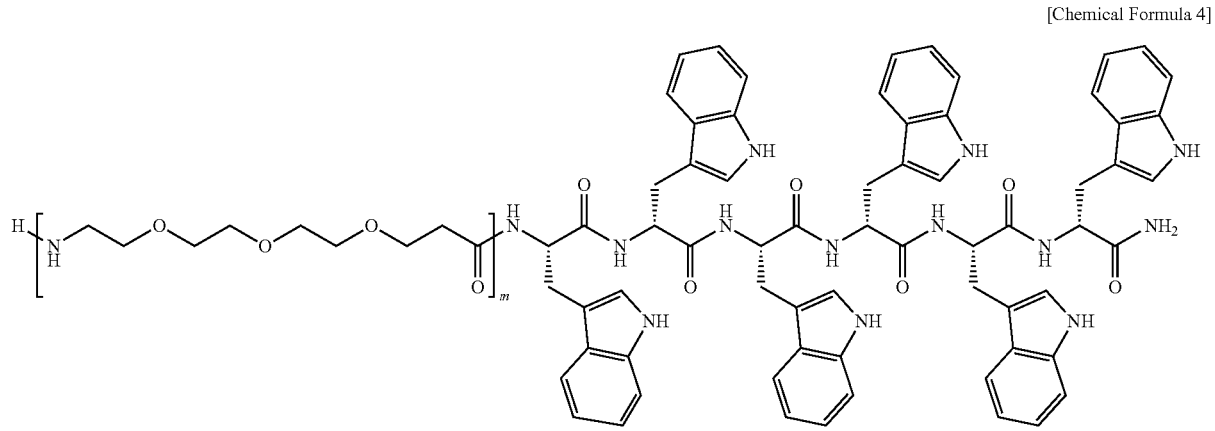

[Chemical Formula 5]

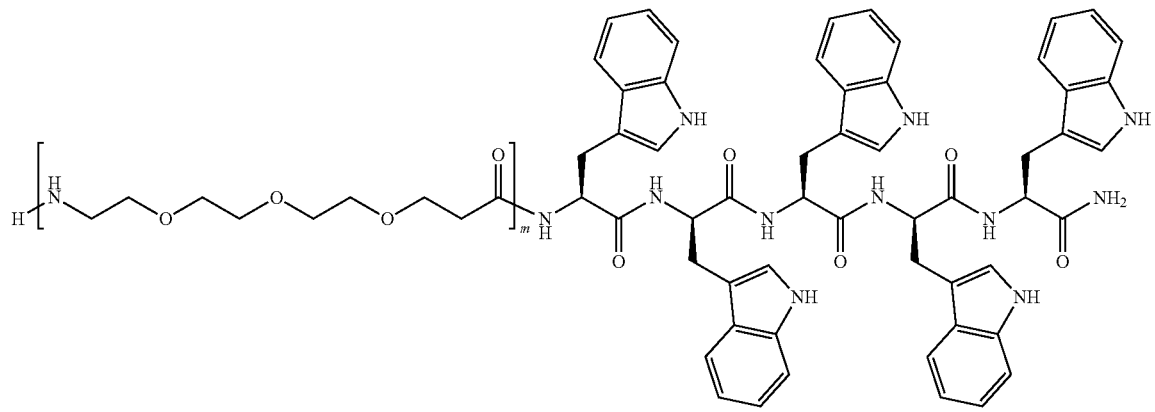

[Chemical Formula 6]

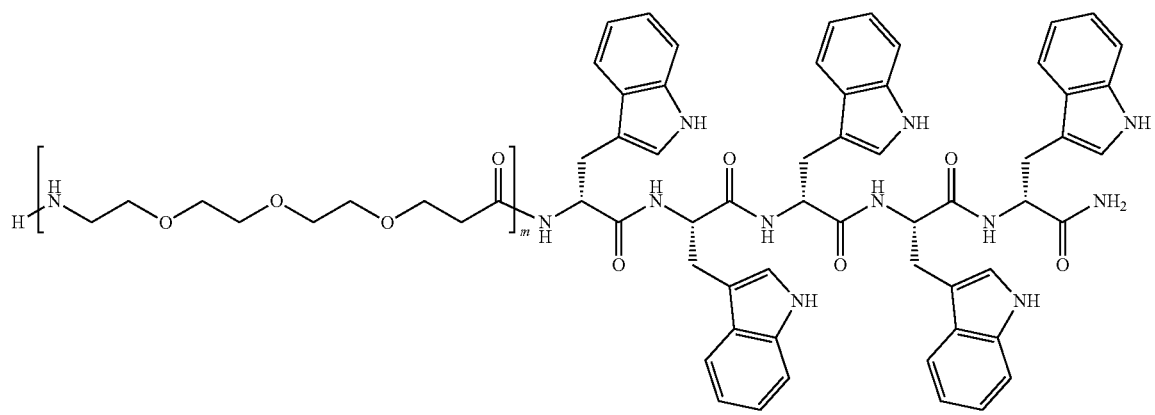

In Chemical Formulas 3 to 6, m is an integer from 1 to 5.

The peptide complex may slowly form a self-assembled structure in solution, wherein, if the a, f, e and j in General Formulas 1 and 2 are 0, an intermediate with a flat ribbon fiber structure may be formed as a helical portion of a fiber structure in which a right-handed helix (P-helix) and a left-handed helix (M-helix) are twisted is fattened laterally with time and a self-assembled structure with a flat ribbon crystal structure may be formed finally.

The peptide complex may slowly form a self-assembled structure in solution, wherein, if the a, f, e and j in General Formulas 1 and 2 are 1 or 2, a self-assembled intermediate composed of: a fiber containing a right-handed helix (P-helix) and a left-handed helix (M-helix) of variable pitch; and a fiber of a sausage-like structure formed from a superhelical fiber formed by overtwisting and intertwining may be formed with time, and a self-assembled structure with a porous superhelical network may be formed finally as intertwining and overtwisting progress extensively.

The present disclosure also provides an alignment medium composition for measuring residual dipolar coupling (RDC), which includes the peptide complex.

The present disclosure also provides a method for analyzing an NMR spectrum of a biomolecule, which includes:
(a) a step of mixing the peptide complex in a mixture solvent;
(b) a step of adding a biomolecule to be measured in the mixture solution; and
(c) a step of conducting NMR measurement for the mixture of the biomolecule and the peptide complex.

The NMR measurement may be conducted by any one selected from a group consisting of $^1H$, $^1H$ edit and 2D NMR.

The mixture solvent may be a mixture of a deuterium solvent and a solvent.

The present disclosure also provides a drug carrier including the peptide complex.

The present disclosure also provides a cell culture scaffold including the peptide complex.

Since the heterochiral peptide complex of the present disclosure contains a polyethylene glycol residue, interactions with an analyte are minimized while affinity to biomolecules is retained. In addition, since the heterochiral peptide complex of the present disclosure contains a β-sheet peptide, it has superior structural stability against environmental factors such as heat, acidity and ionic strength and is applicable as an alignment medium for measuring RDC for various biomolecules.

BRIEF DESCRIPTION OF DRAWINGS

FIG. 3 shows the MALDI-TOF (matrix-assisted laser desorption/ionization time-of-flight) mass spectrometry result of heterochiral peptide complexes prepared in Examples 1-4.

FIG. 4 shows the HPLC analysis result of heterochiral peptide complexes prepared in Examples 1-4.

FIG. 5a shows the CD spectra of the homochiral peptide complexes of Comparative Example 1 and Comparative Example 2, which are enantiomers, FIG. 5b shows the AFM image of the homochiral peptide complex of Comparative Example 1, and FIG. 5c shows the AFM image of the homochiral peptide complex of Comparative Example 2.

FIG. 22 shows the HPLC analysis result of homochiral peptide complexes prepared in Comparative Examples 3-4 and heterochiral peptide complexes prepared in Comparative Examples 5-7.

FIG. 23 shows the HPLC analysis result of heterochiral peptide complexes prepared in Examples 8-11.

FIG. 24 shows the HPLC analysis result of heterochiral peptide complexes prepared in Examples 12-16.

FIG. 25 shows the HPLC analysis result of heterochiral peptide complexes prepared in Examples 17-20.

DETAILED DESCRIPTION OF EMBODIMENTS

Figure 1A:
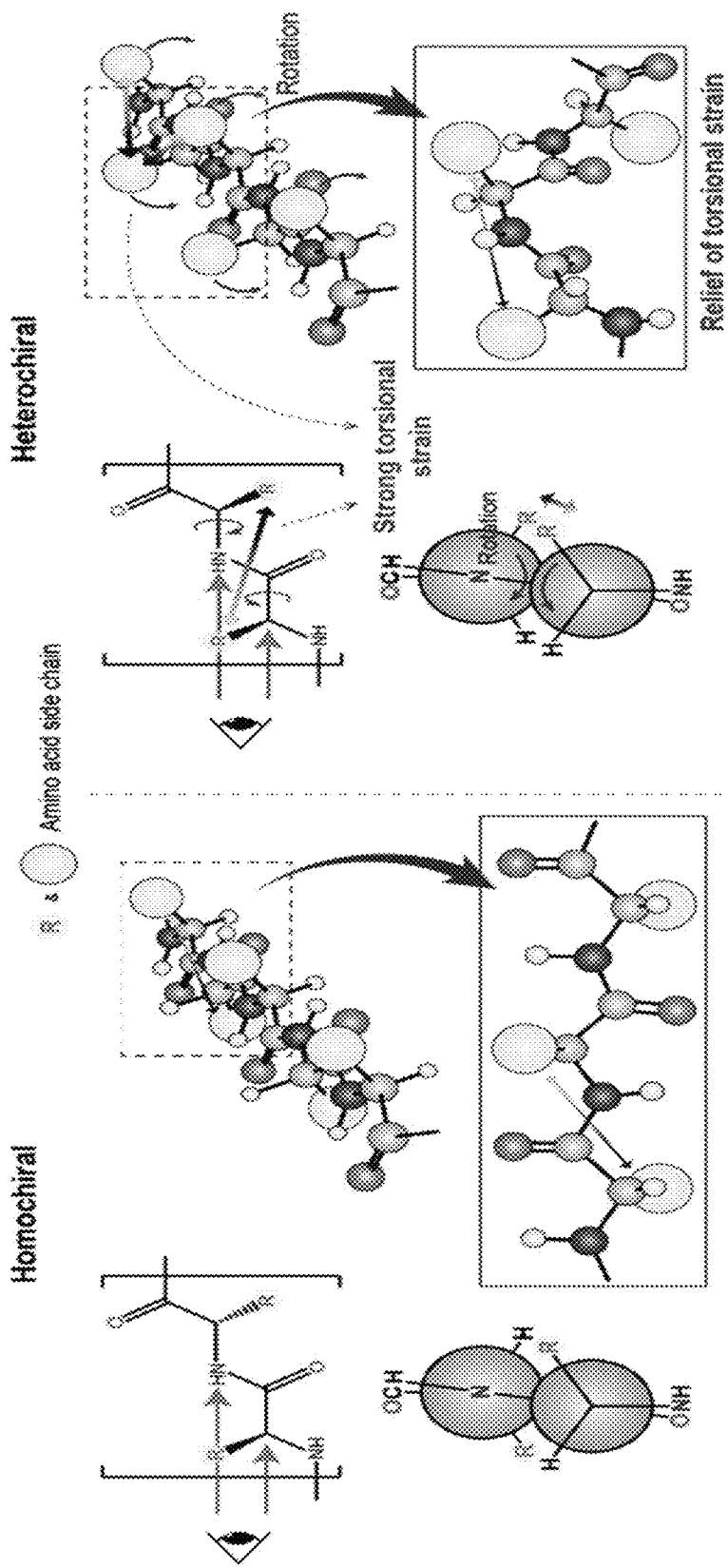
FIG. 1 shows the 3D structure of a heterochiral peptide complex of the present disclosure. The right image in FIG. 1a shows the structure of a homochiral peptide (Comparative Examples 1-2), and the left image in FIG. 1a shows the structure of a heterochiral peptide (Example 1) (alternating L- and D-amino acids).
FIG. 1b shows the chemical structure of amphiphilic peptides of the present disclosure [W (upper case): L-tryptophan, w (lower case): D-tryptophan].

Hereinafter, the present disclosure is described in detail referring to the attached drawings.

Until now, the observation of the self-assembly process of peptides has been very limited. With the existing NMR spectroscopy, it is difficult to characterize multimolecular and large objects due to their slow tumbling rates and short signal relaxation time. The interest in the peptide self-assembly pathway is a relatively recent phenomenon. However, it is beginning to attract widespread attention because of increased researches on disease-related misfolded peptides such as amyloid β (Aβ).

Until the mid-20th century, unnatural D-amino acids have been considered to be unnatural, i.e., not occurring in nature, isomers. However, they are being identified through various researches as useful substances in many aspects. Particularly, the D-amino acids are mainly used in the development of protease-resistant peptides. In the present disclosure, heterochiral peptides are designed by linking D-amino acids and L-amino acids alternatingly. Because they can sample more diverse backbone dihedral angles φ and ψ than homochiral peptides, they can fold or assemble in unique fashions. Gramicidin represents a well-known example of a natural peptide having D-amino acids and L-amino acids, available from a microorganism.

Most self-assembled objects of the peptides are limited to a few typical structures, such as spherical micelles, cylindrical micelles, vesicles, flat membranes and nanotubes. Amyloid β (Aβ) and other misfolded peptides also generally assemble into typical morphologies such as twisted ribbons, multistranded filaments, helical ribbons, nanotubes and crystals. Despite the various researches on misfolded peptide, studies on their morphological transitions and self-assembled intermediates are in the early stage yet.

The inventors of the present disclosure have made efforts to develop a substance capable of overcoming limitations in the method of observing the self-assembly process of self-assembled structures. As a result, they have derived a new peptide complex, elucidated its function and identified that use thereof as an alignment medium for measuring RDC surely provides aligning effect, and have completed the present disclosure.

An aspect of the present disclosure relates to a peptide complex including: a peptide represented by General Formula 1 or 2, which includes heterochiral amino acids, and a compound represented by Chemical Formula 1, which is bound to one end of the peptide.

$$[Y1]_a\text{—}\{\text{—}[X1]_b\text{-}[Y2]_c\}_d\text{—}[X2]_e \qquad \text{[General Formula 1]}$$

$$[X1]_f\text{—}\{\text{—}[Y1]_g\text{—}[X2]_h\}_i\text{—}[Y2]_j \qquad \text{[General Formula 2]}$$

In General Formulas 1 and 2,
each of X1 and X2, which are identical to or different from each other, is independently any one selected from D-Trp, D-Phe, D-Tyr, D-Val, D-Leu and D-Ile,
each of Y1 and Y2, which are identical to or different from each other, is independently any one selected from L-Trp, L-Phe, L-Tyr, L-Val, L-Leu and L-Ile,
each of a, f, e and j is independently an integer selected from 0 to 2, each of b, c, g and h is independently an integer selected from 1 to 5, each of d and i is independently an integer selected from 1 to 10.

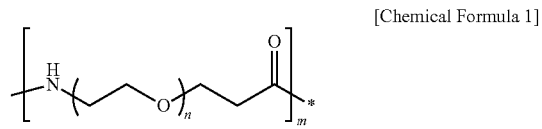

[Chemical Formula 1]

In Chemical Formula 1, each of n and m is independently an integer selected from 1 to 12.

In Chemical Formula 1, n may be selected adequately for solubilization of the peptide complex depending on the length of the peptide. Specifically, n may be an integer from 1 to 5, more specifically an integer from 1 to 3. Most specifically, n may be 3.

In the present disclosure, the abbreviations used to designate amino acids and protecting groups are based on the terms recommended by the Commission of Biochemical Nomenclature of IUPAC-IUB (*Biochemistry* 11: 1726-1732 (1972)). Specifically, 'D-' used in the present disclosure refers to unnatural amino acids (UAAs); D-Trp refers to D-tryptophan, D-Phe to D-phenylalanine, D-Tyr to D-tyrosine, D-Val to D-valine, D-Leu to D-leucine, and D-Ile to D-isoleucine. 'L-' refers to natural amino acids; L-Trp refers to L-tryptophan, L-Phe to L-phenylalanine, L-Tyr to L-tyrosine, L-Val to L-valine, L-Leu to L-leucine, and L-Ile to L-isoleucine.

The term "peptide" used in the present disclosure refers to a full-length peptide composed of one or more amino acid residue according to the present disclosure. In a specific exemplary embodiment, the term "peptide" includes isolated peptides and peptides prepared through protein synthesis by common recombinant methods, e.g., by isolation from a sample followed by purification, which are known to those skilled in the art. Specifically, the entire peptide or a portion thereof may be synthesized by common synthesis methods such as solid-phase peptide synthesis (Merrifield, R. B., *J. Am. Chem. Soc.*, 85: 2149-2154 (1963)). Each amino acid is sometimes referred to as an "amino acid residue or amino acid" in the present disclosure.

Since the peptide of the present disclosure is synthesized at the C-terminal through solid-phase peptide synthesis, the peptide is synthesized as coupling between amino acid residues is completed. During this process, the compound represented by Chemical Formula 1 may also be coupled with the peptide.

The peptide of the present disclosure exists as a stereoisomer or as a mixture of stereoisomers. For example, the peptide may be one in which L-amino acids and D-amino acids are linked alternatingly. Specifically, the peptide of the present disclosure may be formed independently through repeated alternating bonds. Depending on the number of asymmetric carbons, not only a mixture of isomers but also a racemic, diasteromeric mixture or enantiomer mixture or a peptide with an asymmetric heterochiral structure may be obtained. Specifically, the peptide of General Formula 1 or General Formula 2 is a racemic or asymmetric heterochiral peptide.

The peptide of the present disclosure may contain at least one functional group bound to the N-terminal or C-terminal. The at least one functional group may be bonded to the peptide by any means known in the art, specifically via covalent bonding. In a specific exemplary embodiment, the peptide may contain a functional group covalently bonded to the N-terminal and a functional group covalently bonded to the C-terminal.

The functional group bonded to the at least one N-terminal (specifically one N-terminal) may be any one selected from a group consisting of H, acetyl (hereinafter, also referred to as Ac), butanoyl, hexanoyl, 2-methylhexanoyl, cyclohexanecarboxyl, octanoyl, decanoyl, lauroyl, myristoyl, palmitoyl (hereinafter, also referred to as Pal), stearoyl, oleoyl and linoleyl. But, since the compound represented by Chemical Formula 1 is bonded at the N-terminal of the peptide in the present disclosure, the functional group may not be present at the N-terminal.

The functional group bonded to the at least one C-terminal (specifically one C-terminal) may be selected from H, —$NR_1R_2$—, —$OR_1$ and —$SR_1$, wherein each of $R_1$ and $R_2$ is independently any one selected from a group consisting of H, a substituted or unsubstituted acyclic aliphatic group, a substituted or unsubstituted alicyclic group, a substituted or unsubstituted heterocyclic group, a substituted or unsubstituted heteroarylalkyl group, a substituted or unsubstituted aryl group and a substituted or unsubstituted aralkyl group. In a most specific exemplary embodiment, a $NH_2$ functional group may be bonded to at least one C-terminal (specifically one C-terminal).

Accordingly, more specifically, the peptide of the present disclosure contains butanoyl or Ac bonded to the N-terminal and $NH_2$ bonded to the C-terminal.

The inventors of the present disclosure have discovered rare helical intermediates from slowly assembling species and have identified the convergence of morphological space that crosses the chirality barriers in peptide self-assembly.

The inventors of the present disclosure have studied on the energy environment of the self-assembly of the peptides. In solution, the peptide complex is slowly self-assembled and forms a self-assembled intermediate having strong anisotropy until it is fixed as the final self-assembled structure. They have developed a transformable NMR alignment medium based on this information. The design concept of the slowly self-assembling heterochiral peptide complex that has been newly developed in the present disclosure is as follows.

The heterochiral peptide complex of the present disclosure includes a racemic peptide or an asymmetric racemic peptide wherein D- and L-amino acids are linked alternatingly, and the compound represented by Chemical Formula 1 which is bound to one end of the peptide.

FIG. 1 shows the 3D structure of the heterochiral peptide complex of the present disclosure. As shown in the right image in FIG. 1a, in a conventional linear homochiral peptide (composed of L- or D-amino acids only), a conformationally stable state is achieved when alternating amide bonds are placed 180° from each other and the side chains at the opposite sides of the peptide backbone face each other.

However, as shown in the left image of FIG. 1a, the linear heterochiral peptide with alternating D/L-amino acids would have a less optimal conformation for efficient noncovalent bond (especially hydrogen bond) formation than its homochiral counterpart because the molecule is likely to exist in a distorted conformation to alleviate the torsional strains from adjacent side chains. Due to this conformational difference, the homochiral peptide forms an aggregate having stronger anisotropy than the heterochiral peptide.

Figure 1B:
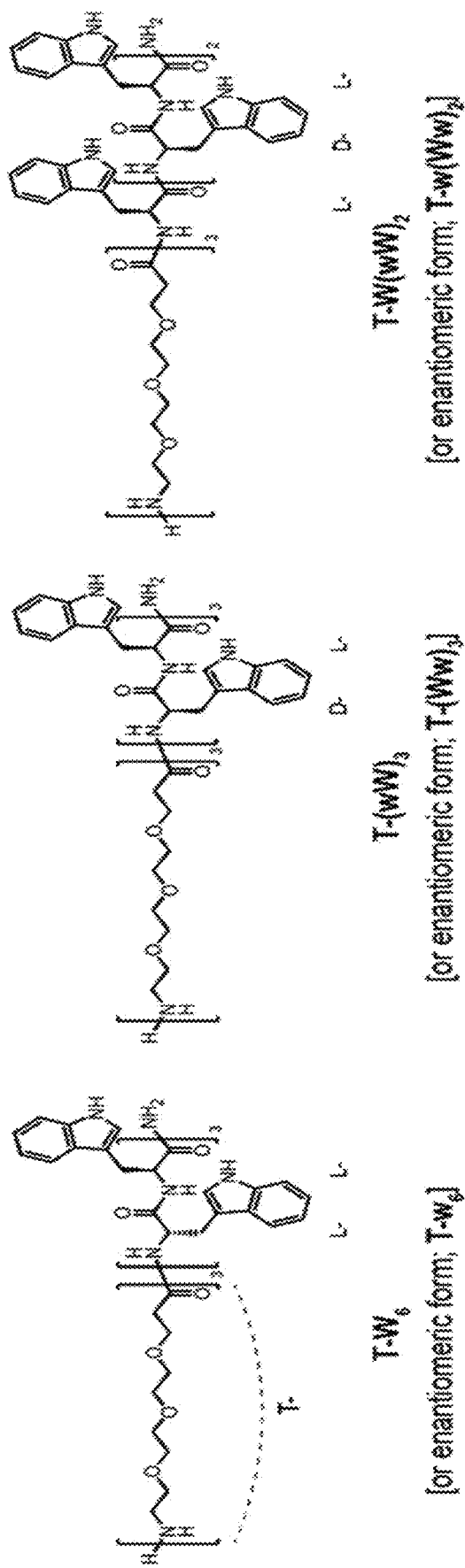

Based on these premises, the inventors of the present disclosure hypothesized that a self-assembled intermediate might be able to be identified if the heterochiral peptide would aggregate slowly enough to be directly observed by microscopy. Therefore, the inventors have designed the peptide complex of the present disclosure. Specifically, the peptide complex has an amphiphilic building block which consists of a β-sheet-forming hydrophobic segment containing a heterochiral amino acid, which forms the peptide represented by General Formula 1 or 2, and a hydrophilic segment, which is the compound represented by Chemical Formula 1 bound to one end of the peptide (FIG. 1b). Accordingly, the peptide complex having the peptide and the compound according to the present disclosure has thermal and physical stability because it is self-assembled in solution and the helical arrangement in M and P directions is increased, by the peptide having a β-sheet structure through interstrand hydrogen bonds.

In a specific exemplary embodiment, in General Formulas 1 and 2, each of X1 and X2, which are identical to or different from each other, may be independently any one selected from D-Trp, D-Val and D-Phe, and each of Y1 and Y2, which are identical to or different from each other, may be independently any one selected from L-Trp, L-Val and L-Phe.

More specifically, in General Formulas 1 and 2, each of X1 and X2, which are identical to or different from each other, may be independently any one selected from D-Trp, D-Val and D-Phe, and each of Y1 and Y2, which are identical to or different from each other, may be independently any one selected from L-Trp, L-Val and L-Phe.

In a more specific exemplary embodiment, X1 and X2 may be identical to each other, and Y1 and Y2 may be identical to each other.

The ratio of the hydrophobic segment and the hydrophilic segment may be determined for solubilization of the peptide complex. Specifically, the ratio of the segments in the peptide complex of the present disclosure is as follows. In General Formulas 1 and 2, each of a, f, e and j may be independently an integer selected from 0 to 2, each of b, c, g and h may be independently an integer selected from 1 to 3, and each of d and i may be independently an integer selected from 1 to 4.

More specifically, the peptide may be any one selected from the heterochiral peptides represented by SEQ ID NOS: 1 to 12, further more specifically any one selected from the heterochiral peptides represented by SEQ ID NOS: 1, 2, 4, 5, 7, 8, 10 and 11, most specifically any one selected from the heterochiral peptides represented by SEQ ID NOS: 1, 4, 7 and 10.

| | |
|---|---|
| (D)Trp-(L)Trp-(D)Trp-(L)Trp-(D)Trp-(L)Trp | [SEQ ID NO: 1] |
| (D)Val-(L)Val-(D)Val-(L)Val-(D)Val-(L)Val | [SEQ ID NO: 2] |
| (D)Phe-(L)Phe-(D)Phe-(L)Phe-(D)Phe-(L)Phe | [SEQ ID NO: 3] |
| (L)Trp-(D)Trp-(L)Trp-(D)Trp-(L)Trp-(D)Trp | [SEQ ID NO: 4] |
| (L)Val-(D)Val-(L)Val-(D)Val-(L)Val-(D)Val | [SEQ ID NO: 5] |
| (L)Phe-(D)Phe-(L)Phe-(D)Phe-(L)Phe-(D)Phe | [SEQ ID NO: 6] |

(L)Trp-(D)Trp-(L)Trp-(D)Trp-(L)Trp [SEQ ID NO: 7]

(L)Val-(D)Val-(L)Val-(D)Val-(L)Val [SEQ ID NO: 8]

(L)Phe-(D)Phe-(L)Phe-(D)Phe-(L)Phe [SEQ ID NO: 9]

(D)Trp-(L)Trp-(D)Trp-(L)Trp-(D)Trp [SEQ ID NO: 10]

(D)Val-(L)Val-(D)Val-(L)Val-(D)Val [SEQ ID NO: 11]

(D)Phe-(L)Phe-(D)Phe-(L)Phe-(D)Phe [SEQ ID NO: 12]

In the above peptide sequences, D refers to a 'D-amino acid residue', and L refers to an 'L-amino acid residue'.

In the peptide complex, the compound may be represented by Chemical Formula 2.

[Chemical Formula 2]

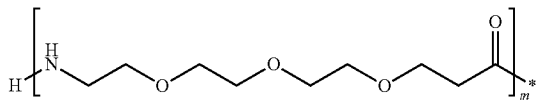

In Chemical Formula 2, m is an integer from 1 to 12.

Accordingly, most specifically, the peptide complex according to the present disclosure may be represented by any one of Chemical Formulas 3 to 6.

[Chemical Formula 3]

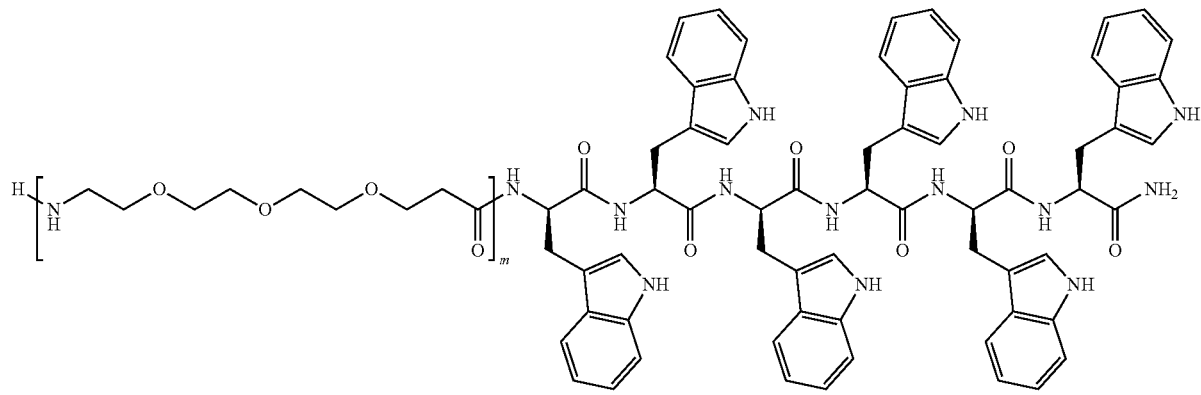

[Chemical Formula 4]

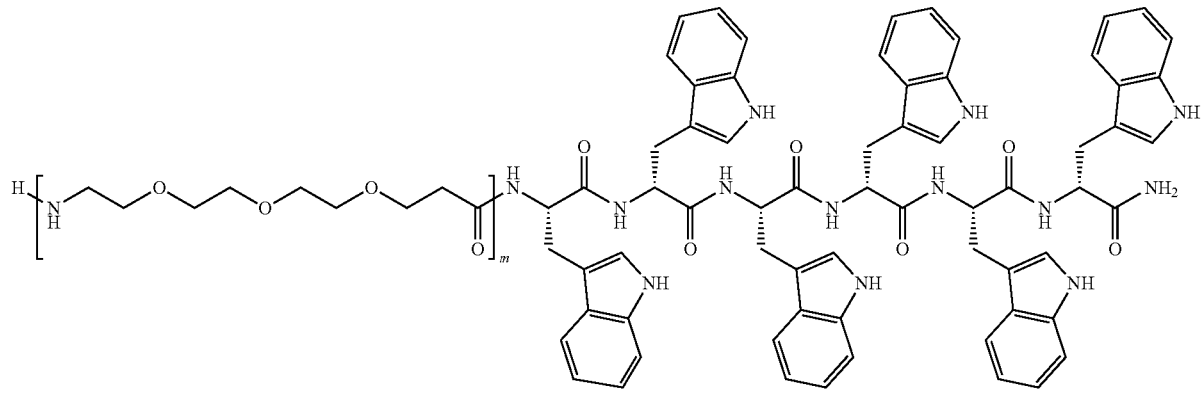

[Chemical Formula 5]

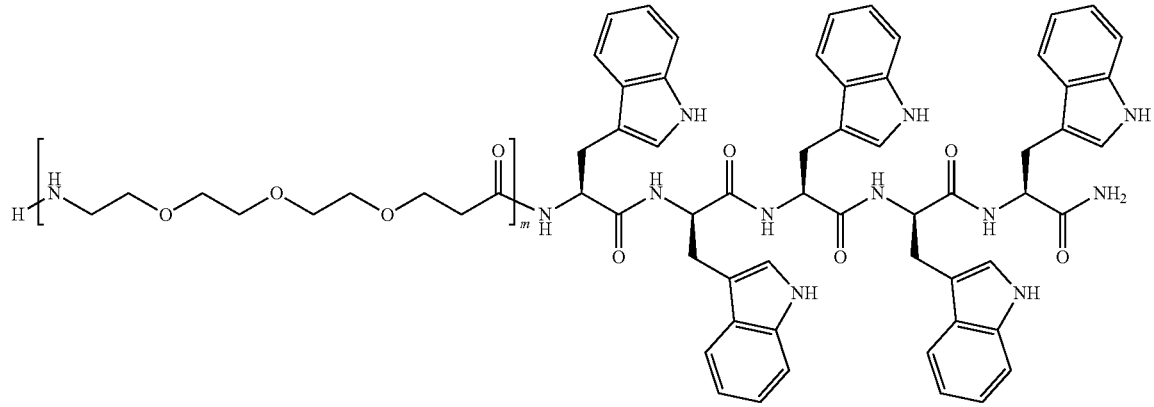

[Chemical Formula 6]

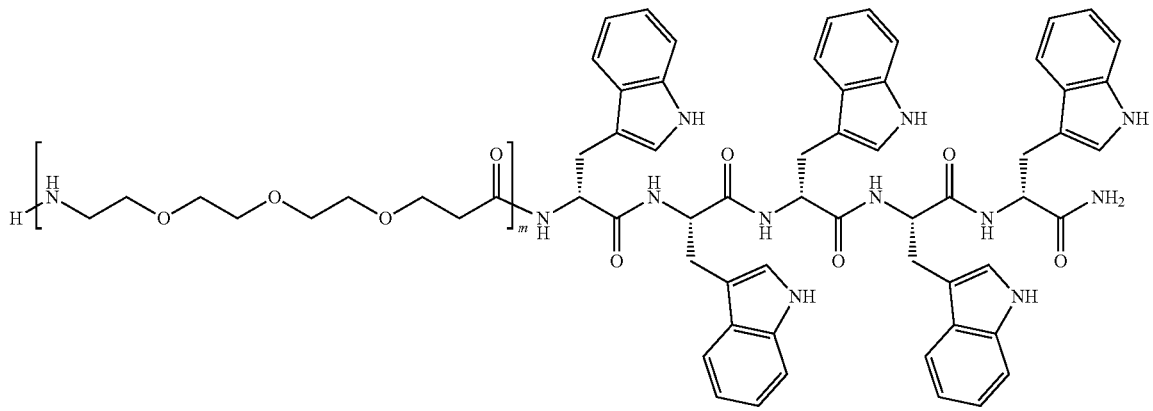

In Chemical Formulas 3 to 6, m is an integer from 2 to 5.

The peptide of the present disclosure may be synthesized or produced by any method known in the art. For example, it may be synthesized chemically (specifically by solid-phase peptide synthesis) or may be produced by transgenic production in a plant or an animal. In addition, the peptide of the present disclosure may be purified by any means known in the art.

As can be clearly seen from the examples described below, the peptide complex of the present disclosure is slowly self-assembled in solution through the same principle as structural formation of proteins. Therefore, the general self-assembly of peptides, proteins or amyloid can be inferred based thereon. In addition, as can be derived from the examples described below, the peptide complex of the present disclosure is directly applicable as an alignment medium for RDC measurement in NMR spectroscopy because it is biologically compatible and easy to prepare, has superior structural stability and can be maintained for a long time as a self-assembled intermediate. Accordingly, the self-assembled intermediate of the peptide complex of the present disclosure may be provided as an additional or alternative peptide complex capable of providing excellent structural stability against environmental factors such as heat, acidity and ionic strength because it has improved alignment characteristics due to strong anisotropy and is based on the β-sheet structure.

The peptide complex slowly forms a self-assembled structure in solution. If the a, f, e and j in General Formulas 1 and 2 are 0, an intermediate with a flat ribbon fiber structure may be formed as a helical portion of a fiber structure in which a right-handed helix (P-helix) and a left-handed helix (M-helix) are twisted is fattened laterally with time, and a self-assembled structure with a flat ribbon crystal structure may be formed finally.

If the a, f, e and j in General Formulas 1 and 2 are 1 or 2, a self-assembled intermediate composed of: a fiber containing a right-handed helix (P-helix) and a left-handed helix (M-helix) of variable pitch; and a fiber of a sausage-like structure formed from a superhelical fiber formed by overtwisting and intertwining may be formed with time, and a self-assembled structure with a porous superhelical network may be formed finally as intertwining and overtwisting progress extensively.

Since the self-assembled intermediate of the peptide complex has strong anisotropy, it may be used as an alignment medium that enables accurate measurement of NMR residual dipolar coupling (NMR-RDC). That is to say, the peptide complex of the present disclosure can be used to determine the structure of various important biomedical molecules through accurate measurement of NMR-RDC. In addition, it can be used as a drug carrier or a scaffold for cell culturing.

Another aspect of the present disclosure relates to a self-assembled intermediate formed through self-assembly of the peptide complex.

The peptide complex is slowly self-assembled in solution to form a self-assembled intermediate. Specifically, the self-assembled intermediate of the peptide complex has a fiber structure in which right-handed helix (P-helix) and a left-handed helix (M-helix) are twisted and is composed of: a fiber composed of an intermediate with a flat ribbon fiber structure formed as the helices of the fiber are fattened laterally or a right-handed helix (P-helix) and a left-handed helix (M-helix) of variable pitch; and a fiber of a sausage-like structure formed from a superhelical fiber formed by overtwisting and intertwining. The P-helix and the M-helix are present in almost the same ratio.

Another aspect of the present disclosure relates to an alignment medium composition for experimental analysis of residual dipolar coupling (RDC), which includes the peptide complex.

In addition, the present disclosure provides a novel use of the peptide complex as an alignment medium for experimental analysis of residual dipolar coupling (RDC).

NMR is advantageous in that data can be obtained in solution state without requiring crystals. Like X-ray crystallography, the structure of biomolecules such as proteins cannot be acquired directly from NMR measurement, but the tertiary structure is determined through computational simulation of experimental data. Specifically, NMR in the nuclei of the atoms constituting a biomolecule have an intrinsic magnetic moment because protons and neutrons have a spin angular momentum $S=\frac{1}{2}$. When the number of the protons or neutrons is an odd number, the whole nucleus has a nonzero magnetic moment. In this case, energy level splitting occurs by an external magnetic field. The energy splitting may resonate with an external electromagnetic wave (mainly a radio wave). The spectra of hydrogens (H) can be measured using this phenomenon, and the information about the distance between several hydrogen atoms constituting a protein and the information about the dihedral angles between the protein backbone and side chains can be obtained under confined conditions by analyzing the spectra. Especially, the information about the distance between the hydrogen atoms that plays a critical role in structure determination is called the nuclear Overhauser effect (NOE) distance restraint.

In NMR, several experiments are employed for determination of the 3D structure of biomolecules. For biomolecules which are smaller than 20 kDa in size, residual dipolar coupling (RDC) measurement, which allows the determination of 3D alignments of the backbone, side chains and domains of the biomolecule, is employed because transverse relaxation-optimized spectroscopy (TROSY) analysis is limited.

For RDC measurement, lipid bicelles are added to biomolecules in an aqueous solution and a magnetic field is applied. Then, the bicelles are aligned by the magnetic field, and the biomolecules are aligned along the bicelles. Through this, dipolar coupling is generated between the nuclear spins of two atoms, and energy splitting is observed due to resonance depending on the frequency of the external magnetic. This phenomenon is called residual dipolar coupling (RDC). The information about the arrangement of domains of a protein can be obtained based thereon.

As mentioned above, previously known alignment media include lipids such as bicelles, nematic liquid crystal molecules, compressed or stretched polymer gels and Pf1 filamentous phages. However, these alignment media are restricted in conditions such as temperature, pH, solvent, etc., have low structural stability and are difficult to prepare.

In contrast, the peptide complex of the present disclosure is easy to prepare and is biologically compatible, is not limited by temperature, pH and solvent conditions, and has superior structural stability. In addition, the peptide complex of the present disclosure can induce stable alignment of biomolecules by forming an intermediate having strong anisotropy through self-assembly in solution without an additional process.

In addition, the peptide complex of the present disclosure has high thermal and physical stability because it is based on a peptide having a β-sheet structure, has superior solubility in solvents used in NMR measurement, and enables good alignment of biomolecules. These characteristics are remarkably superior effects that cannot be achieved with the homochiral peptide-based complexes (Comparative Examples 1-2) having the same final self-assembled structures as that of the peptide complex of the present disclosure.

Accordingly, the self-assembled intermediate of the peptide complex of the present disclosure can effectively act as an alignment medium which allows NMR analysis, especially accurate precision of RDC.

Another aspect of the present disclosure provides a method for conducting NMR analysis of a biomolecule, which includes:
(a) a step of mixing the peptide complex in a solution,
(b) a step of adding a sample including a biomolecule to be measured in the mixture solution; and
(c) a step of conducting NMR measurement for the mixture of the sample and the peptide complex.

The method of the present disclosure is a method for conducting NMR analysis, especially RDC analysis, of a biomolecule. According to the method, the 3D structure of a biomolecule may be analyzed by mixing the peptide complex in a solution, thereby forming a self-assembled intermediate having anisotropy, inducing alignment of the biomolecule and then conducting NMR spectroscopy on the biomolecule.

The NMR measurement may be conducted by any one selected from a group consisting of $^1$H, $^1$H edit and 2D NMR. However, any commonly used method may be used without limitation without being limited thereto.

The 2D NMR method may be any one commonly used. Specifically, one or more selected from a group consisting of residual dipolar coupling (RDC), $^1$H-$^1$H correlation spectroscopy (COSY) and $^1$H-$^{13}$C heteronuclear single-quantum coherence spectroscopy (HSQC) may be used.

In order to conduct NMR, the peptide complex and the biomolecule are mixed sequentially in a mixture solvent. The mixture solvent may be a mixture of a deuterium solvent and a solvent. The deuterium solvent may be one or more selected from chloroform-d ($CDCl_3$), deuterium oxide ($D_2O$), dimethyl sulfoxide-$d_6$ (DMSO-$d_6$), N,N-dimethylformamide (DMF)-$d_7$, N-methylpyrrolidone (NMP)-$d_9$ and a mixture thereof, and the solvent may be distilled water or methanol.

In the mixture solvent, the mixing volume ratio of the deuterium solvent and the solvent may be 1:1-10, specifically 1:4-10, more specifically 1:6-10, most specifically 1:9.

The biomolecule may be sampled using the mixture solvent. The sampling means pretreatment. NMR experiment may be conducted by adding the peptide complex of the present disclosure together with the sample.

The sequence of addition to the mixture solvent is not particularly limited. The peptide complex and the biomolecule may be added sequentially or simultaneously.

The biomolecule may be one or more selected from a group consisting of a peptide, a protein, a nucleic acid and a polysaccharide, although not being specially limited thereto. For example, the nucleic acid may be selected from a group consisting of a DNA, an RNA, a PNA, an LNA and a hybrid thereof. The protein may be selected from a group consisting of an enzyme, a substrate, an antigen, an antibody, a ligand, an aptamer and a receptor. The peptide refers to a polymer in which a plurality of amino acid residues are linked by peptide bonds, and can be used interchangeably with 'polypeptide' 'oligopeptide' and 'protein'.

Another aspect of the present disclosure relates to a drug carrier including the peptide complex.

In addition, the present disclosure provides a novel use of the peptide complex as a carrier for drug delivery.

The drug carrier of the present disclosure can stably entrap a drug in the β-sheet and 3D network structures or entrap a hydrophobic drug in a hydrophobic region of the self-assembled structure. Through this, the aggregation or degeneration of the drug can be prevented and the drug activity can be maintained more stably for a long time. In addition, the drug can be stabilized structurally and its half-life can be increased.

In the present disclosure, "hydrophobic" refers to the property of a substance which does not binds well with water molecules, does not dissolve well in water or is nonpolar. The term "hydrophobic" may be used interchangeably with the term "lipophilic". Hydrophobic substances may be classified as follows depending on water solubility: slightly solubility (1-10 mg/mL); very slightly soluble (0.1-1 mg/mL); substantially insoluble (<0.1 mg/mL).

In the present disclosure, the drug may be specifically a hydrophobic drug, although not specially being limited thereto. The hydrophobic drug may include a chemical substance or a biodrug having a water solubility of about 10 mg/mL or lower. For example, the hydrophobic drug may be an anthracycline-based drug, a hydrophobic glucocorticoid, a steroid-based drug, a taxane-based drug, a cyclic peptide-based drug or a combination thereof. The anthracycline-based drug may be doxorubicin, daunorubicin, epirubicin, idarubicin, valrubicin, mitoxantrone or a combination thereof. The hydrophobic glucocorticoid may be, for example, dexamethasone, triamcinolone, beclomethasone dipropionate, triamcinolone acetonide, triamcinolone diacetate, betamethasone dipropionate, testosterone, budesonide, 17α-ethinylestradiol, levonorgestrel, fluticasone propionate or a combination thereof. For example, the hydrophobic drug may be sorafenib, paclitaxel, docetaxel, doxorubicin, cyclosporine A, amphotericin B, indinavir, rapamycin, coenzyme $Q_{10}$, ursodeoxycholic acid, ilaprazole, imatinib mesylate, tanespimycin or a combination thereof. A contrast agent (imaging agent or contrast medium) refers to a substance which increases the contrast of an image by artificially increasing the difference in X-ray absorption by different tissues to improve the visibility of tissues or blood vessels in magnetic resonance imaging or computed tomography. The contrast agent may be, for example, a transition element or a chelate complex of a transition element.

The drug carrier according to the present disclosure has an effect of structurally stabilizing a protein or a peptide drug and enhancing its half-life. In addition, it slowly releases the drug in a sustained manner and has biocompatible and biodegradable characteristics.

The concentration of the drug encapsulated in the drug carrier is not specially limited. Specifically, it may not lower than the concentration at which the drug can exhibit efficacy in vivo after being released from the drug carrier of the present disclosure, and not higher than the concentration at which excessive aggregation or inactivation of the drug occurs during the preparation of an aqueous solution or the drug carrier. The concentration may vary depending on the particular drugs and may be, for example, 0.01-1000 mg/mL. When preparing an aqueous solution of the drug, it is preferred to slowly dissolve the drug without stirring in order to avoid aggregation of the drug.

A higher drug weight ratio and better drug encapsulation efficiency may be achieved when a drug carrier is prepared using the peptide complex according to the present disclosure as compared to when a drug is encapsulated in the peptide complex of Comparative Example 1 or 2, which is self-assembled immediately, unlike the peptide complex according to the present disclosure which is self-assembled slowly. The peptide complex can minimize drug loss by protecting the drug encapsulated therein during the self-assembly process.

Another aspect of the present disclosure relates to a cell culture scaffold including the peptide complex.

In addition, the present disclosure provides a novel use of the peptide complex as a scaffold for cell culturing.

In the present disclosure the "scaffold" is a term used in tissue engineering and refers to a structure on which cells are adhered. A bioscaffold refers to a biostructure, i.e., a structure (template) obtained by removing cells from an organ by decellularization. In particular, in the present disclosure, the peptide complex may be self-assembled into a β-sheet or a 3D network.

Since the peptide complex according to the present disclosure forms a biodegradable structure that provides a place wherein cells can be transplanted and grown by forming the β-sheet and 3D network structure in solution through self-assembly, it can provide a superior effect as a scaffold.

The peptide complex according to the present disclosure can easily induce the proliferation of cells without cell death because it lacks cytotoxicity. Accordingly, it may be utilized as a scaffold for preparing a therapeutic biological tissue using cells. In addition, it may be used as a scaffold for producing various artificial organs such as artificial skin, artificial hair, artificial kidney, etc. for implantation.

In the present disclosure, "regeneration" generally refers to the process of restoration or recovery of the tissue of a living organism or its function. In the present disclosure, the regeneration may include all the processes of restoring or recovering a damaged or lost biological tissue or its function.

In addition, the peptide complex may be used by being coated on the surface of an artificial organ, e.g., artificial joint.

Hereinafter, the present disclosure is described in more detail through specific examples. However, the examples are provided only for illustrating the present disclosure in more detail, and it will be obvious to those having ordinary skill in the art that the scope of the present disclosure is not limited by them.

<Materials>

All the D-forms and L-forms of protected Fmoc amino acid derivatives and 12-(Fmoc-amino)-4,7,10-trioxadodecanoic acid (Fmoc-PEG3-propionic acid) or Fmoc-amino-PEG10-propionic acid) were purchased from Anaspec (USA) and AAPPTec (USA). Rink Amide MBHA resin LL was obtained from Novabiochem (Germany).

1-Hydroxybenzotriazole (HOBt) and O-(6-chlorobenzotriazol-1-yl)-N,N,N',N'-tetramethyluronium hexafluorophosphate (HCTU) were acquired from Anaspec and AAPPTec. All other general chemicals including N-methyl-2-pyrrolidone (NMP) and dimethylformamide (DMF) were obtained from Thermo Fisher Scientific (USA) and Samchun (Korea).

<Methods>

1. Circular Dichroism (CD)

The CD spectra of the peptide complexes in aqueous solution were acquired using a Chirascan™ CD spectrometer. All the peptide complexes were adjusted to 20 μM with DI water and then incubated at room temperature for 2 hours. The CD spectra were recorded using a 2-mm pathlength cuvette from 250 nm to 190 nm at 25° C. Each spectrum was collected by averaging three scans and corrected for the distilled water background spectrum.

2. Atomic Force Microscopy (AFM)

The peptide complex samples were diluted to 20 μM and 10 μL was dropped onto a freshly cleaved mica plate. After 1 minute of incubation, the mica plate was washed with 100 μL of doubly distilled water and then the residual solution was gently removed using filter paper. After completely drying at room temperature, AFM measurement was made. The AFM scans were conducted at noncontact mode (NCM) with a Park NX10 instrument (Park Systems, Korea). The scanning was performed at a scan rate of 0.3 Hz and a Z-gain of 1.

3. Wide-Angle X-Ray Scattering (WAXS)

Wide-angle X-ray scattering analysis was performed using the 4C SAXS II beamline (BL) of the Pohang Accelerator Laboratory (PAL, Korea). In-vacuum undulator 20 of the Pohang Light Source II storage ring was used as a beam source, and a vertical toroidal focusing mirror was used to deliver an X-ray beam of 0.675 Å. 100 μL of the sample solution was mounted in a quartz microcapillary with a thickness of 10 μm and a length of 80 mm. The sample was irradiated for 5 seconds of exposure time at room temperature. The concentrations of the samples of Comparative Examples 1-2 and Example 1 (T-$W_6$, T-$w_6$ and T-$(wW)_3$) were all 3.0 mg/mL. The X-ray scattering patterns were collected by using a charge-coupled detector (Mar USA, Inc.) positioned 20 cm apart from the sample (0.25 Å$^{-1}$<q<2.00 Å$^{-1}$).

The data were captured in six continuous frames of 0.1 minute each to minimize the damage from irradiation. Each 2D scattering pattern was averaged circularly from the beam focus and normalized to the intensity of the transmitted X-ray beam. The transmitted beam intensity was monitored with a scintillation counter. The scattering pattern of water was used as the experimental background.

4. Nuclear Magnetic Resonance (NMR) Spectroscopy $^2$H-NMR spectra were recorded using Bruker System 700 Ascend equipped with a TXI probe (5 mm) with a z-gradient ($^2$H: 107.48 MHz) at 298 K. All measurements were carried out in aqueous environment of 10% (v/v) D$_2$O. The specific parameters for the NMR measurement are as follows:

Time domain (TD)=65536
Number of scans (NS)=1
Spectral width (SW)=24 [ppm]
Acquisition time (AQ)=12.7 [sec]
Nucleus=2H
Transmitter freq. offset=516.86 [Hz]/4.809 [ppm]

The chemical shift (δ) was recorded in ppm (parts per million) units and was relative to the residual solvent protons. Each sample was measured in a range from 0 to 24 ppm (SW). Coupling constants (J) were calculated in hertz (Hz) units. All the samples were concentrated to 8 mg/mL.

All the samples were heated at 95° C. for 1 hour and slowly annealed in a water bath overnight. The samples of Comparative Examples 1-2 and Example 1 (T-W$_6$ and T-(wW)$_3$) were incubated for 2 hours or for 2 weeks before the measurement.

5. Molecular Modeling and Dynamics (1) 3D Modeling and Optimization (Model Systems and Energy Minimization)

Maestro 11 software (Schrodinger, LLC) was used for 3D modeling and optimization. The 3D models of the (wW)$_3$ ((D)Trp-(L)Trp-(D)Trp-(L)Trp-(D)Trp-(L)Trp: SEQ ID NO: 1) peptide were generated with two methods.

For the first simulation model, the (wW)$_3$ ((D)Trp-(L)Trp-(D)Trp-(L)Trp-(D)Trp-(L)Trp: SEQ ID NO: 1) peptide structure was arbitrarily elongated with fixed dihedral angles (φ=−180°, ψ=−180°) without any constraints. For the second model, the structure of D/L-alternating poly(tyrosine) (Protein Data Bank entry 1 UNO) was used to create a 3D structure by replacing all the side chains with D- and L-Trp residues in their respective positions.

All conformations were optimized energetically by the Polak-Ribiere conjugate gradient (PRCG) and the truncated Newton conjugate gradient (TNCG) method. At each step, the procedure was iterated until the gradient converged using AMBER as the force field (convergence threshold of 0.05).

(2) Molecular Dynamics (MD)

Using two strands of the energy-optimized structure, structure groups similar to β-sheet-like parallel strand formation were generated based on the distance information from 1 D-WAXS (interstrand distance of 6 Å). The simulation was performed for a total of 50 ns, three times for each model. The implicit solvent system using AMBER as the force field was used. The energies for each interaction were calculated using the generalized Born model. In the Born calculation, the dielectric constants for inside and outside of the molecules were set to 1.0 and 78.5, respectively.

A volume-based continuum solvation model (GB/SA model) was used for the polar component. The bond lengths to hydrogens were constrained to equilibrium lengths using the SHAKE component. The cut-off distance parameters for noncovalent interactions such as van der Waals interaction, electrostatic interaction and hydrogen bonding were set to 8.0 Å, 20.0 Å and 4.0 Å, respectively. The time integration step was 1.0 fs and the intervals were set to 5.0 µs for equilibration in all simulation processes. For better similarity with the state of the sample at 25° C., the calculation was performed at 298 K without any symmetry restrictions or constraints.

Example 1. Synthesis of Heterochiral Peptide Complex, T-(wW)$_3$

Figure 2:
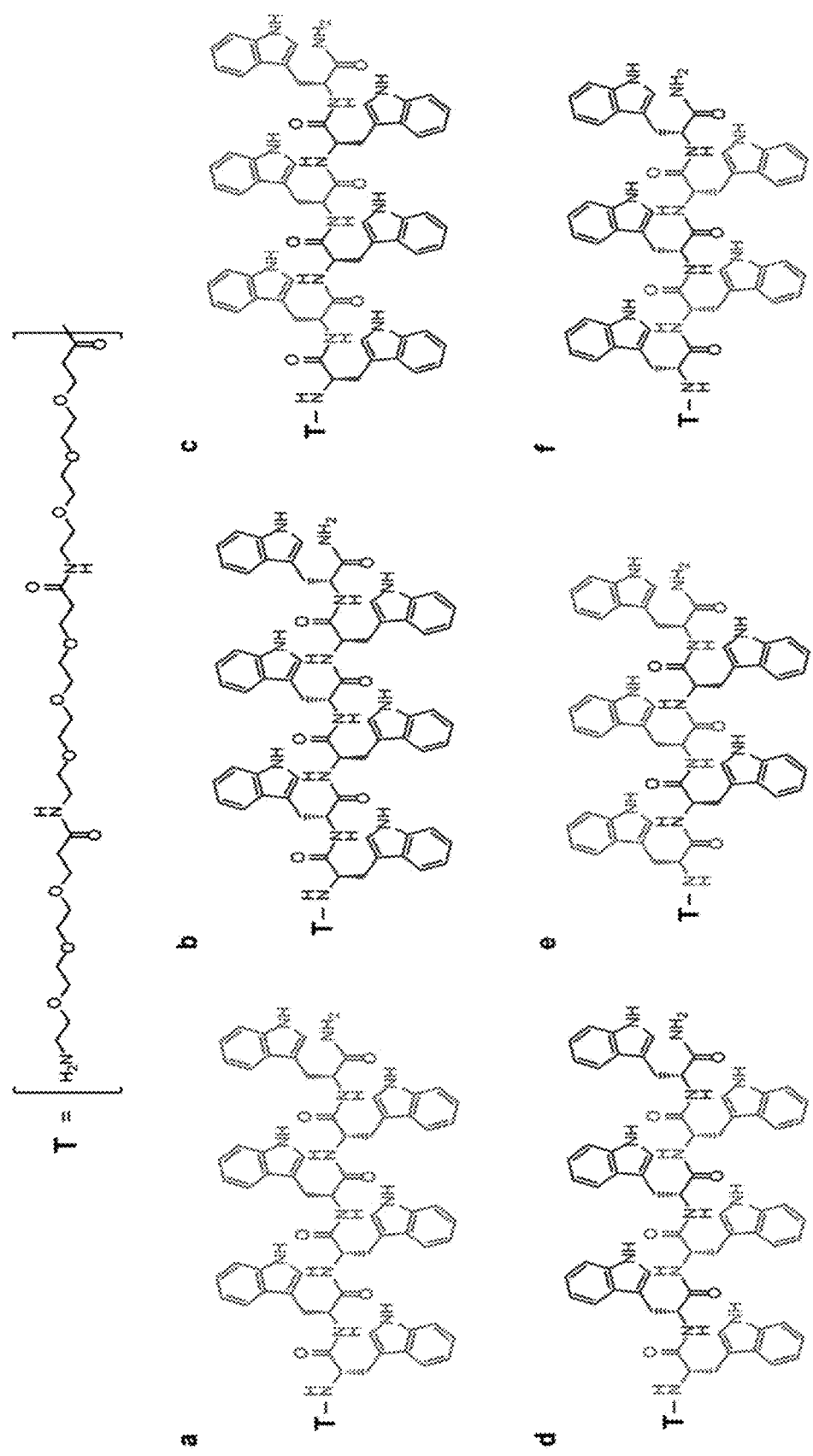
FIG. 2 shows the chemical structure of heterochiral peptide complexes prepared in Examples 1-4 and homochiral peptide complexes prepared in Comparative Examples 1-2.
Figure 3A:
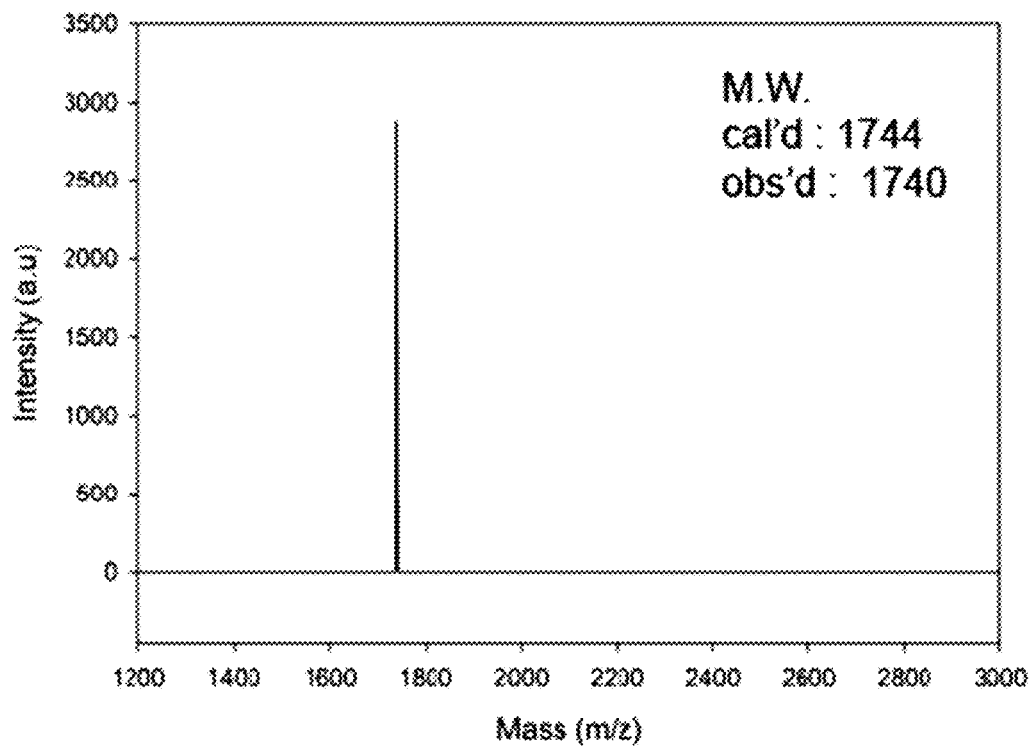
FIG. 3a: homochiral peptide complex prepared in Comparative Example 1.
Figure 3B:
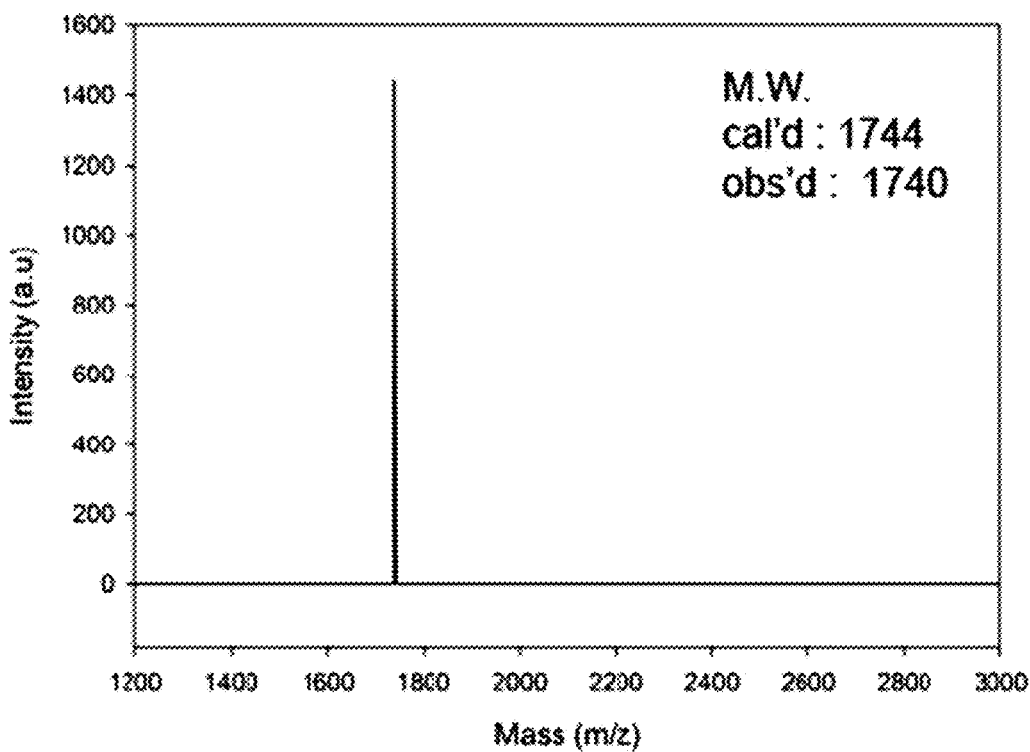
FIG. 3b: homochiral peptide complex prepared in Comparative Example 2.
Figure 3C:
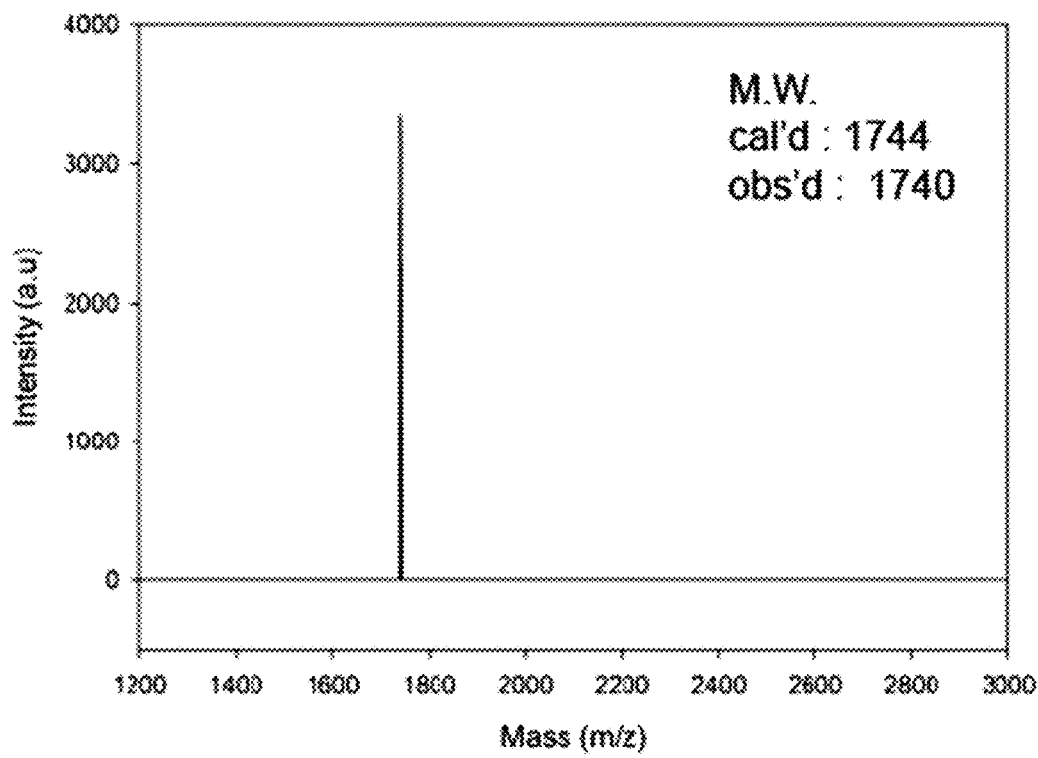
FIG. 3c: heterochiral peptide complex prepared in Example 1.
Figure 4A:
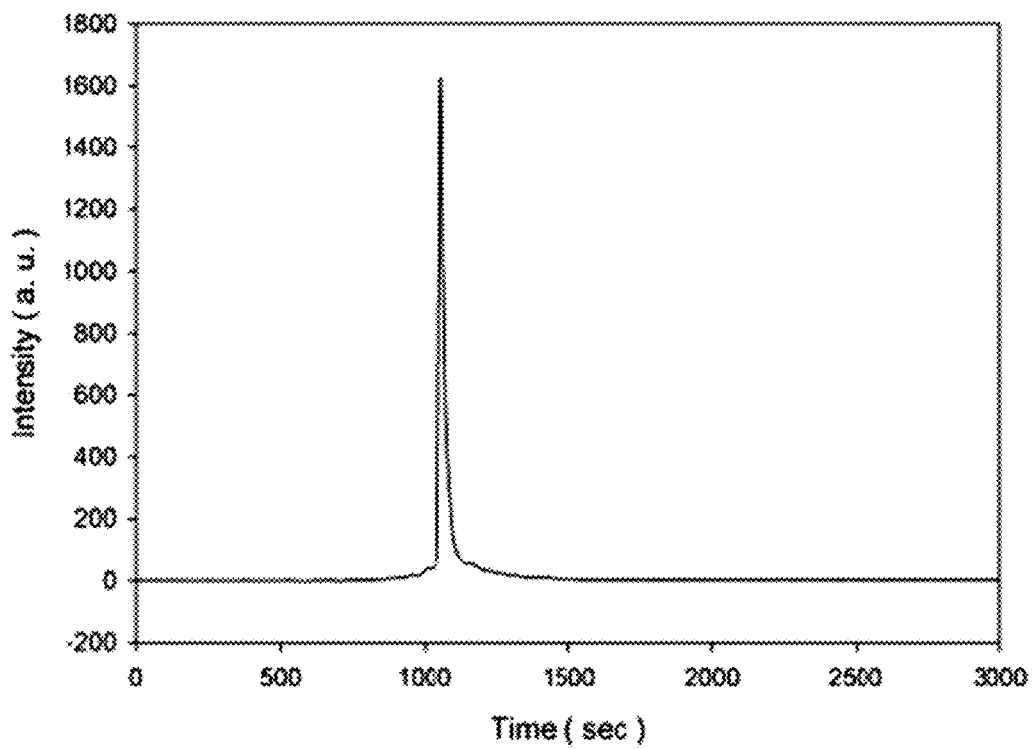
FIG. 4a: homochiral peptide complex prepared in Comparative Example 1.
Figure 4B:
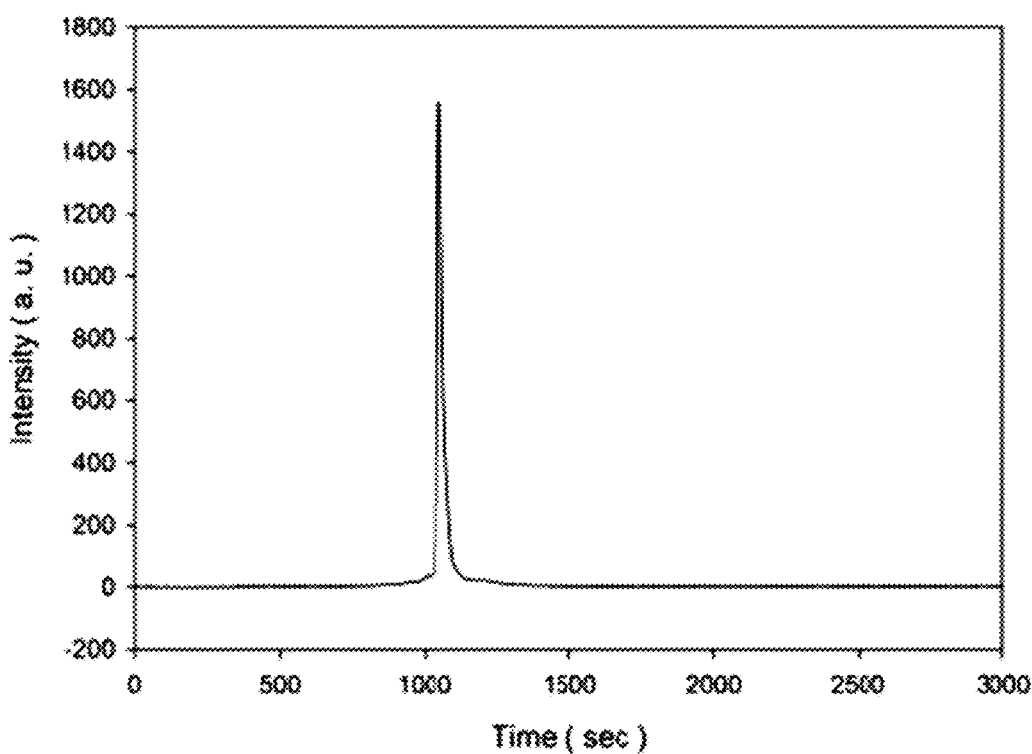
FIG. 4b: homochiral peptide complex prepared in Comparative Example 2.
Figure 4C:
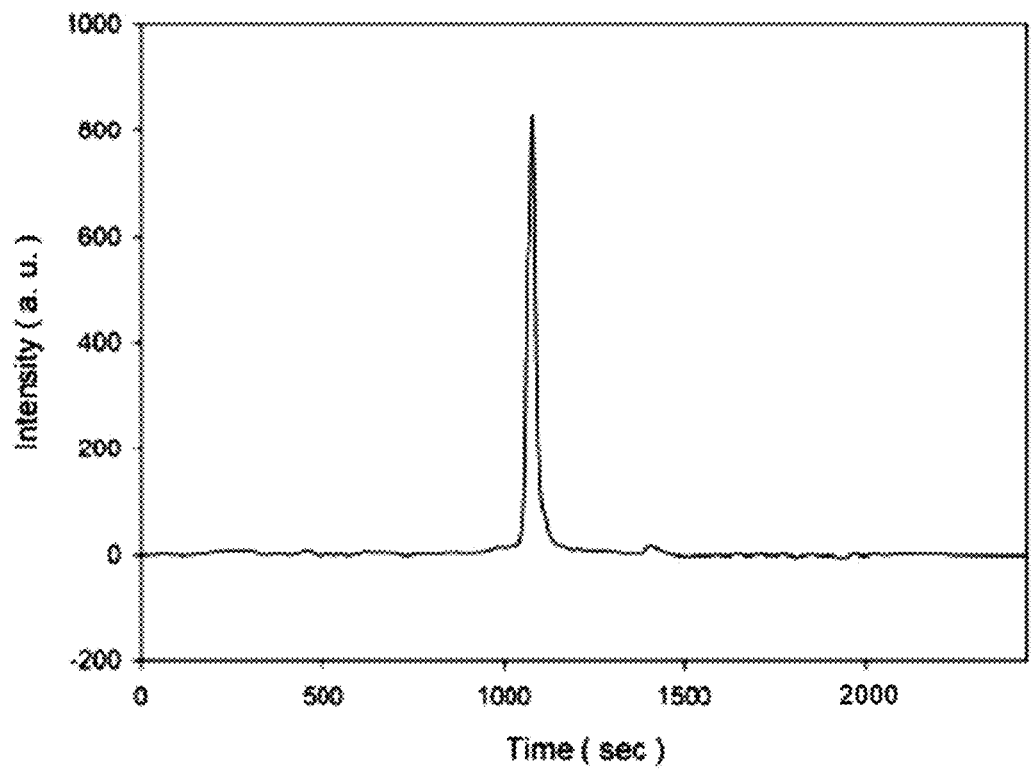
FIG. 4c: heterochiral peptide complex prepared in Example 1.

A PEGylated poly-Trp peptide ((D)Trp-(L)Trp-(D)Trp-(L)Tre-(D)Trp-(L)Trp) was synthesized according to the standard Fmoc protocol. Specifically, the peptide complex was synthesized by elongating on Rink amide MBHA resin LL as a solid support (resin substitution 0.36 mmol/g, synthesis scale 0.1 mmol). The rink amide resin was pre-swollen sufficiently with NMP for 30 minutes before the start of the synthesis. Every Fmoc group was deprotected by treating with 20% piperidine in NMP for 20 minutes. All the amino acid derivatives and Fmoc-PEG3-propionic acid (Fmoc-PEG3-PA) were preactivated using 4.5 equivalents (relative to the reaction scale) of HCTU and HOBt and 10 equivalents of diisopropylethylamine (DIPEA) in DMF for 5 minutes prior to the coupling reaction. Each coupling step proceeded for 30 minutes and the peptide complex was synthesized by sequentially treating with the amino acids and PEG3-PA or PEG10-PA. (PEG3-PA)$_3$ was designated as 'T' as shown in FIG. 2. After the final deprotection procedure, the peptide was separated from the peptidyl resin by treating with a cleavage cocktail mixture (trifluoroacetic acid (TFA):triisopropylsilane (TIS):water=92.5:2.5:2.5) for 4 hours at room temperature. The separated product was triturated with tert-butyl methyl ether (TBME) and purified by RP-HPLC chromatography using a C4 (Waters) column together with a 0.1% TFA-H$_2$O/CH$_3$CN (ACN) solvent system (FIG. 4*c*). The purified heterochiral peptide complex (T-(wW)$_3$) was confirmed by matrix-assisted laser desorption/ionization time-of-flight (MALDI-TOF) mass spectrometry. Its structure is shown in FIG. 2*c* and the analysis result is shown in FIG. 3*c*.

The heterochiral peptide complex (T-(wW)$_3$) was freeze-dried and stored until use.

Example 2. Synthesis of Heterochiral Peptide Complex, T-(Ww)$_3$

Figure 3D:
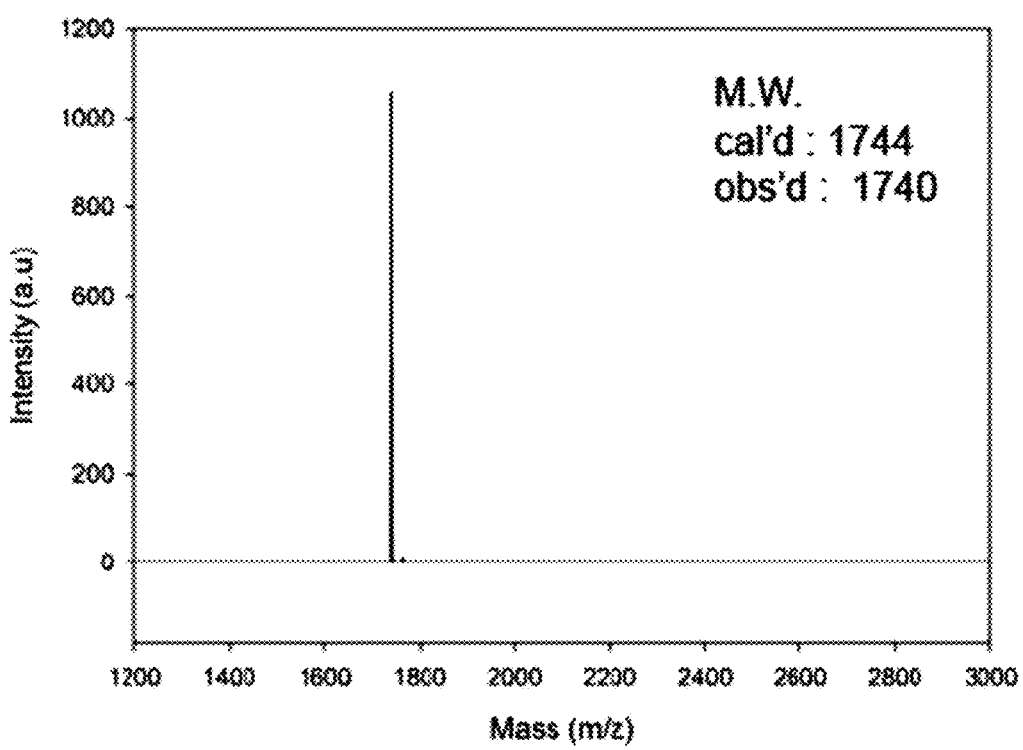
FIG. 3d: heterochiral peptide complex prepared in Example 2.
Figure 4D:
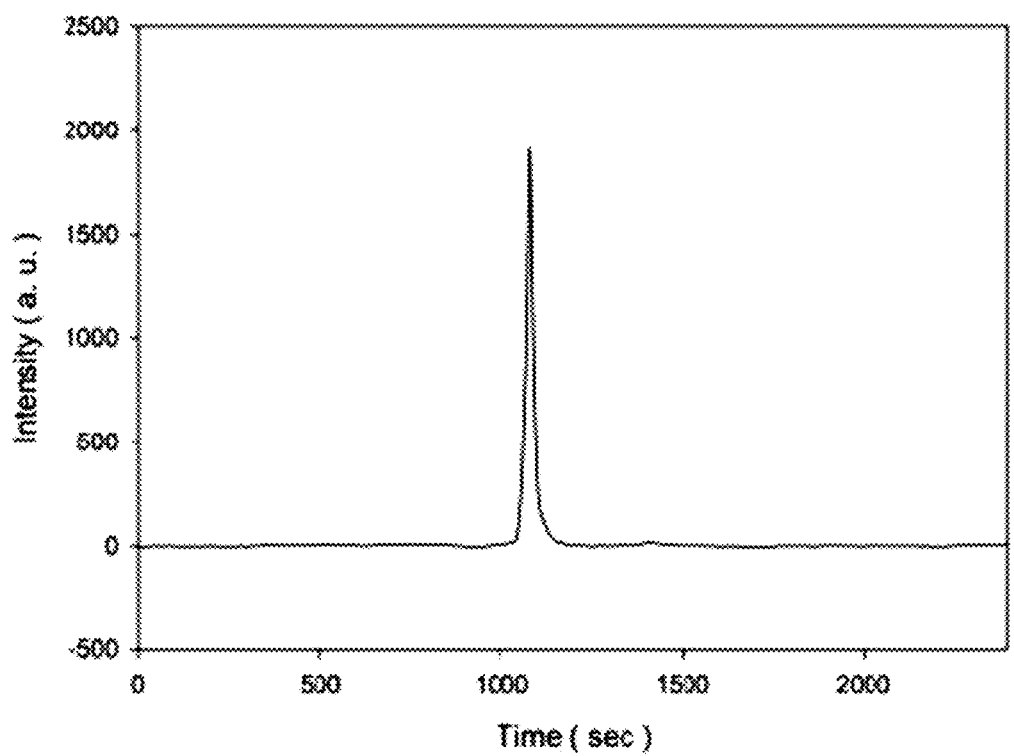
FIG. 4d: heterochiral peptide complex prepared in Example 2.

PEGylated (L)Trp-(D)Trp-(L)Trp-(D)Trp-(L)Trp-(D)Trp was prepared in the same manner as in Example 1. The prepared heterochiral peptide complex (T-(Ww)$_3$) was purified by RP-HPLC chromatography in the same manner as in Example 1 (FIG. 4*d*). The purified heterochiral peptide complex (T-(Ww)$_3$) was confirmed by matrix-assisted laser desorption/ionization time-of-flight (MALDI-TOF) mass spectrometry. Its structure is shown in FIG. 2*d* and the analysis result is shown in FIG. 3*d*.

The heterochiral peptide complex (T-(Ww)$_3$) was freeze-dried and stored until use.

Example 3. Synthesis of Heterochiral Peptide Complex, T-W-(wW)$_2$

Figure 3E:
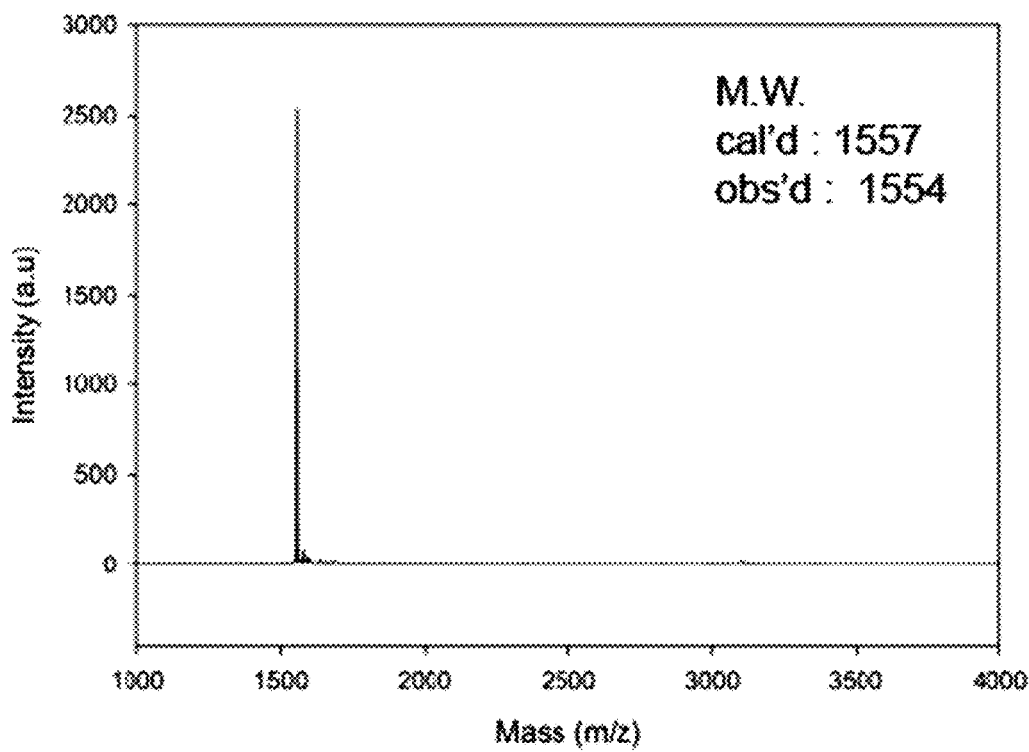
FIG. 3e: heterochiral peptide complex prepared in Example 3.
Figure 4E:
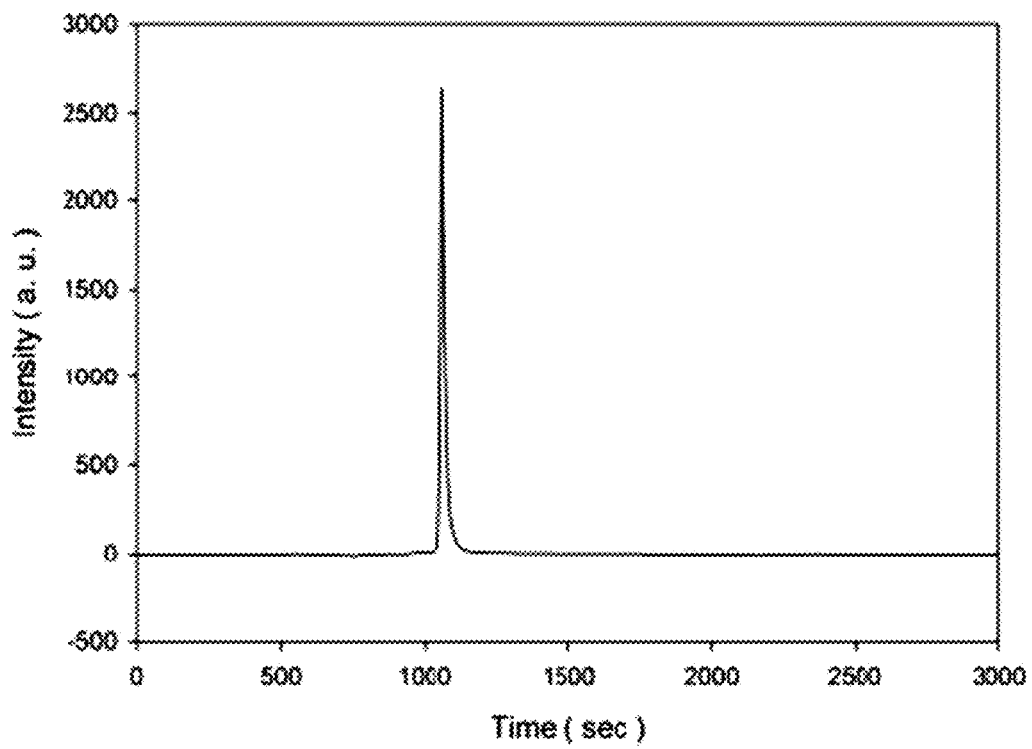
FIG. 4e: heterochiral peptide complex prepared in Example 3.

PEGylated (L)Trp-(D)Trp-(L)Trp-(D)Trp-(L)Trp was prepared in the same manner as in Example 1. The prepared heterochiral peptide complex (T-W-(wW)$_2$) was purified by RP-HPLC chromatography in the same manner as in Example 1 (FIG. 4e). The purified heterochiral peptide complex (T-W-(wW)$_2$) was confirmed by matrix-assisted laser desorption/ionization time-of-flight (MALDI-TOF) mass spectrometry. Its structure is shown in FIG. 2e and the analysis result is shown in FIG. 3e.

The heterochiral peptide complex (T-W-(wW)$_2$) was freeze-dried and stored until use.

Example 4. Synthesis of Heterochiral Peptide Complex, T-w-(Ww)$_2$

Figure 3F:
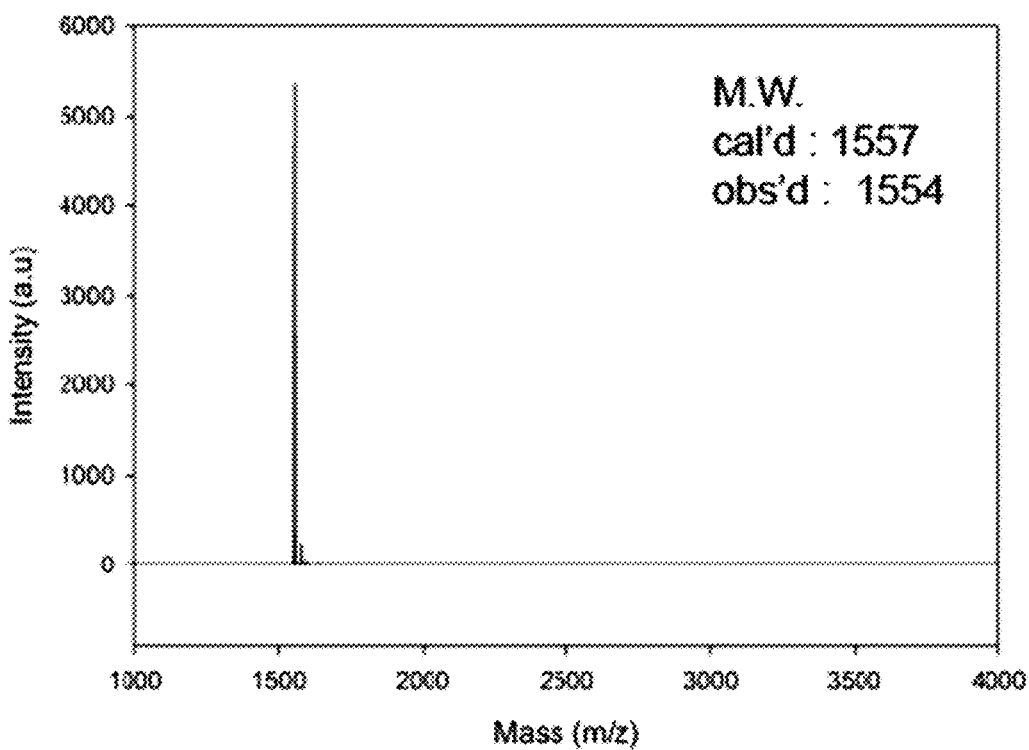
FIG. 3f: heterochiral peptide complex prepared in Example 4.
Figure 4F:
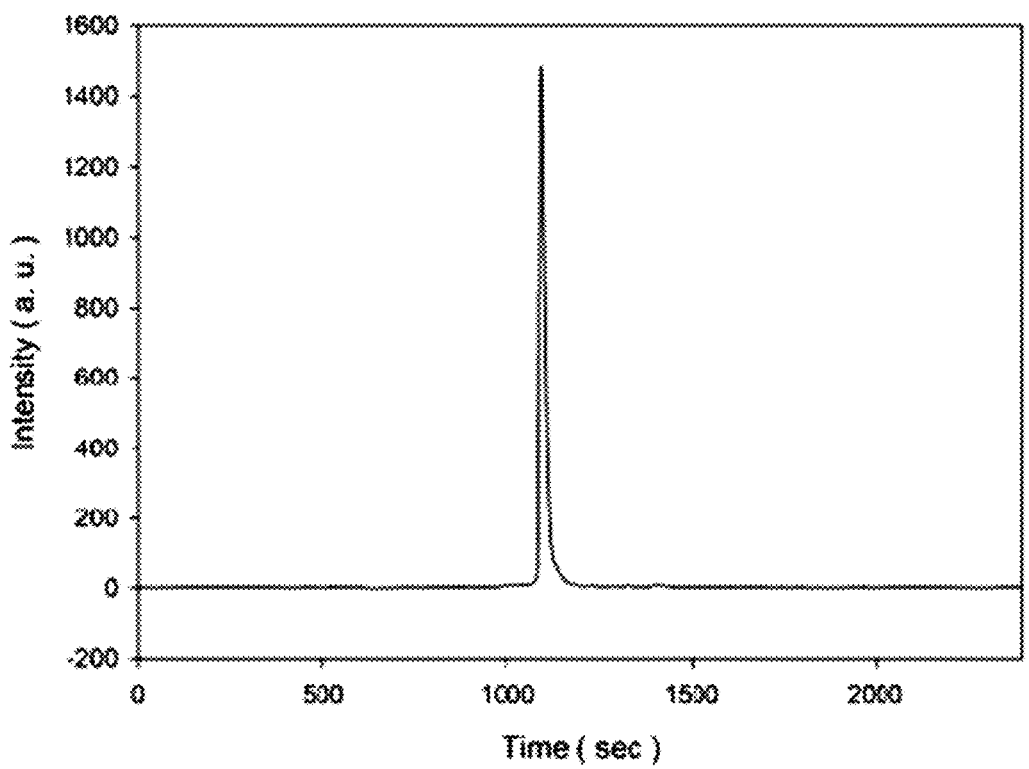
FIG. 4f: heterochiral peptide complex prepared in Example 4.

PEGylated (D)Trp-(L)Trp-(D)Trp-(L)Trp-(D)Trp was prepared in the same manner as in Example 1. The prepared heterochiral peptide complex (T-w-(Ww)$_2$) was purified by RP-HPLC chromatography in the same manner as in Example 1 (FIG. 4f). The purified heterochiral peptide complex (T-w-(Ww)$_2$) was confirmed by matrix-assisted laser desorption/ionization time-of-flight (MALDI-TOF) mass spectrometry. Its structure is shown in FIG. 2f and the analysis result is shown in FIG. 3f.

The heterochiral peptide complex (T-w-(Ww)$_2$) was freeze-dried and stored until use.

Example 5. Synthesis of Heterochiral Peptide Complex, T-(VV)$_3$

Figure 22A:
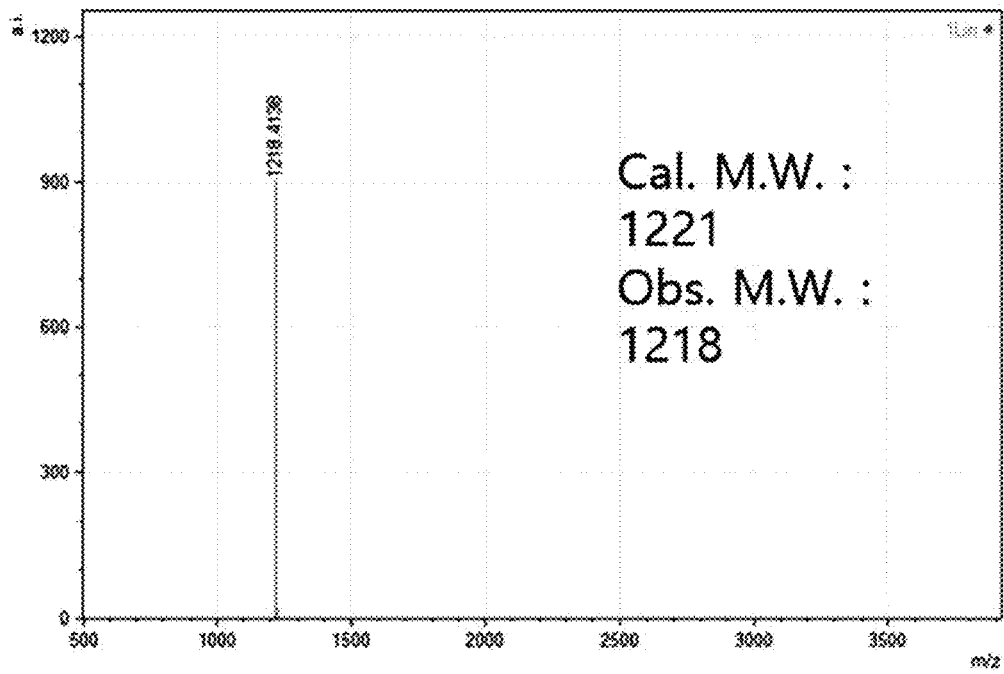
FIG. 22a: homochiral peptide complex prepared in Comparative Example 3.
Figure 22B:
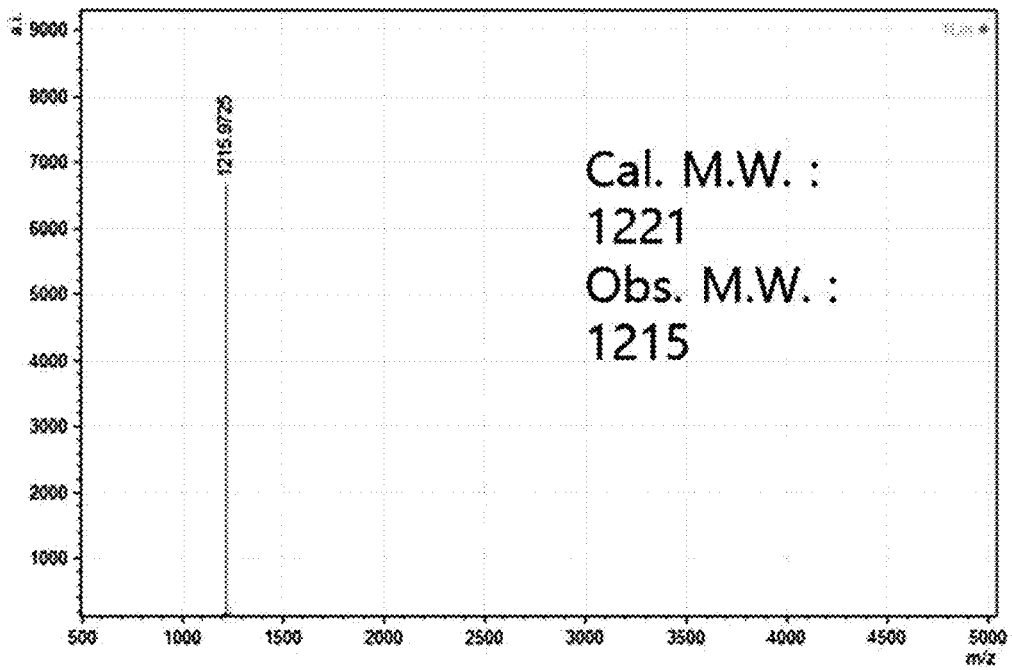
FIG. 22b: homochiral peptide complex prepared in Comparative Example 4.
Figure 22C:
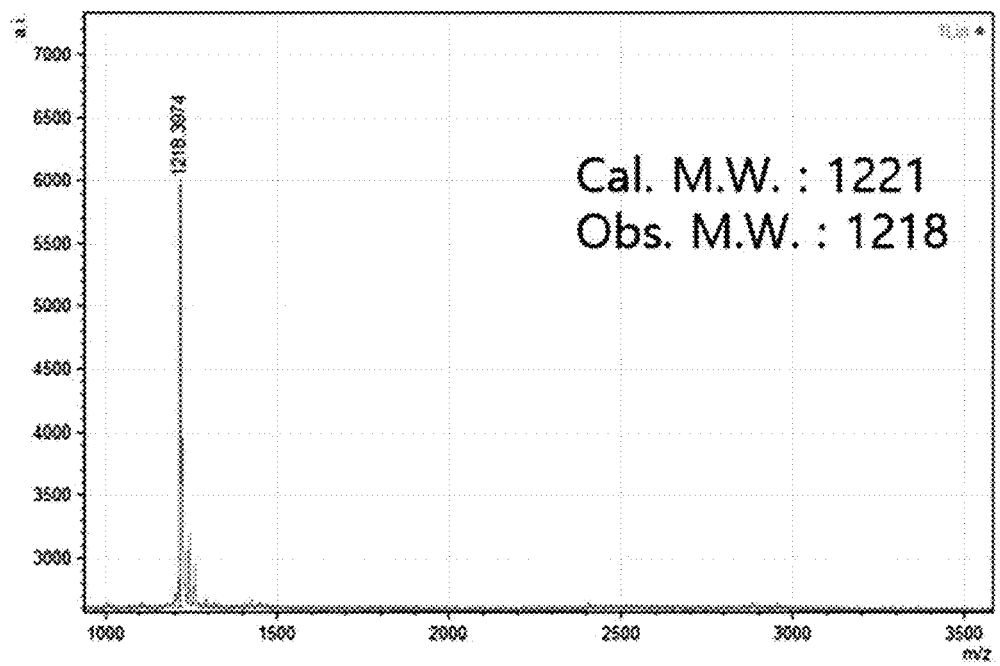
FIG. 22c: heterochiral peptide complex prepared in Example 5.

PEGylated (D)Val-(L)Val-(D)Val-(L)Val-(D)Val-(L)Val was prepared in the same manner as in Example 1. The prepared heterochiral peptide complex (T-(VV)$_3$) was purified by RP-HPLC chromatography in the same manner as in Example 1. The purified heterochiral peptide complex (T-(VV)$_3$) was confirmed by matrix-assisted laser desorption/ionization time-of-flight (MALDI-TOF) mass spectrometry. The result is shown in FIG. 22c.

The heterochiral peptide complex (T-(VV)$_3$) was freeze-dried and stored until use.

Example 6. Synthesis of Heterochiral Peptide Complex, T-(fF)$_3$

Figure 22D:
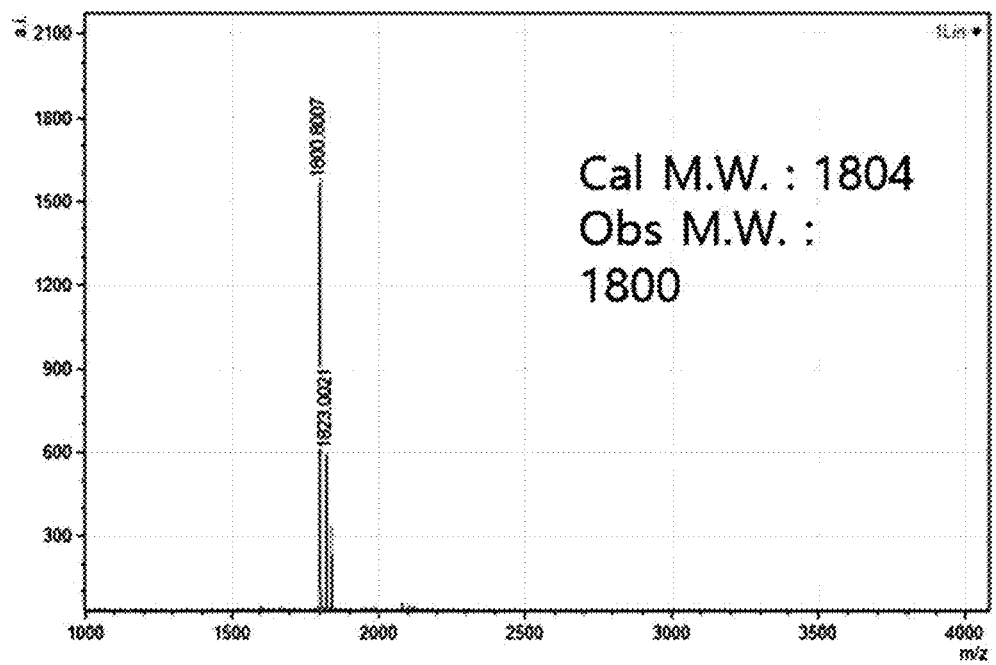
FIG. 22d: heterochiral peptide complex prepared in Example 6.

PEGylated (D)Phe-(L)Phe-(D)Phe-(L)Phe-(D)Phe-(L)Phe was prepared in the same manner as in Example 1. The prepared heterochiral peptide complex (T-(fF)$_3$) was purified by RP-HPLC chromatography in the same manner as in Example 1. The purified heterochiral peptide complex (T-(fF)$_3$) was confirmed by matrix-assisted laser desorption/ionization time-of-flight (MALDI-TOF) mass spectrometry. The result is shown in FIG. 22d.

The heterochiral peptide complex (T-(fF)$_3$) was freeze-dried and stored until use.

Example 7. Synthesis of Heterochiral Peptide Complex, T-(fF)$_4$

Figure 22E:
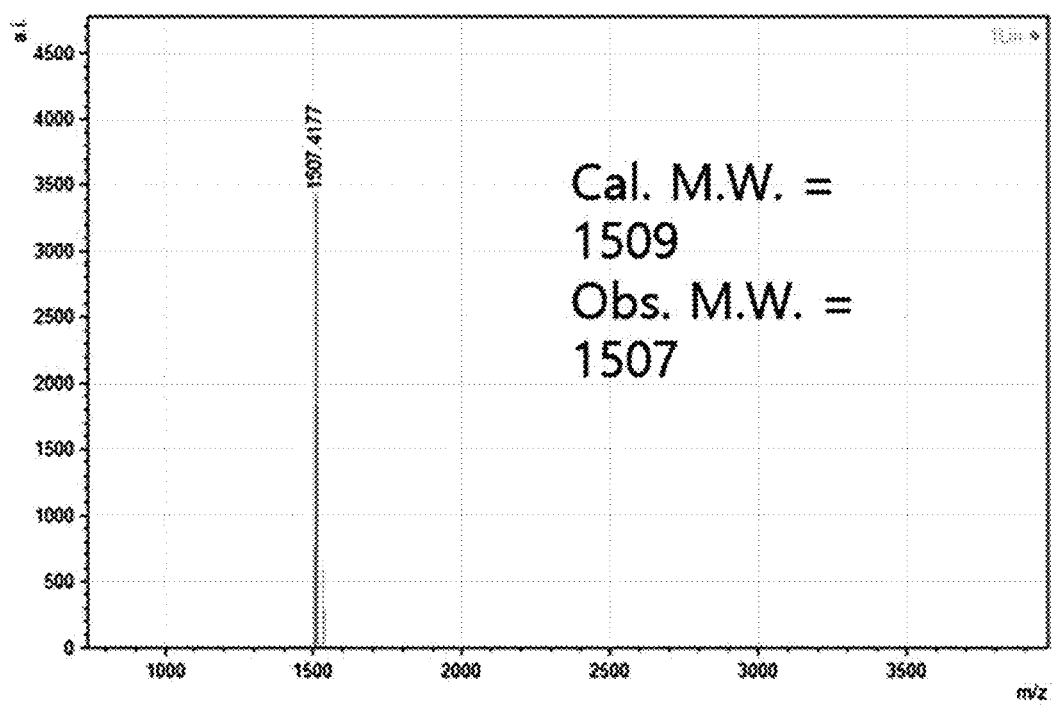
FIG. 22e: heterochiral peptide complex prepared in Example 7.

PEGylated (D)Phe-(L)Phe-(D)Phe-(L)Phe-(D)Phe-(L)Phe-(D)Phe-(L)Phe was prepared in the same manner as in Example 1. The prepared heterochiral peptide complex (T-(fF)$_4$) was purified by RP-HPLC chromatography in the same manner as in Example 1. The purified heterochiral peptide complex (T-(fF)$_4$) was confirmed by matrix-assisted laser desorption/ionization time-of-flight (MALDI-TOF) mass spectrometry. The result is shown in FIG. 22e.

The heterochiral peptide complex (T-(fF)$_4$) was freeze-dried and stored until use.

Example 8. Synthesis of Heterochiral Peptide Complex, T-w-(W)$_2$-(w)$_2$-W

Figure 23A:
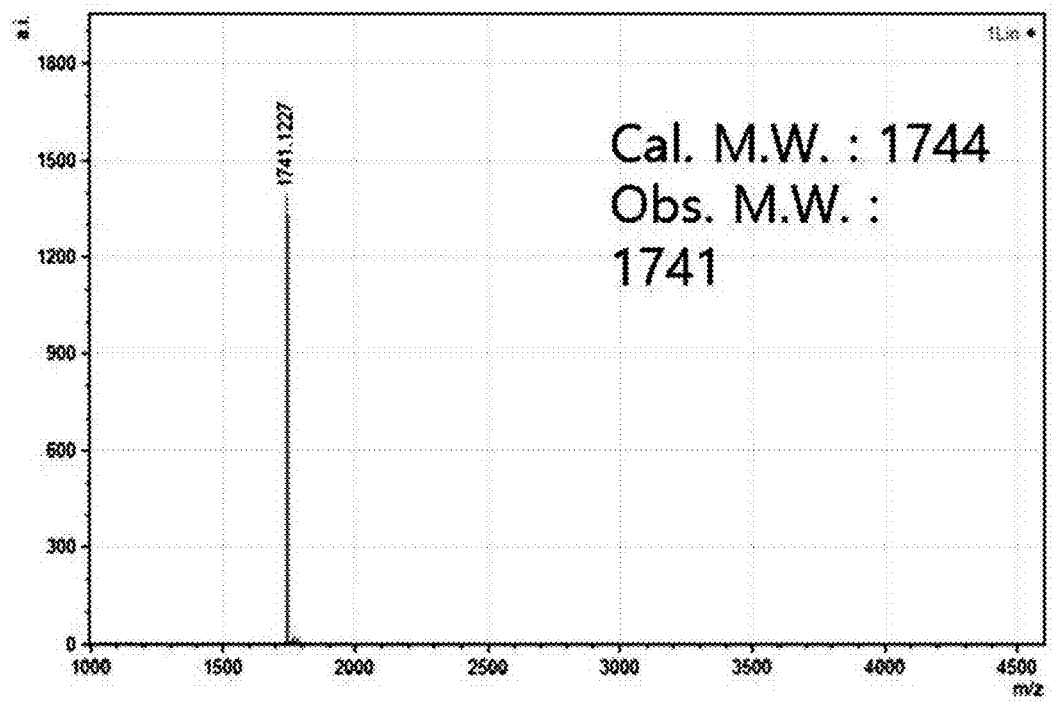
FIG. 23a: heterochiral peptide complex prepared in Example 8.

PEGylated (D)Trp-(L)Trp-(L)Trp-(D)Trp-(D)Trp-(L)Trp was prepared in the same manner as in Example 1. The prepared heterochiral peptide complex (T-w-(W)$_2$-(w)$_2$-W) was purified by RP-HPLC chromatography in the same manner as in Example 1. The purified heterochiral peptide complex (T-w-(W)$_2$-(w)$_2$-W) was confirmed by matrix-assisted laser desorption/ionization time-of-flight (MALDI-TOF) mass spectrometry. The result is shown in FIG. 23a.

The heterochiral peptide complex (T-w-(W)$_2$-(w)$_2$-W) was freeze-dried and stored until use.

Example 9. Synthesis of Heterochiral Peptide Complex, T-w$_3$-W$_3$

Figure 23B:
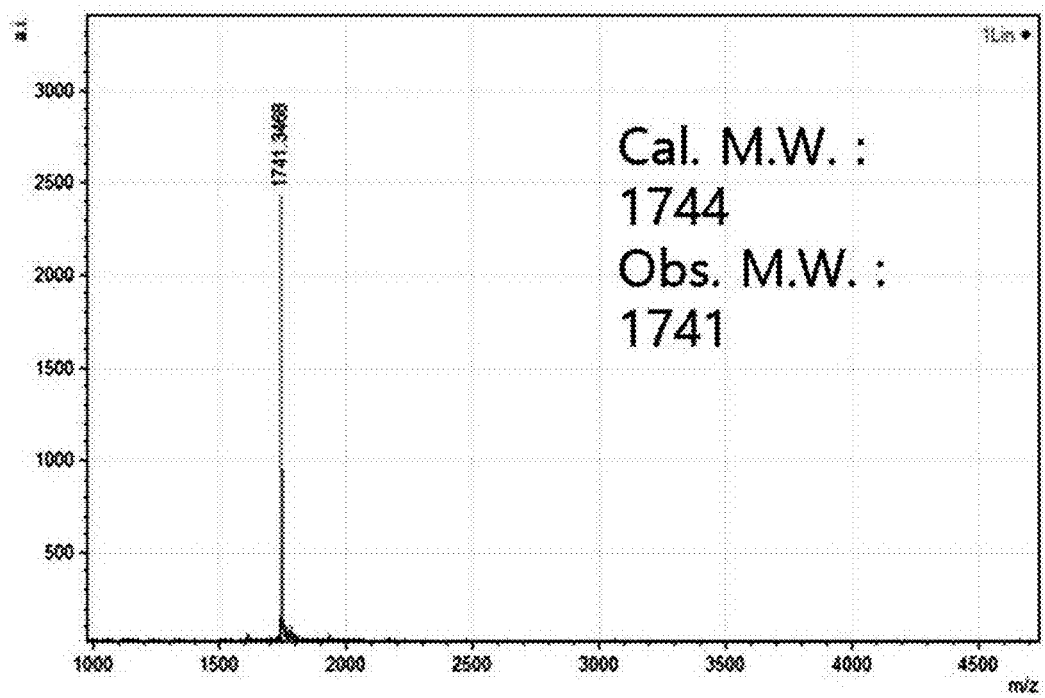
FIG. 23b: heterochiral peptide complex prepared in Example 9.

PEGylated (D)Trp-(D)Trp-(D)Trp-(L)Trp-(L)Trp-(L)Trp was prepared in the same manner as in Example 1. The prepared heterochiral peptide complex (T-w$_3$-W$_3$) was purified by RP-HPLC chromatography in the same manner as in Example 1. The purified heterochiral peptide complex (T-w$_3$-W$_3$) was confirmed by matrix-assisted laser desorption/ionization time-of-flight (MALDI-TOF) mass spectrometry. The result is shown in FIG. 23b.

The heterochiral peptide complex (T-w$_3$-W$_3$) was freeze-dried and stored until use.

Example 10. Synthesis of Heterochiral Peptide Complex, T-(wW)$_2$-w$_2$

Figure 23C:
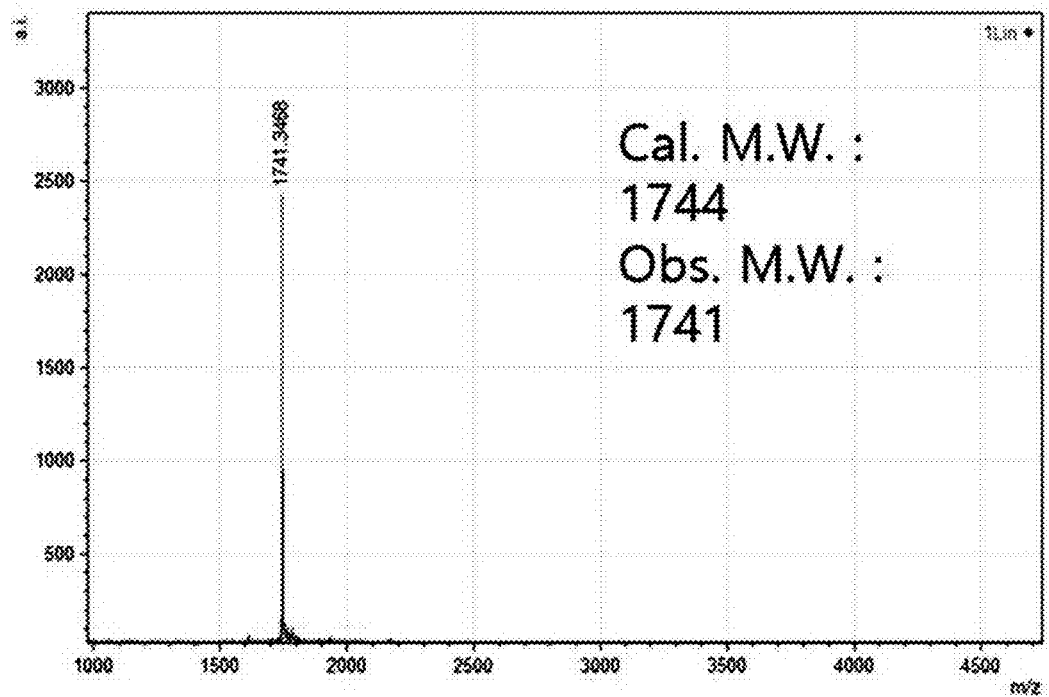
FIG. 23c: heterochiral peptide complex prepared in Example 10.

PEGylated (D)Trp-(L)Trp-(D)Trp-(L)Trp-(D)Trp-(D)Trp was prepared in the same manner as in Example 1. The prepared heterochiral peptide complex (T-(wW)$_2$-w$_2$) was purified by RP-HPLC chromatography in the same manner as in Example 1. The purified heterochiral peptide complex (T-(wW)$_2$-w$_2$) was confirmed by matrix-assisted laser desorption/ionization time-of-flight (MALDI-TOF) mass spectrometry. The result is shown in FIG. 23c.

The heterochiral peptide complex (T-(wW)$_2$-w$_2$) was freeze-dried and stored until use.

Example 11. Synthesis of Heterochiral Peptide Complex, T-W$_2$-(wW)$_2$

Figure 23D:
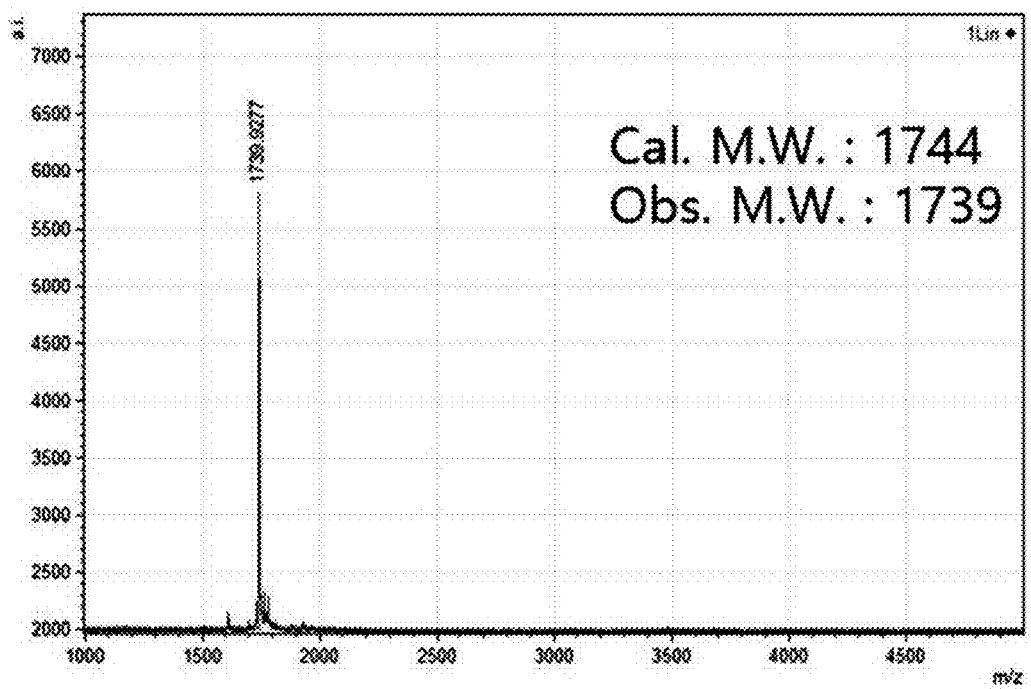
FIG. 23d: heterochiral peptide complex prepared in Example 11.

PEGylated (L)Trp-(L)Trp-(D)Trp-(L)Trp-(D)Trp-(L)Trp was prepared in the same manner as in Example 1. The prepared heterochiral peptide complex (T-W$_2$-(wW)$_2$) was purified by RP-HPLC chromatography in the same manner as in Example 1. The purified heterochiral peptide complex (T-W$_2$-(wW)$_2$) was confirmed by matrix-assisted laser desorption/ionization time-of-flight (MALDI-TOF) mass spectrometry. The result is shown in FIG. 23d.

The heterochiral peptide complex (T-W$_2$-(wW)$_2$) was freeze-dried and stored until use.

Figure 24A:
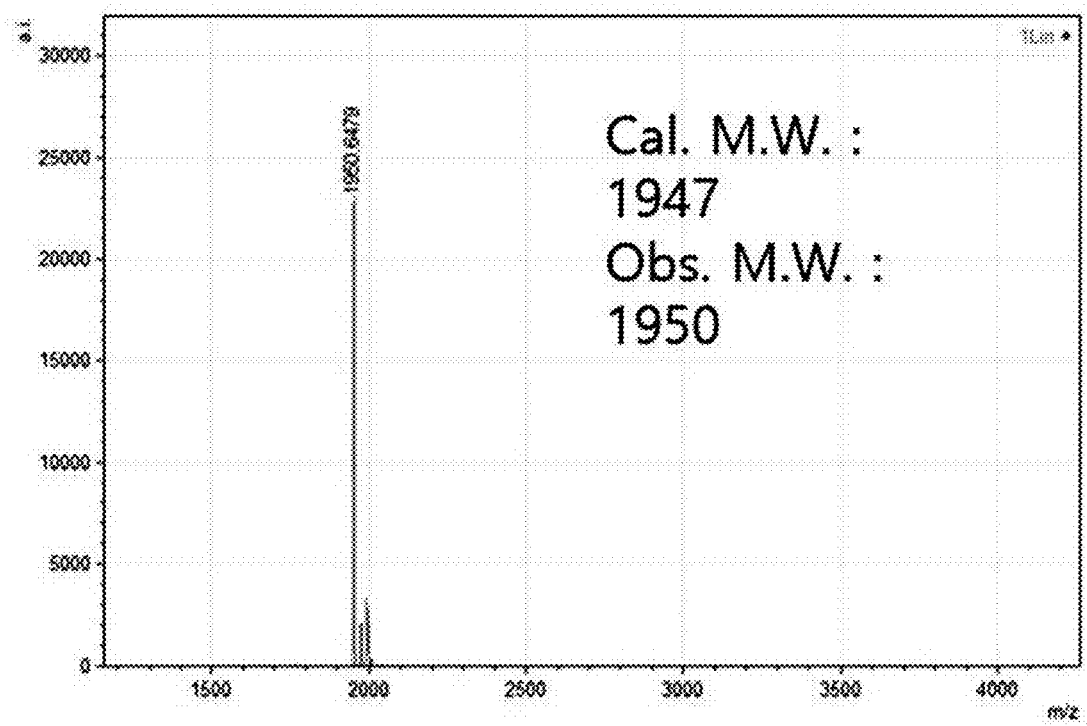
FIG. 24a: heterochiral peptide complex prepared in Example 12.

Example 12. Synthesis of Heterochiral Peptide Complex, (PEG3-PA)$_4$-(wW)$_3$ PEGylated (D)Trp-(L)Trp-(D)Trp-(L)Trp-(D)Trp-(L)Trp was prepared in the same manner as in Example 1. The prepared heterochiral peptide complex ((PEG3-PA)$_4$-(wW)$_3$) was purified by RP-HPLC chromatography in the same manner as in Example 1. The purified heterochiral peptide complex ((PEG3-PA)$_4$-(wW)$_3$) was confirmed by matrix-assisted laser desorption/ionization time-of-flight (MALDI-TOF) mass spectrometry. The result is shown in FIG. 24a.

The heterochiral peptide complex ((PEG3-PA)$_4$-(wW)$_3$) was freeze-dried and stored until use.

Figure 24B:
FIG. 24b: heterochiral peptide complex prepared in Example 13.
Figure 24B:
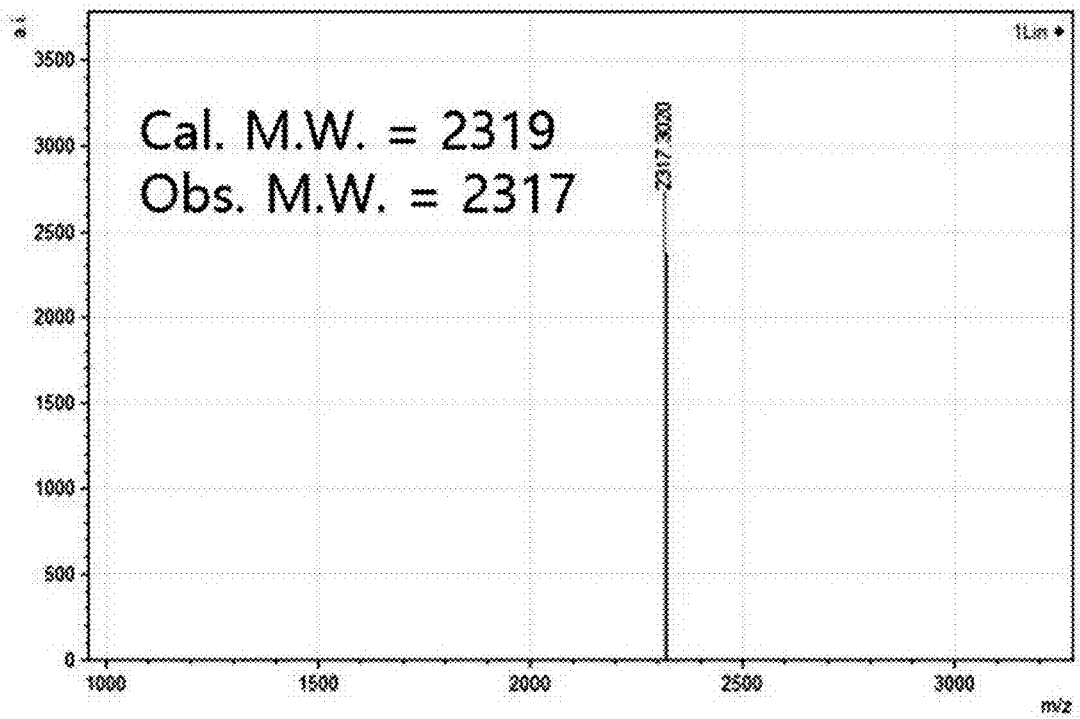

Example 13. Synthesis of Heterochiral Peptide Complex, (PEG3-PA)$_4$-(wW)$_4$ PEGylated (D)Trp-(L)Trp-(D)Trp-(L)Trp-(D)Trp-(L)Trp-(D)Trp-(L)Trp was prepared in the same manner as in Example 1. The prepared heterochiral peptide complex ((PEG3-PA)$_4$-(wW)$_4$) was purified by RP-HPLC chromatography in the same manner as in Example 1. The purified heterochiral peptide complex ((PEG3-PA)$_4$-(wW)$_4$) was confirmed by matrix-assisted laser desorption/ionization time-of-flight (MALDI-TOF) mass spectrometry. The result is shown in FIG. 24b.

The heterochiral peptide complex (T$_4$-(wW)$_4$) was freeze-dried and stored until use.

Figure 24C:
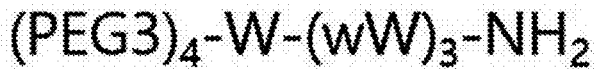
FIG. 24c: heterochiral peptide complex prepared in Example 14.
Figure 24C:
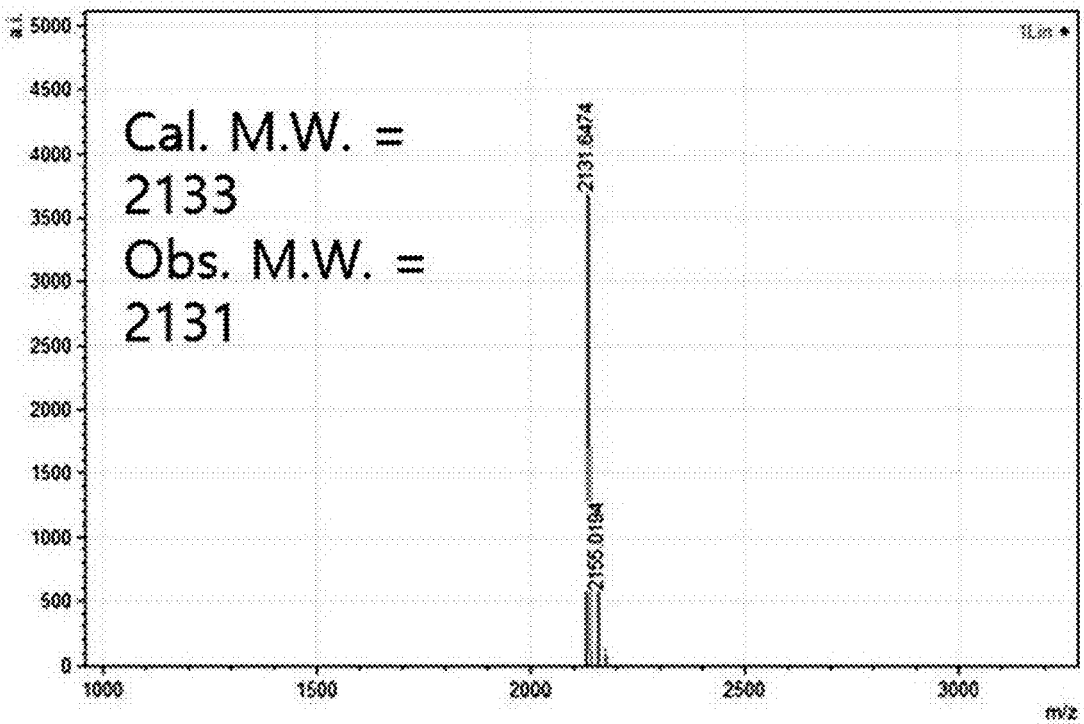

Example 14. Synthesis of Heterochiral Peptide Complex, (PEG3-PA)$_4$-W-(wW)$_3$ PEGylated (L)Trp-(D)Trp-(L)Trp-(D)Trp-(L)Trp-(D)Trp-(L)Trp was prepared in the same manner as in Example 1. The prepared heterochiral peptide complex ((PEG3-PA)$_4$-W-(wW)$_4$) was purified by RP-HPLC chromatography in the same manner as in Example 1. The purified heterochiral peptide complex ((PEG3-PA)$_4$-W-(wW)$_4$) was confirmed by matrix-assisted laser desorption/ionization time-of-flight (MALDI-TOF) mass spectrometry. The result is shown in FIG. 24c.

The heterochiral peptide complex ((PEG3-PA)$_4$-W-(wW)$_4$) was freeze-dried and stored until use.

Figure 24D:
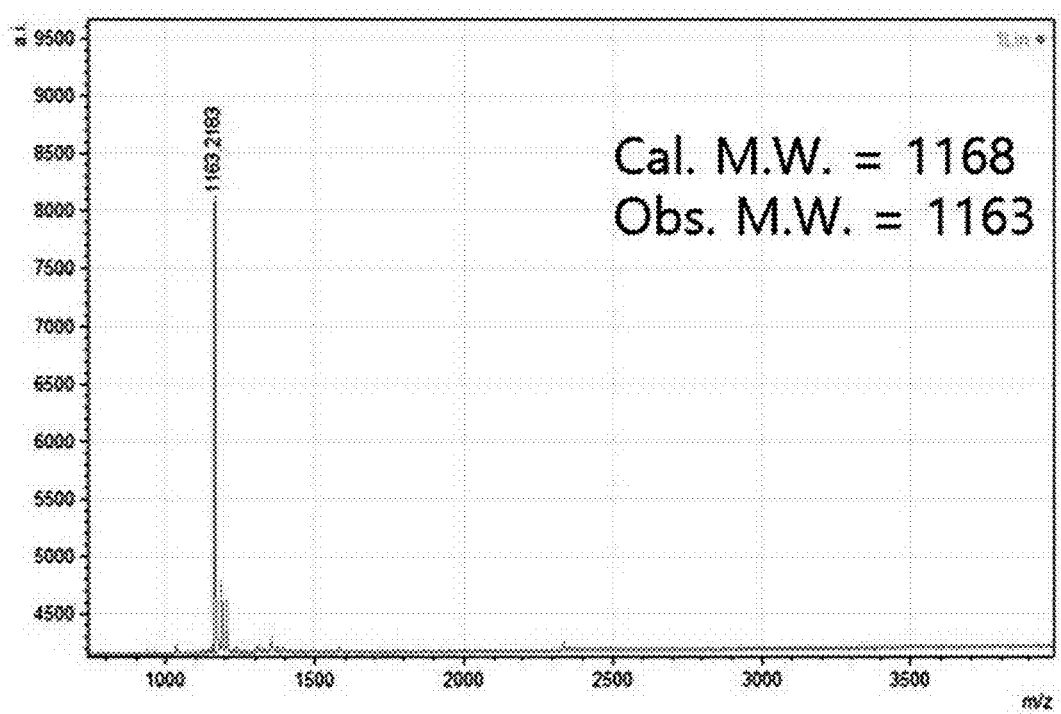
FIG. 24d: heterochiral peptide complex prepared in Example 15.

Example 15. Synthesis of Heterochiral Peptide Complex, (PEG3-PA)$_2$-(wW)$_2$ PEGylated (D)Trp-(L)Trp-(D)Trp-(L)Trp was prepared in the same manner as in Example 1. The prepared heterochiral peptide complex ((PEG3-PA)$_2$-(wW)$_2$) was purified by RP-HPLC chromatography in the same manner as in Example 1. The purified heterochiral peptide complex ((PEG3-PA)$_2$-(wW)$_2$) was confirmed by matrix-assisted laser desorption/ionization time-of-flight (MALDI-TOF) mass spectrometry. The result is shown in FIG. 24d.

The heterochiral peptide complex ((PEG3-PA)$_2$-(wW)$_2$) was freeze-dried and stored until use.

Figure 24E:
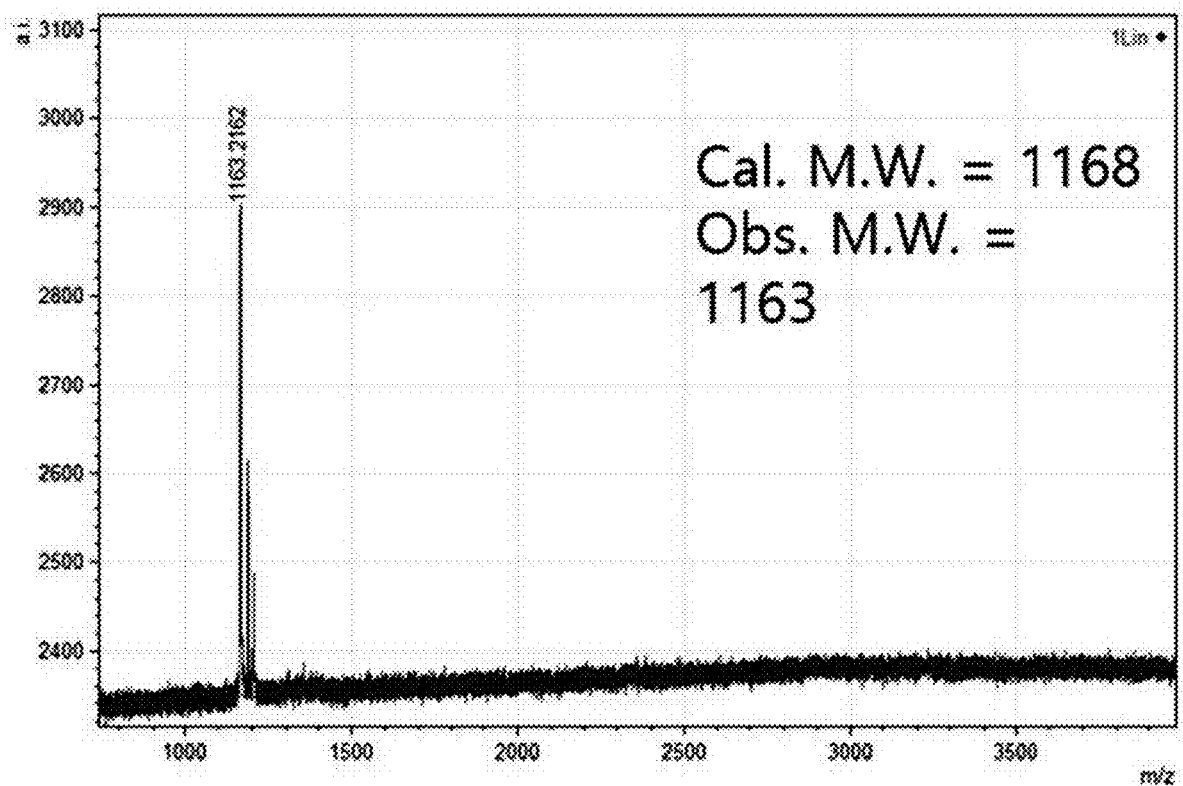
FIG. 24e: heterochiral peptide complex prepared in Example 16.

Example 16. Synthesis of Heterochiral Peptide Complex, (PEG3-PA)$_2$-w$_2$-W$_2$ PEGylated (D)Trp-(D)Trp-(L)Trp-(L)Trp was prepared in the same manner as in Example 1. The prepared heterochiral peptide complex ((PEG3-PA)$_2$-w$_2$-W$_2$) was purified by RP-HPLC chromatography in the same manner as in Example 1. The purified heterochiral peptide complex ((PEG3-PA)$_2$-w$_2$-W$_2$) was confirmed by matrix-assisted laser desorption/ionization time-of-flight (MALDI-TOF) mass spectrometry. The result is shown in FIG. 24e.

The heterochiral peptide complex ((PEG3-PA)$_2$-w$_2$-W$_2$) was freeze-dried and stored until use.

Figure 25A:
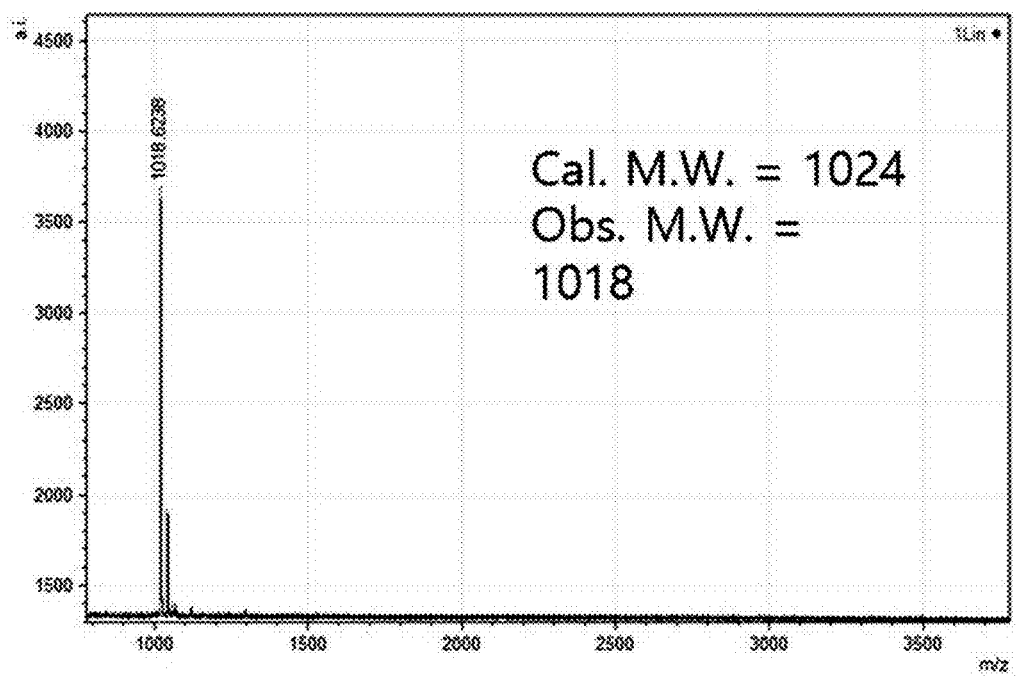
FIG. 25a: heterochiral peptide complex prepared in Example 17.

Example 17. Synthesis of Heterochiral Peptide Complex, (PEG10-PA)-V-(VV)$_2$ PEGylated (L)Val-(D)Val-(L)Val-(D)Val-(L)Val was prepared in the same manner as in Example 1. The prepared heterochiral peptide complex ((PEG10-PA)-V-(VV)$_2$) was purified by RP-HPLC chromatography in the same manner as in Example 1. The purified heterochiral peptide complex ((PEG10-PA)-V-(vV)$_2$) was confirmed by matrix-assisted laser desorption/ionization time-of-flight (MALDI-TOF) mass spectrometry. The result is shown in FIG. 25a.

The heterochiral peptide complex ((PEG10-PA)-V-(vV)$_2$) was freeze-dried and stored until use.

Figure 25B:
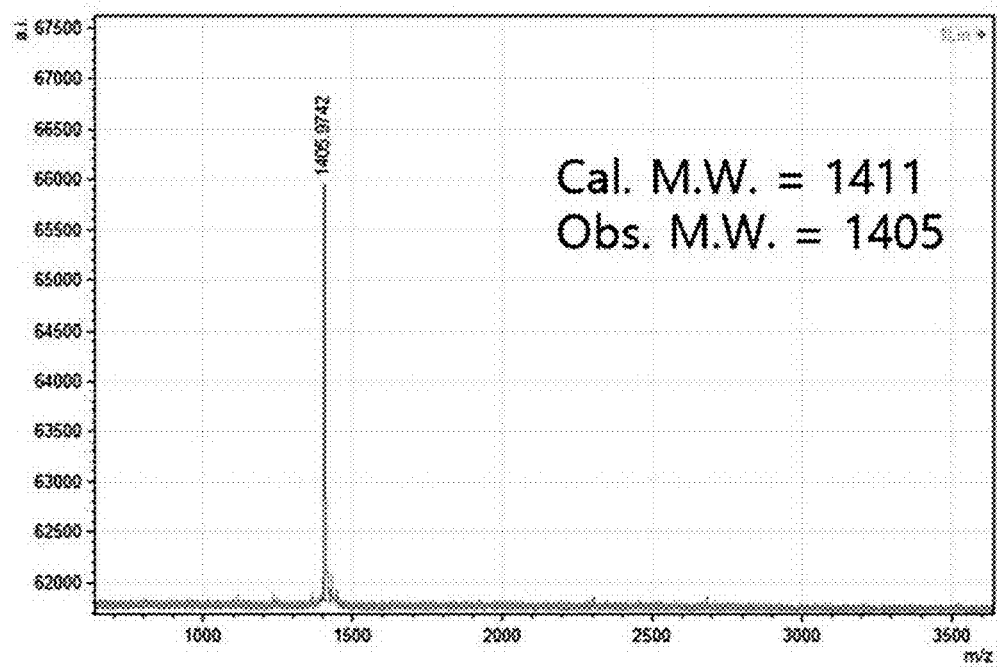
FIG. 25b: heterochiral peptide complex prepared in Example 18.

Example 18. Synthesis of Heterochiral Peptide Complex, (PEG10-PA)-f$_3$-F$_3$ PEGylated (D)Phe-(D)Phe-(D)Phe-(L)Phe-(L)Phe-(L)Phe was prepared in the same manner as in Example 1. The prepared heterochiral peptide complex ((PEG10-PA)-f$_3$-F$_3$) was purified by RP-HPLC chromatography in the same manner as in Example 1. The purified heterochiral peptide complex ((PEG10-PA)-f$_3$-F$_3$) was confirmed by matrix-assisted laser desorption/ionization time-of-flight (MALDI-TOF) mass spectrometry. The result is shown in FIG. 25b.

The heterochiral peptide complex ((PEG10-PA)-f$_3$-F$_3$) was freeze-dried and stored until use.

Figure 25C:
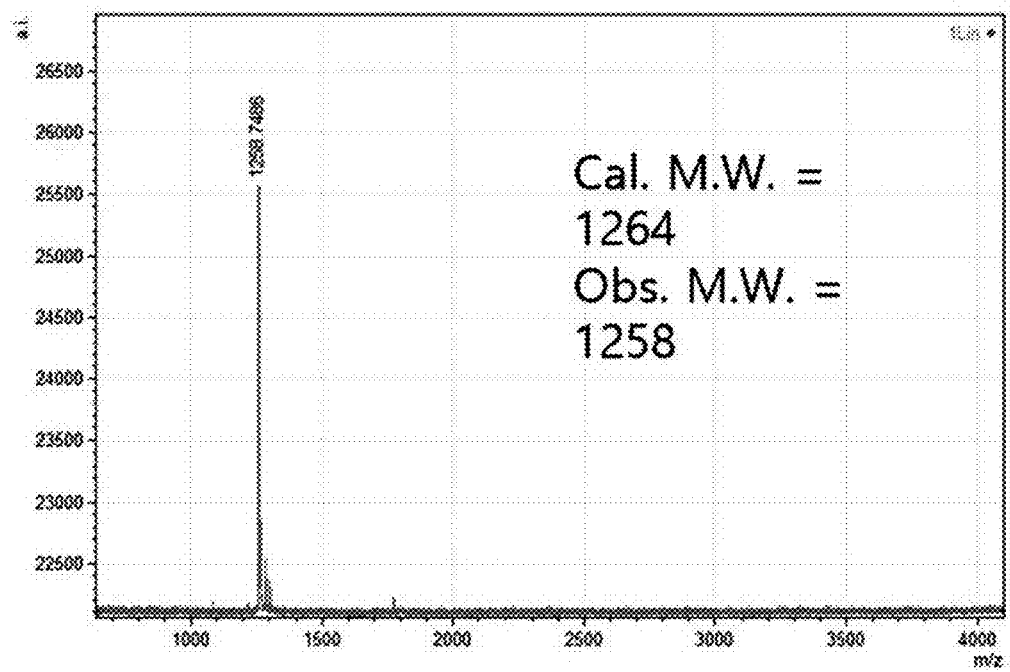
FIG. 25c: heterochiral peptide complex prepared in Example 19.

Example 19. Synthesis of Heterochiral Peptide Complex, (PEG10-PA)-F-(fF)$_2$ PEGylated (L)Phe-(D)Phe-(L)Phe-(D)Phe-(L)Phe-(D)Phe-(L)Phe was prepared in the same manner as in Example 1. The prepared heterochiral peptide complex ((PEG10-PA)-F-(fF)$_2$) was purified by RP-HPLC chromatography in the same manner as in Example 1. The purified heterochiral peptide complex ((PEG10-PA)-F-(fF)$_2$) was confirmed by matrix-assisted laser desorption/ionization time-of-flight (MALDI-TOF) mass spectrometry. The result is shown in FIG. 25c.

The heterochiral peptide complex ((PEG10-PA)-F-(fF)$_2$) was freeze-dried and stored until use.

Example 20. Synthesis of Heterochiral Peptide Complex, (PEG10-PA)-(fF)$_2$

Figure 25D:
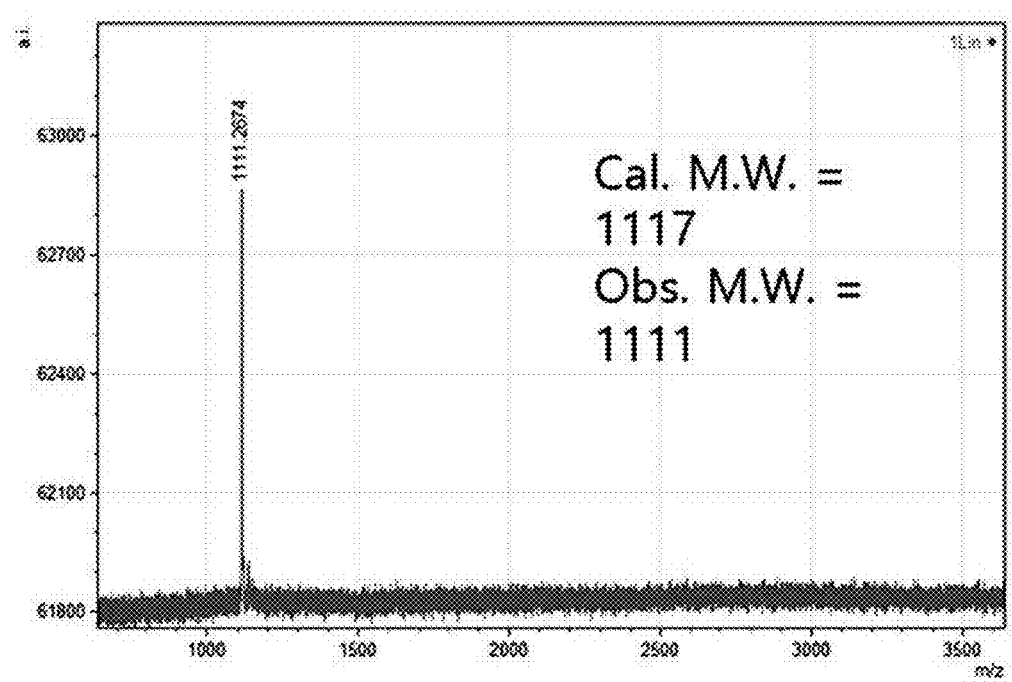
FIG. 25d: heterochiral peptide complex prepared in Example 20.

PEGylated (D)Phe-(L)Phe-(D)Phe-(L)Phe was prepared in the same manner as in Example 1. The prepared heterochiral peptide complex ((PEG10-PA)-(fF)$_2$) was purified by RP-HPLC chromatography in the same manner as in Example 1. The purified heterochiral peptide complex ((PEG10-PA)-(fF)$_2$) was confirmed by matrix-assisted laser desorption/ionization time-of-flight (MALDI-TOF) mass spectrometry. The result is shown in FIG. 25d.

The heterochiral peptide complex ((PEG10-PA)-(fF)$_2$) was freeze-dried and stored until use.

Comparative Example 1. Preparation of Homochiral Peptide Complex, T-W$_6$

PEGylated (L)Trp-(L)Trp-(L)Trp-(L)Trp-(L)Trp-(L)Trp (Comparative Example 1) was prepared in the same manner as in Example 1. The prepared homochiral peptide complex (T-W$_6$) was purified by RP-HPLC chromatography in the same manner as in Example 1 (FIG. 4a). The purified homochiral peptide complex (T-W$_6$) was confirmed by matrix-assisted laser desorption/ionization time-of-flight (MALDI-TOF) mass spectrometry. Its structure is shown in FIG. 2a and the analysis result is shown in FIG. 3a.

The homochiral peptide complex (T-W$_6$) was freeze-dried and stored until use.

Comparative Example 2. Preparation of Homochiral Peptide Complex, T-w$_6$

PEGylated (D)Trp-(D)Trp-(D)Trp-(D)Trp-(D)Trp-(D)Trp (Comparative Example 2) was prepared in the same manner as in Example 1. The prepared homochiral peptide complex (T-w$_6$) was purified by RP-HPLC chromatography in the same manner as in Example 1 (FIG. 4b). The purified homochiral peptide complex (T-w$_6$) was confirmed by matrix-assisted laser desorption/ionization time-of-flight (MALDI-TOF) mass spectrometry. Its structure is shown in FIG. 2b and the analysis result is shown in FIG. 3b.

The homochiral peptide complex (T-w$_6$) was freeze-dried and stored until use.

Comparative Example 3. Preparation of Homochiral Peptide Complex, T-v$_6$

PEGylated (D)Val-(D)Val-(D)Val-(D)Val-(D)Val-(D)Val (Comparative Example 3) was prepared in the same manner as in Example 1. The prepared homochiral peptide complex (T-v$_6$) was purified by RP-HPLC chromatography in the same manner as in Example 1. The purified homochiral peptide complex (T-w$_6$) was confirmed by matrix-assisted laser desorption/ionization time-of-flight (MALDI-TOF) mass spectrometry. The result is shown in FIG. 22a.

The homochiral peptide complex (T-v$_6$) was freeze-dried and stored until use.

Comparative Example 4. Preparation of Homochiral Peptide Complex, T-V6

PEGylated (L)Val-(L)Val-(L)Val-(L)Val-(L)Val-(L)Val (Comparative Example 4) was prepared in the same manner as in Example 1. The prepared homochiral peptide complex (T-V6) was purified by RP-HPLC chromatography in the same manner as in Example 1. The purified homochiral peptide complex (T-V6) was confirmed by matrix-assisted laser desorption/ionization time-of-flight (MALDI-TOF) mass spectrometry. The result is shown in FIG. 22b.

The homochiral peptide complex (T-V6) was freeze-dried and stored until use.

Experimental Example 1. Induction of Formation of Self-Assembled Structure

The lyophilized heterochiral peptide complex powder obtained from Examples 1-4 or the lyophilized homochiral peptide complex powder obtained from Comparative Examples 1-2 was rehydrated with doubly distilled water and the concentration was determined spectrophotometically using the molar extinction coefficient of tryptophan (5,690 M$^{-1}$ cm$^{-1}$) at 280 nm in water/acetonitrile (1:1) solution.

All the peptide samples were diluted to 1 mM and divided into 1-mL aliquots. The aliquots were heated at 95° C. for 1 hour and slowly annealed in a water bath overnight. After the annealing process, the samples were incubated at room temperature and the self-assembly process with time was analyzed by CD, AFM, WAXS, NMR, etc.

Experimental Example 2. Structural Analysis of Self-Assembled Structure of Homochiral Peptide Complex FIG. 5a shows the CD spectra of the homochiral peptide complexes of Comparative Example 1 and Comparative Example 2, which are enantiomers, FIG. 5b shows the AFM image of the homochiral peptide complex of Comparative Example 1, and FIG. 5c shows the AFM image of the homochiral peptide complex of Comparative Example 2.

Figure 6:
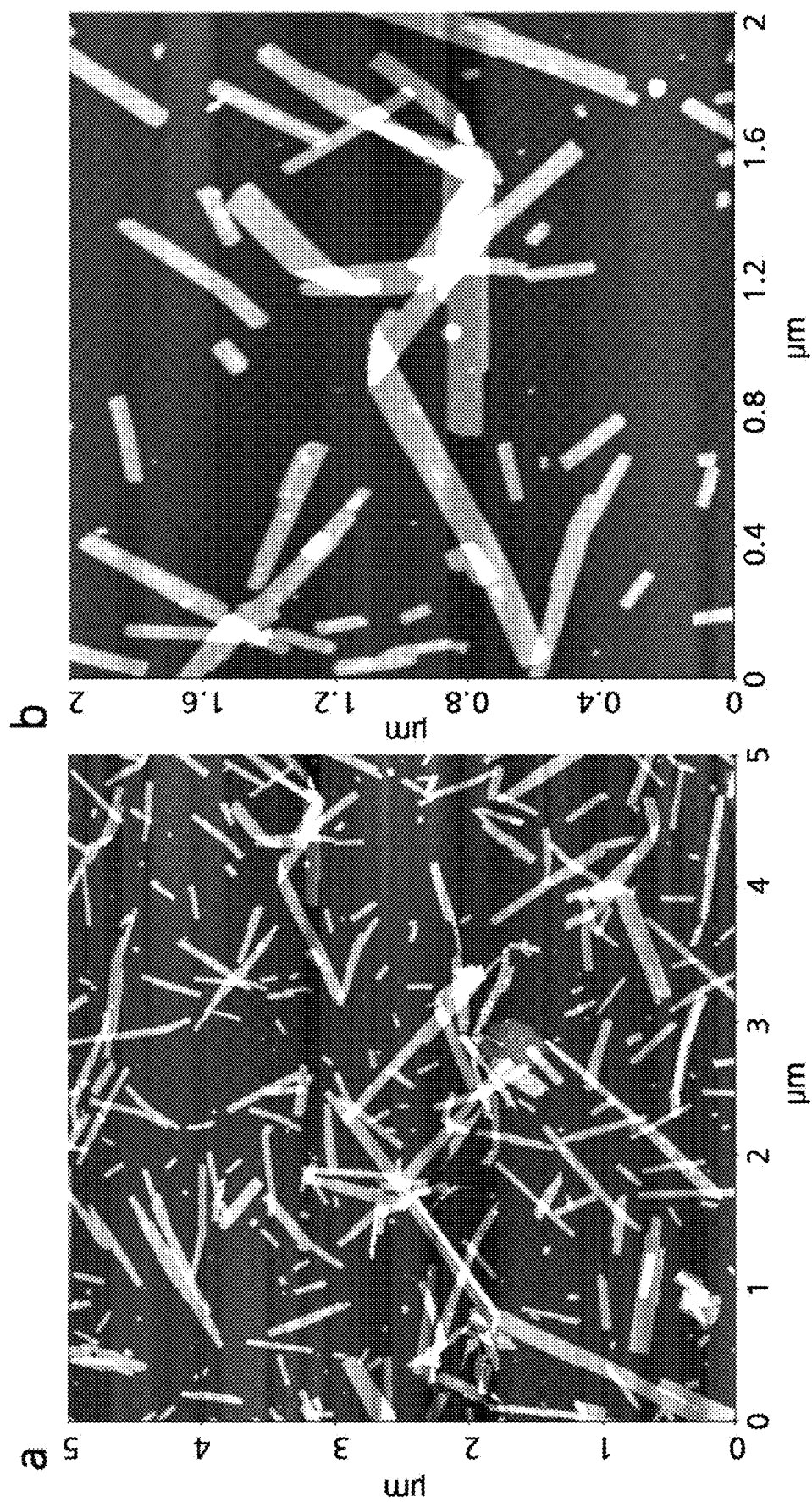
FIG. 6 shows the AFM images of a homochiral peptide complex prepared in Comparative Example 1 in a global minimum state (crystallized form).
Figure 7:
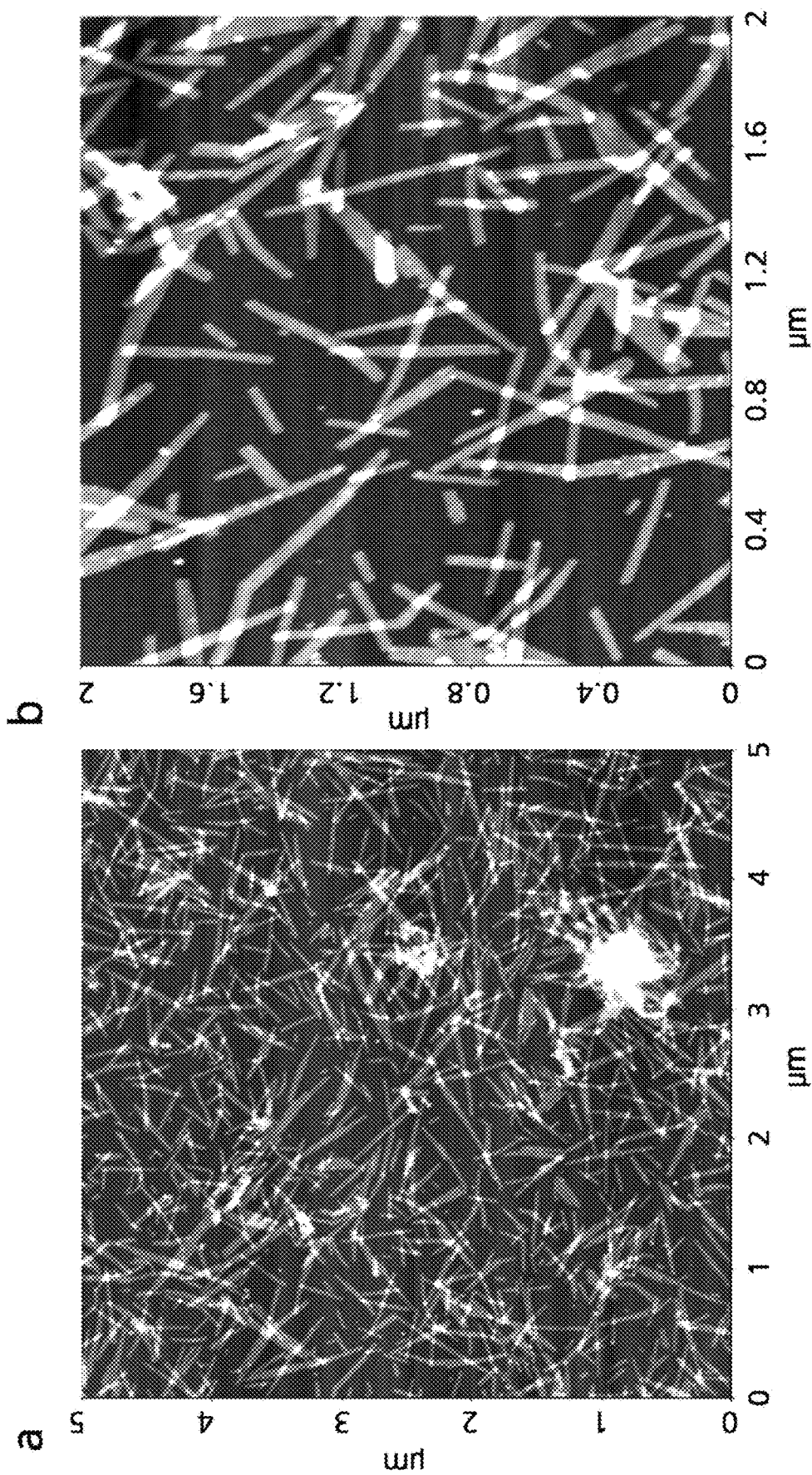
FIG. 7 shows the AFM images of a homochiral peptide complex prepared in Comparative Example 2 in a global minimum state (crystallized form).

FIG. 6 shows the AFM images of the homochiral peptide complex prepared in Comparative Example 1 in a global minimum state (crystallized form), and FIG. 7 shows the AFM images of the homochiral peptide complex prepared in Comparative Example 2 in a global minimum state (crystallized form).

Figure 5A:
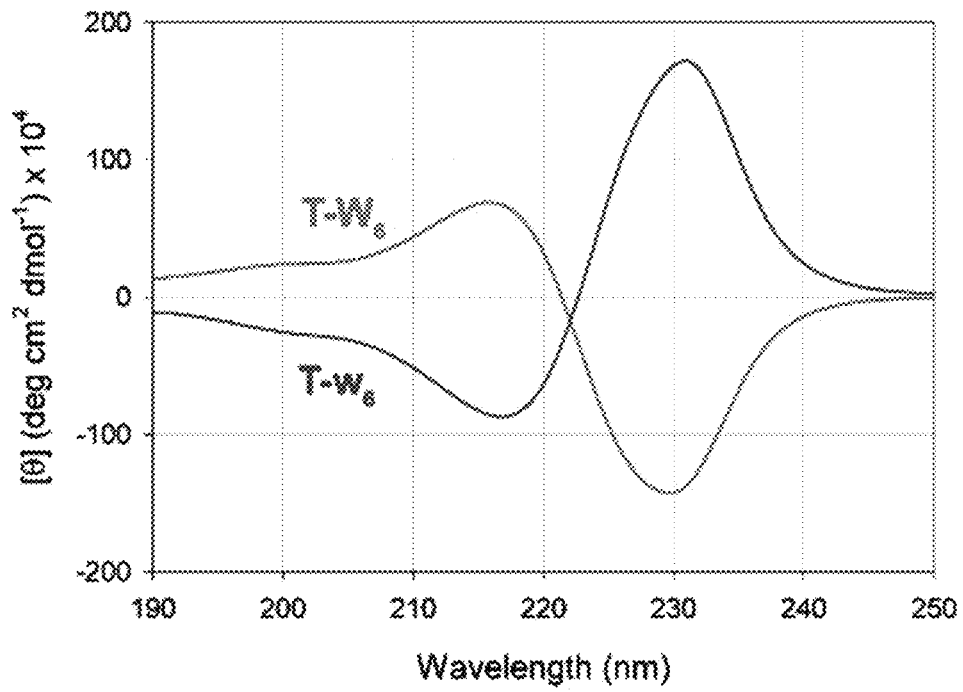
FIGS. 5a-5c show a result of observing differential self-assembly of homochiral peptide complexes of Comparative Examples 1-2 and heterochiral peptide complexes of Examples 1-4.

As shown in FIG. 5a, the CD spectroscopy analysis result showed that the homochiral peptide complex of Comparative Example 1 (T-W$_6$) consisting only of L-tryptophan and the homochiral peptide complex of Comparative Example 2 (T-w$_6$) consisting only of D-tryptophan were mirror images of each other. That is to say, it was confirmed that the peptides of Comparative Examples 1-2 have an enantiomeric relationship with each other.

Figure 5B:
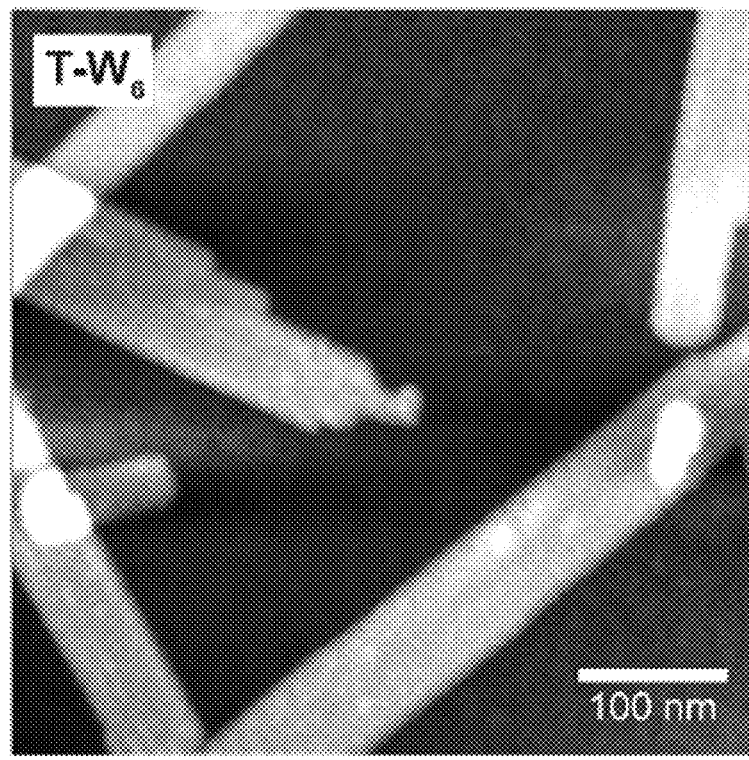
Figure 5C:
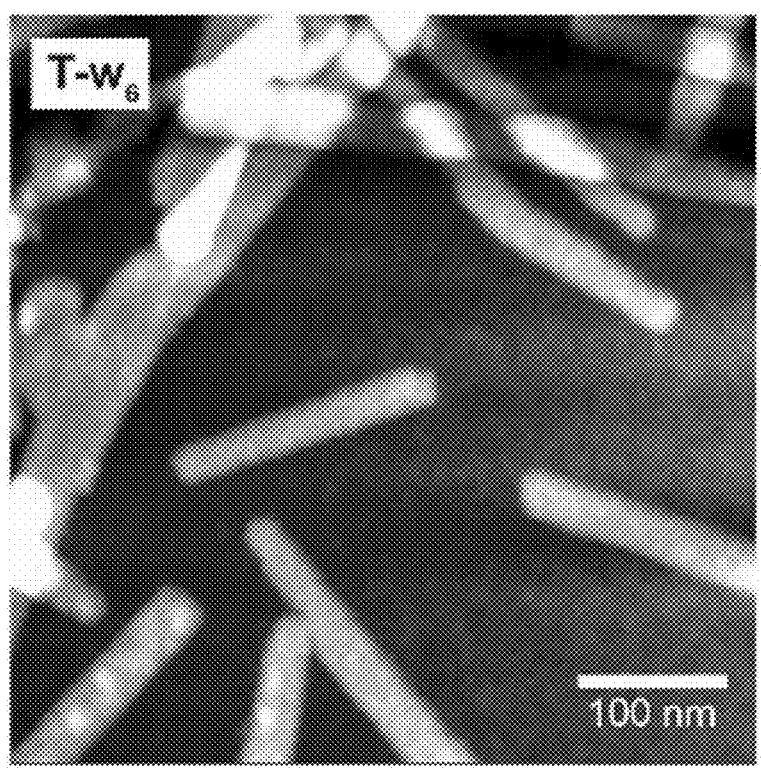

As shown in FIG. 5b, FIG. 6 and FIG. 7, it was confirmed that the homochiral peptide complexes of Comparative Example 1 and Comparative Example 2 were self-assembled into flat and rectangular nanostructures (crystals), as in misfolded peptides or proteins (e.g., amyloid peptides).

In addition, the CD (secondary structure) and AFM (morphology) results for the homochiral peptide complexes of Comparative Examples 1-2 were virtually identical regardless of the time after the dissolution, suggesting fast self-assembly at the global free energy minimum.

Experimental Example 3. Structural Analysis of Self-Assembled Structure of Heterochiral Peptide Complex FIG. 8 shows the CD spectra showing the time course of self-assembly of the heterochiral (racemic) peptide complex of Example 1 (T-(wW)$_3$) in solution.

Figure 9A:
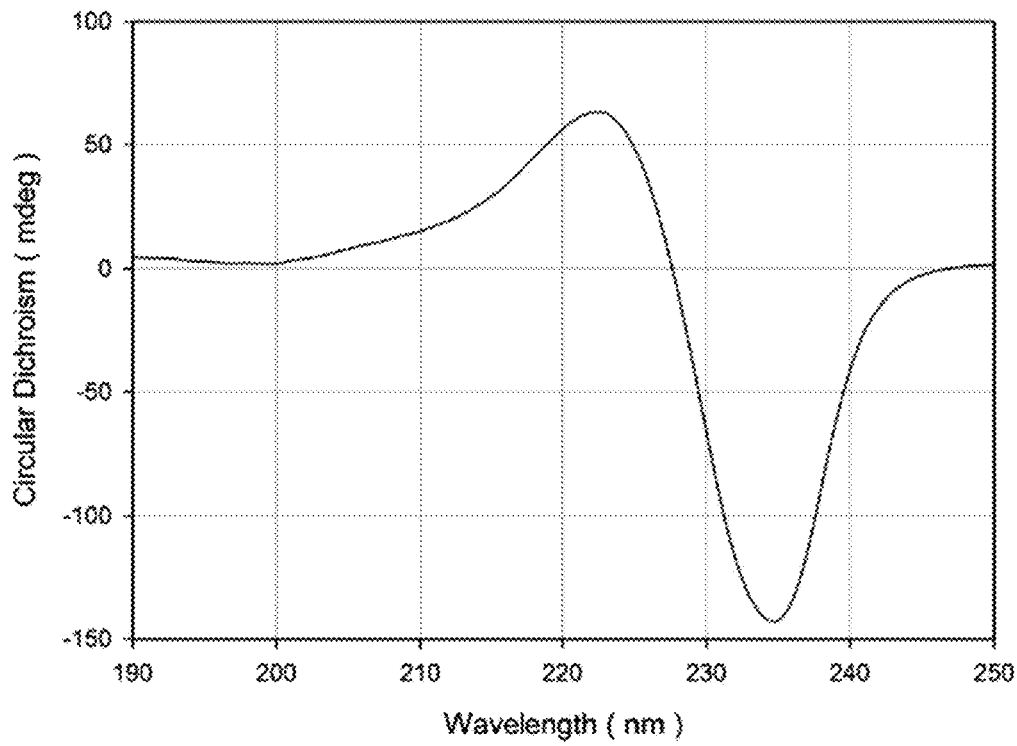
FIG. 9a shows the CD spectrum of a heterochiral (racemic) peptide complex of Example 1 (T-(wW)$_3$) after 6 weeks.
Figure 9B:
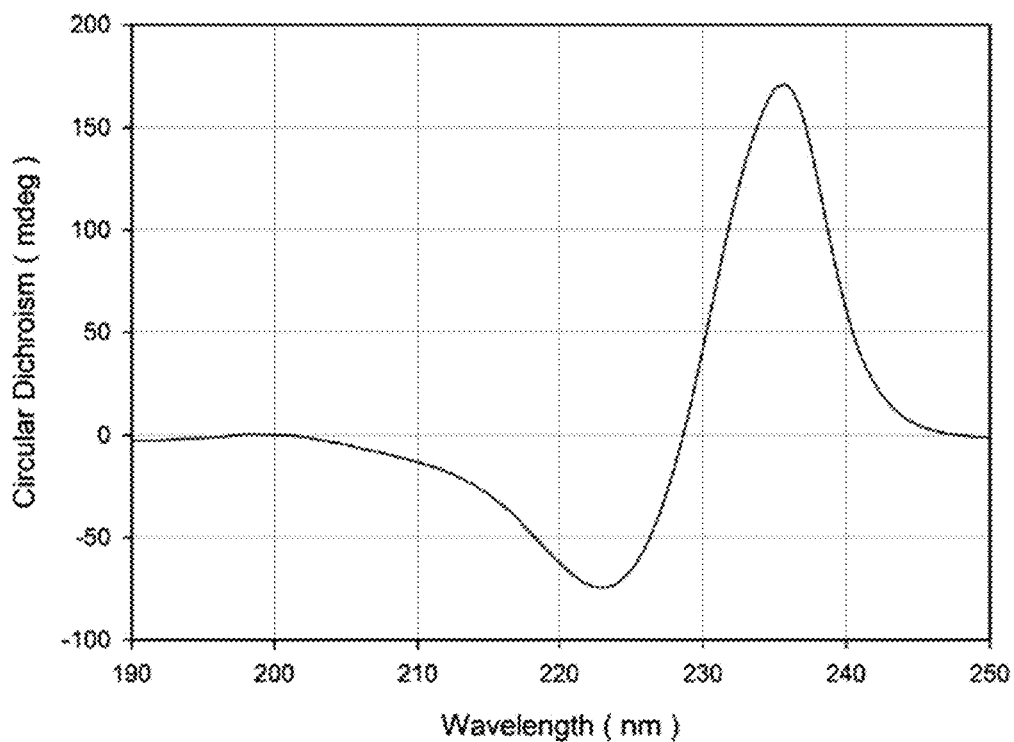
FIG. 9b shows the CD spectrum of a heterochiral (racemic) peptide complex of Example 2 (T-(Ww)$_3$) after 6 weeks.

FIG. 9a shows the CD spectrum of the heterochiral (racemic) peptide complex of Example 1 (T-(wW)$_3$) after 6 weeks, and FIG. 9b shows the CD spectrum of the heterochiral (racemic) peptide complex of Example 2 (T-(Ww)$_3$) after 6 weeks.

Figure 8:
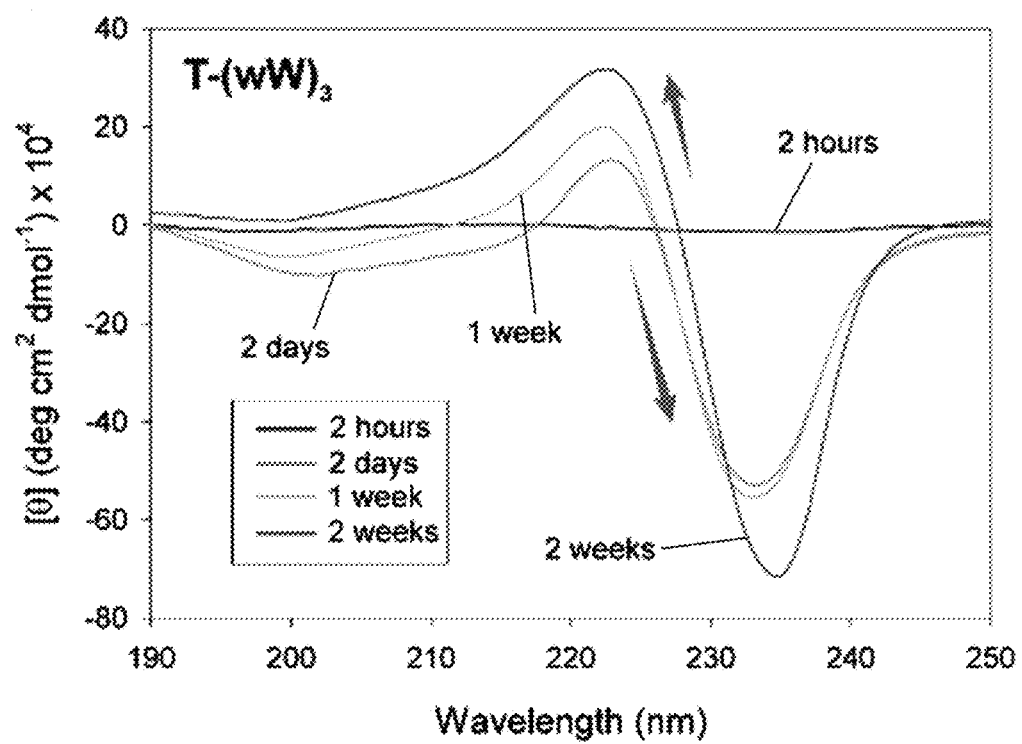
FIG. 8 shows the CD spectra showing the time course of self-assembly of a heterochiral (racemic) peptide complex of Example 1 (T-(wW)$_3$) in solution.

As shown in FIG. 8, the heterochiral peptide complex of Example 1 (T-(wW)$_3$), which is a heterochiral racemic peptide with alternating D- and L-tryptophans, showed markedly slower self-assembly kinetics than those of the homochiral peptide complexes of Comparative Examples 1-2.

For some time after the dissolution in distilled water, the heterochiral (racemic) peptide complex of Example 1 (T-(wW)$_3$) did not show any noticeable CD signal; i.e., the CD spectrum was almost identical to that of background water. Through this, it can be seen that the peptide complex maintains its initial structure rather than being self-assembled immediately.

The CD signals of the heterochiral (racemic) peptide complex of Example 1 (T-(wW)$_3$) developed gradually as time progressed (from 2 days to 2 weeks). After 2 weeks, the increase in the CD signals had almost ceased, indicating that an equilibrium state had reached for the self-assembly of the heterochiral peptide complex of Example 1 (T-(wW)$_3$).

The heterochiral peptide complex of Example 2 (T-(Ww)$_3$), which is an enantiomer of the heterochiral (racemic) peptide complex of Example 1 (T-(wW)$_3$), showed the same slow assembly kinetics and, as shown in FIG. 9, the heterochiral (racemic) peptide complex of Example 1 (T-(wW)$_3$) and the heterochiral peptide complex of Example 2 (T-(Ww)$_3$) exhibited mirror-image CD spectra at the self-assembly equilibrium.

Figure 10A:
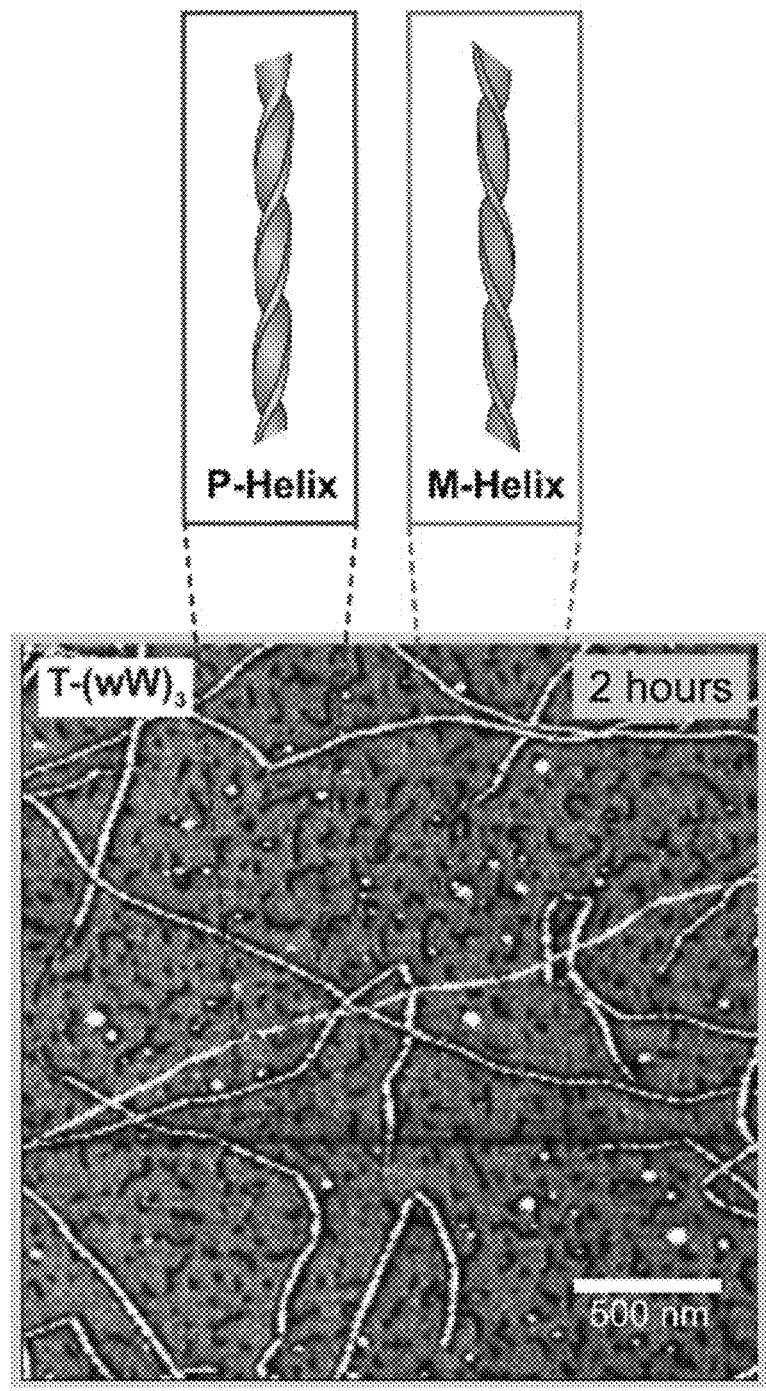
FIG. 10a shows the AFM image of a heterochiral (racemic) peptide complex (T-(wW)$_3$) after 2 hours.
Figure 10B:
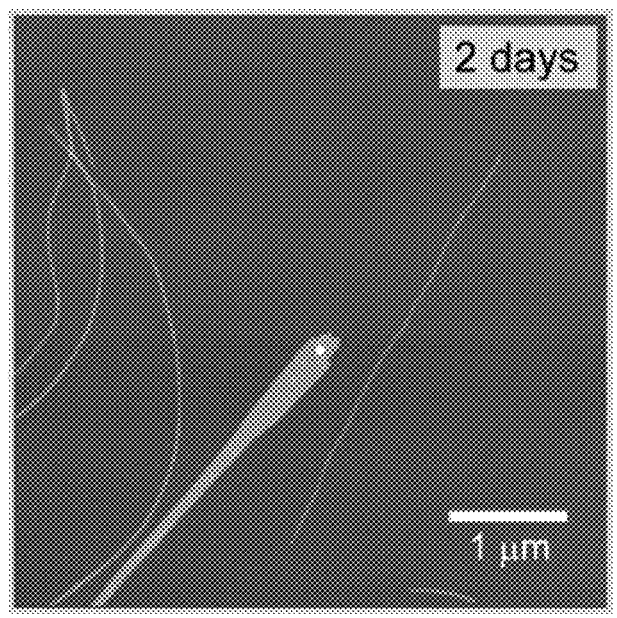
FIG. 10b shows the AFM image of a heterochiral (racemic) peptide complex (T-(wW)$_3$) after 2 days.
Figure 10C:
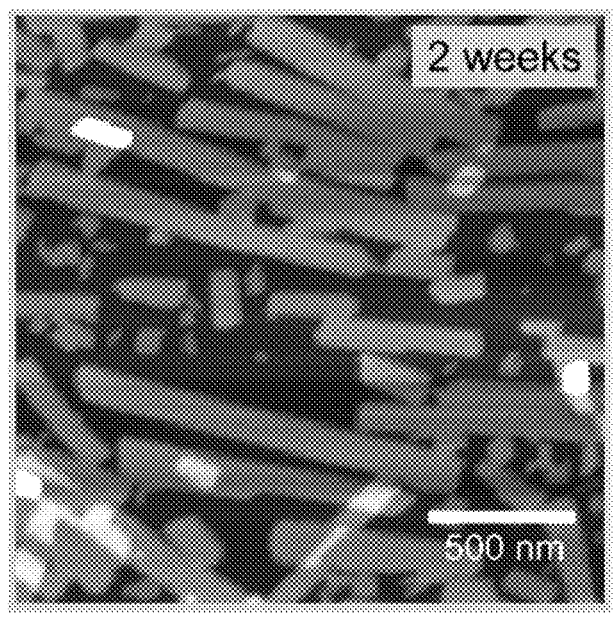
FIG. 10c shows the AFM image of a heterochiral (racemic) peptide complex (T-(wW)$_3$) after 2 weeks.
Figure 11:
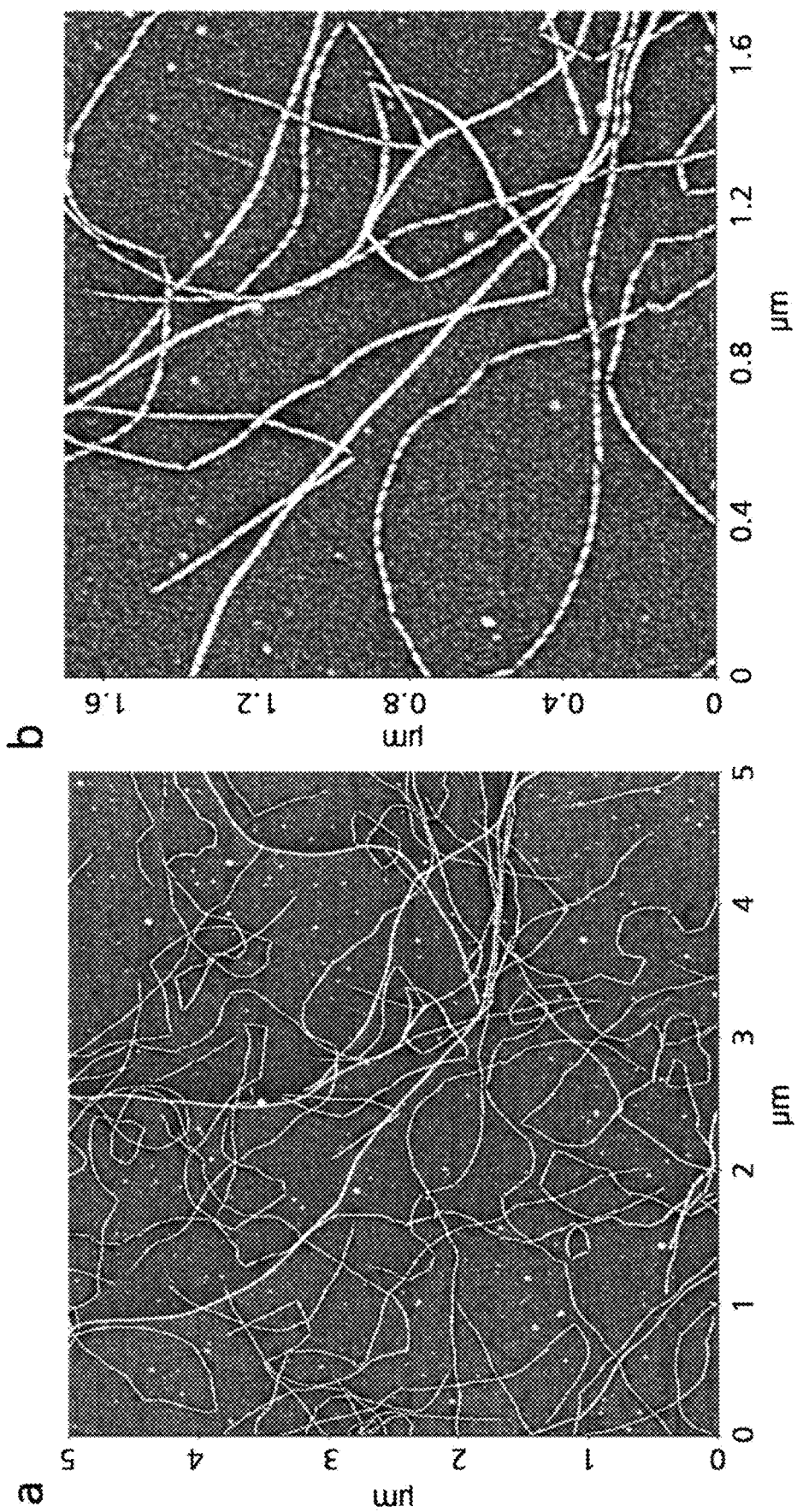
FIG. 11 shows the AFM images of a heterochiral (racemic) peptide complex (T-(wW)$_3$) after 2 hours.

FIG. 10a shows the AFM image of the heterochiral (racemic) peptide complex (T-(wW)$_3$) after 2 hours, FIG. 10b shows the AFM image of the heterochiral (racemic) peptide complex (T-(wW)$_3$) after 2 days, and FIG. 10c shows the AFM image of the heterochiral (racemic) peptide complex (T-(wW)$_3$) after 2 weeks. FIG. 11 shows the AFM images of the heterochiral (racemic) peptide complex (T-(wW)$_3$) after 2 hours, FIG. 12 shows the AFM images of the heterochiral (racemic) peptide complex (T-(wW)$_3$) after 2 days, and FIG. 13 shows the AFM images of the heterochiral (racemic) peptide complex (T-(wW)$_3$) after 2 weeks.

In order to investigate the morphology of the heterochiral peptide complex of Example 1 (T-(wW)$_3$) at each different stage of the self-assembly pathway, AFM images were obtained with time.

Referring to FIG. 10a and FIG. 11, the heterochiral peptide complex of Example 1 (T-(wW)$_3$) formed 1-dimensional (1 D) helical fibers through self-assembly for the first 2 hours. Some of the fibers were twisted in a right-handed fashion (P-helix) and some were twisted in a left-handed fashion (M-helix). The P-helix and the M-helix were in approximately equal proportions.

Figure 12:
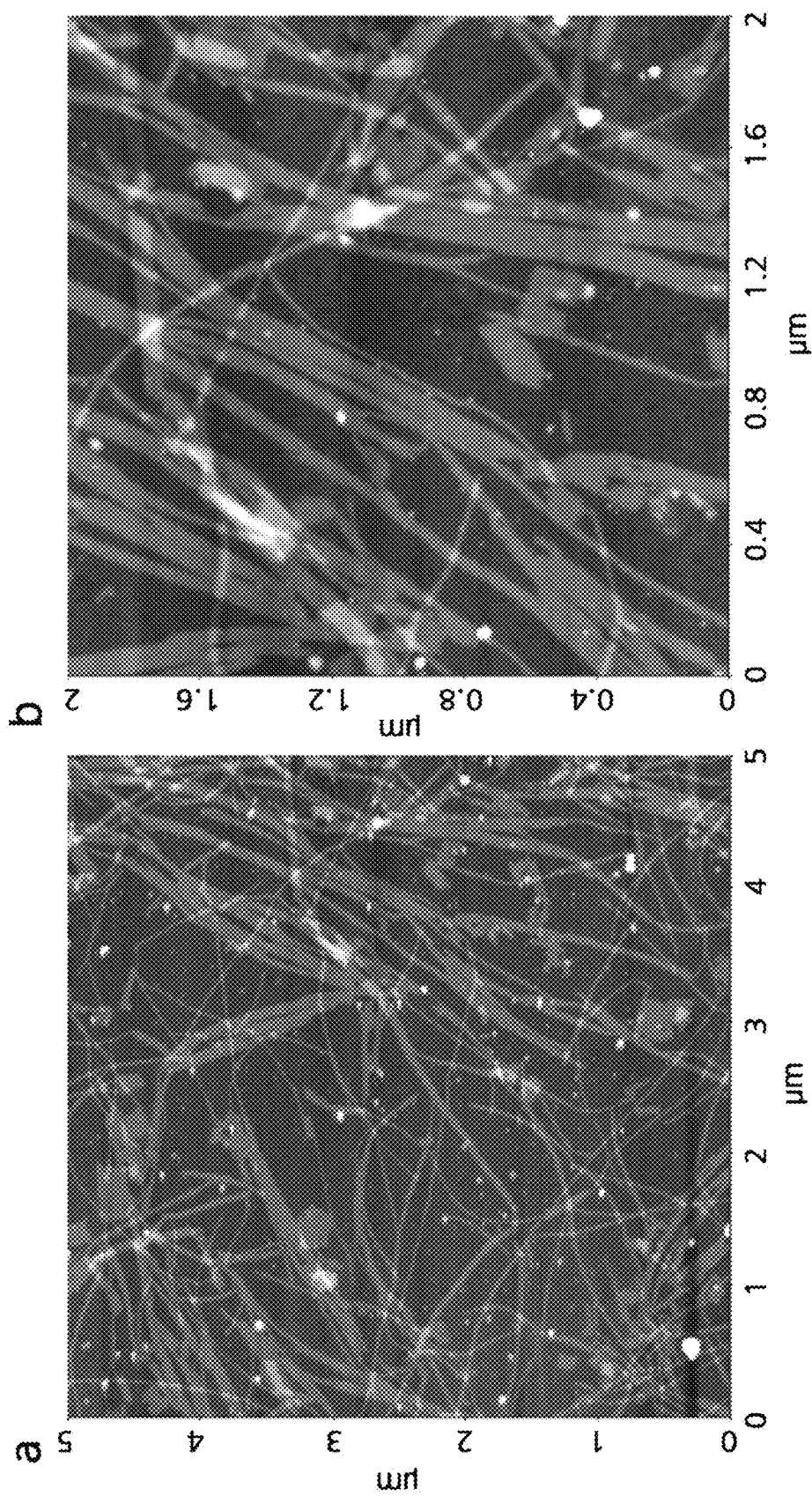
FIG. 12 shows the AFM images of a heterochiral (racemic) peptide complex (T-(wW)$_3$) after 2 days.
Figure 13:
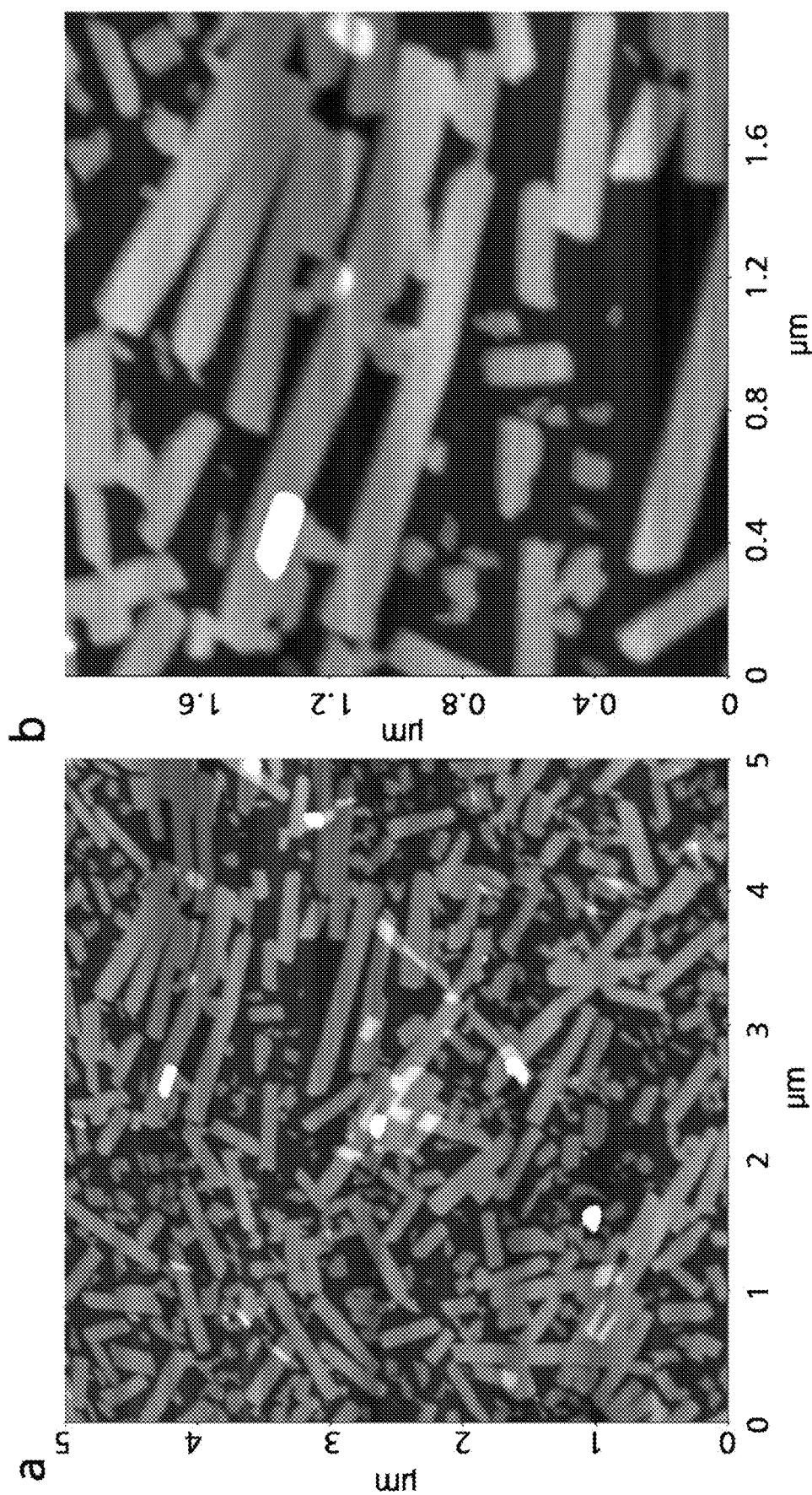
FIG. 13 shows the AFM images of a heterochiral (racemic) peptide complex (T-(wW)$_3$) after 2 weeks.

Referring to FIG. 10b and FIG. 12, after 2 days, the helices were fattened and associated laterally to form flat ribbons. The lengths of the ribbons were different from each other at this stage.

Referring to FIG. 10c and FIG. 13, finally after 2 weeks, crystals were formed in the equilibrium or global energy minimum state, and the length of the flat ribbon crystals was equal. Thus, it can be seen that the self-assembly kinetics of the heterochiral peptide complex of Example 1 are slow enough to be observed since the self-assembly occurs over 2 weeks (slow-motion self-assembly).

The self-assembly pathway of the heterochiral peptide complex of the present disclosure (T-(wW)$_3$ and T-(Ww)$_3$) share many similarities with the self-assembly pathway of amyloid peptides. Specifically, it has been recognized that one of the most common morphological transitions in amyloid peptides is as follows:

Twisted ribbon→flattening of the twisted ribbon→crystal

It can be seen that the twisted ribbons of amyloid peptides are similar to the helical fibers of the heterochiral racemic peptide complex of the present disclosure. The crystal of the amyloid peptide is considered the global energy minimum state in amyloid peptides, which is in line with the formation of crystals in the equilibrium or global energy minimum state of the heterochiral peptide complex of the present disclosure (T-(wW)$_3$ and T-(Ww)$_3$).

Overall, it was confirmed that the peptide complexes of Comparative Examples 1-2 and Examples 1-2 have the same peptide self-assembly pathway despite the difference in sequences and chiralities. In other words, it was confirmed that the slowly self-assembling heterochiral peptide complex of the present disclosure (T-(wW)$_3$) and the homochiral peptides of Comparative Examples 1-2 (T-W$_6$, T-w$_6$) share the same self-assembly pathway.

Experimental Example 4. WAXS Analysis

The overall shape of the crystals of the heterochiral peptide complex prepared in Example 1 (T-(wW)$_3$) was almost identical to those of the homochiral peptide complexes of Comparative Example 1 and Comparative Example 2 (T-W$_6$ and T-w$_6$).

However, the detailed molecular arrangement of the peptide in each crystal might be different. To address this question, wide-angle X-ray scattering (WAXS) analysis of the colloidal crystal solution was performed.

Figure 14A:
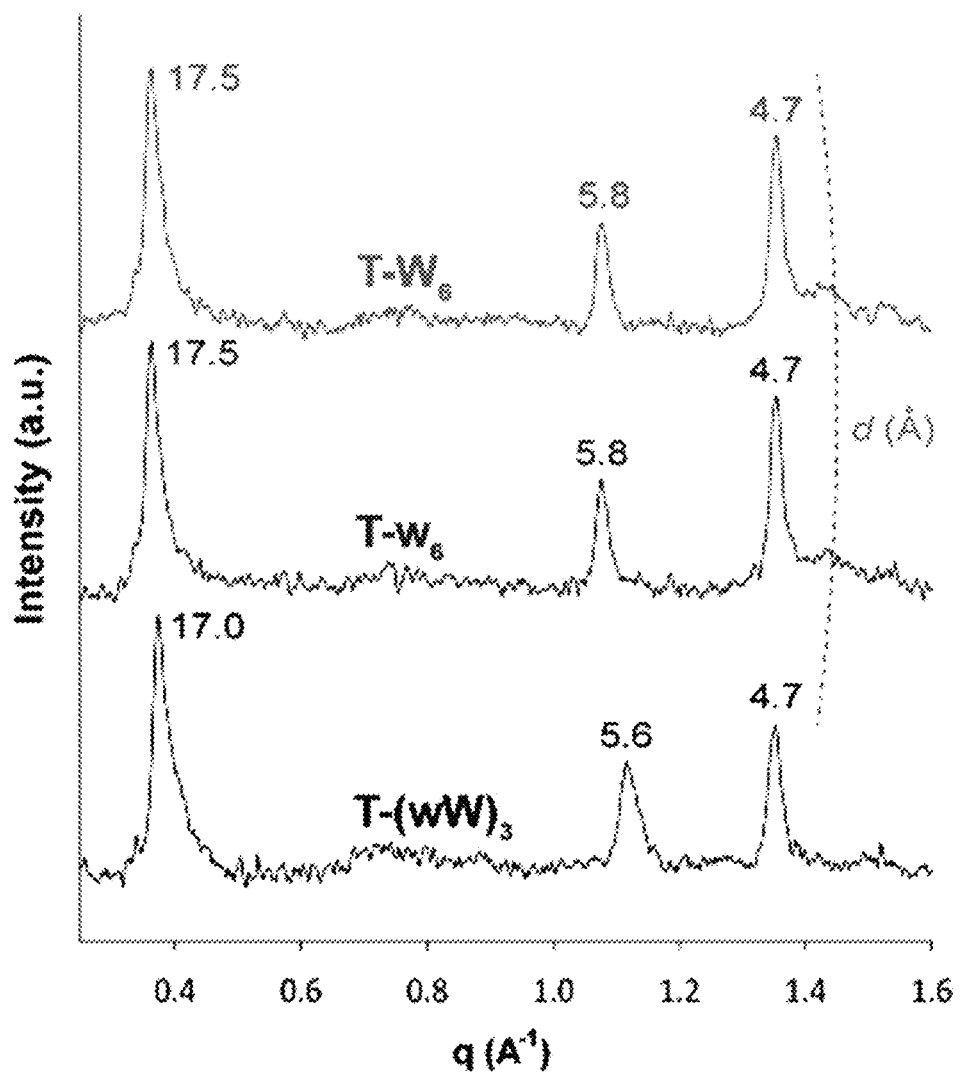
FIG. 14a shows the synchrotron WAXS data of a heterochiral peptide complex prepared in Example 1 (T-(wW)$_3$) and homochiral peptide complexes of Comparative Example 1 and Comparative Example 2 (T-W$_6$ and T-w$_6$)
Figure 14B:
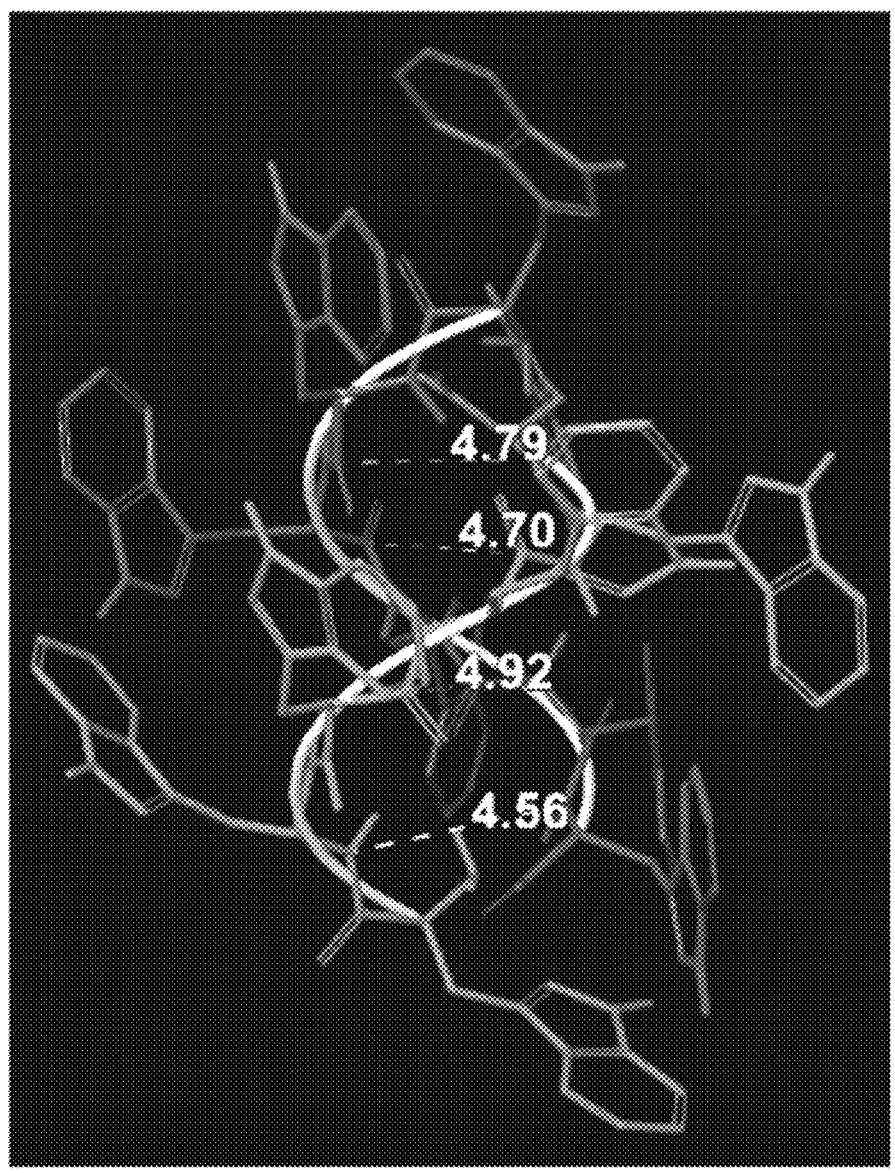
FIG. 14b shows the MD simulation result of a (wW)$_3$ peptide in a heterochiral peptide complex of Example 1. The numbers in FIG. 14 indicate distances in angstroms.

FIG. 14a shows the synchrotron WAXS data of the heterochiral peptide complex prepared in Example 1 (T-(wW)$_3$) and the homochiral peptide complexes of Comparative Example 1 and Comparative Example 2 (T-W$_6$ and T-w$_6$), and FIG. 14b shows the MD simulation result of the (wW)$_3$ peptide in the heterochiral peptide complex of Example 1. The numbers in FIG. 14 indicate distances in angstroms.

As shown in FIG. 14, the reflections for the homochiral peptide complexes of Comparative Example 1 and Comparative Example 2 (T-W$_6$ and T-w$_6$) (d=4.7, 5.8 and 17.5 Å) were identical, which is not surprising considering their identical structures except the enantiomeric relationship of the homochiral peptide complexes of Comparative Example 1 and Comparative Example 2 (T-W$_6$ and T-w$_6$).

On the other hand, the reflections for the heterochiral peptide complex prepared in Example 1 (T-(wW)$_3$) (d=4.7, 5.6 and 17.0 Å) were somewhat different from those of the heterochiral peptide complexes of Comparative Examples 1-2, especially at 5.6 Å and 17.0 Å.

Reflections at 4.7 Å are found in all the complexes of Example 1, Comparative Example 1 and Comparative Example 2 and correspond to the interstrand distance of β-sheets.

The d-spacing of the heterochiral peptide complex prepared in Example 1 (T-(wW)$_3$) was 17.0 Å, and the d-spacing of the homochiral peptide complexes of Comparative Example 1 and Comparative Example 2 (T-W$_6$ and T-w$_6$) was 17.5 Å. Although the d-spacings were somewhat larger than the typical values of β-sheets, they represent intersheet distances.

Molecular dynamics (MD) simulation analysis was performed to gain insight into the structure of the heterochiral peptide complex prepared in Example 1 (T-(wW)$_3$) achieved from self-assembly. To simplify the simulation, only the (wW)$_3$ peptide segment associated with self-assembly was used for the analysis. The simulation was performed with two different methods. In the first method, the simulation was started from the arbitrarily generated D-tryptophan/L-tryptophan (D-Trp/L-Trp) repeating peptide having fixed dihedral angles ($\varphi$=−180° and $\psi$=−180°). In the second method, tyrosines from poly(D-/L-tyrosine) were replaced with corresponding tryptophans before commencing the MD simulation.

Poly(D-/L-tyrosine) has been reported to have the spiral form of an antiparallel double-stranded β-helix. A similar structure was confirmed when the tyrosines were replaced with tryptophans. That is to say, it was confirmed that the conformation of the (wW)$_3$ peptide of Example 1 was similar to the antiparallel double-stranded β-helix of the poly(D-/L-tyrosine) (FIG. 14 b).

More specifically, the (wW)$_3$ peptide of Example 1 was more curved than ordinary β-sheet structures, but unlike poly(D-/L-tyrosine), it did not have a perfect spiral shape due to the shorter peptide length. This is consistent with the WAXS data showing that the distance between the β strands of the heterochiral peptide complex prepared in Example 1 (T-(wW)$_3$) was 4.56-4.92 Å.

Figure 15:
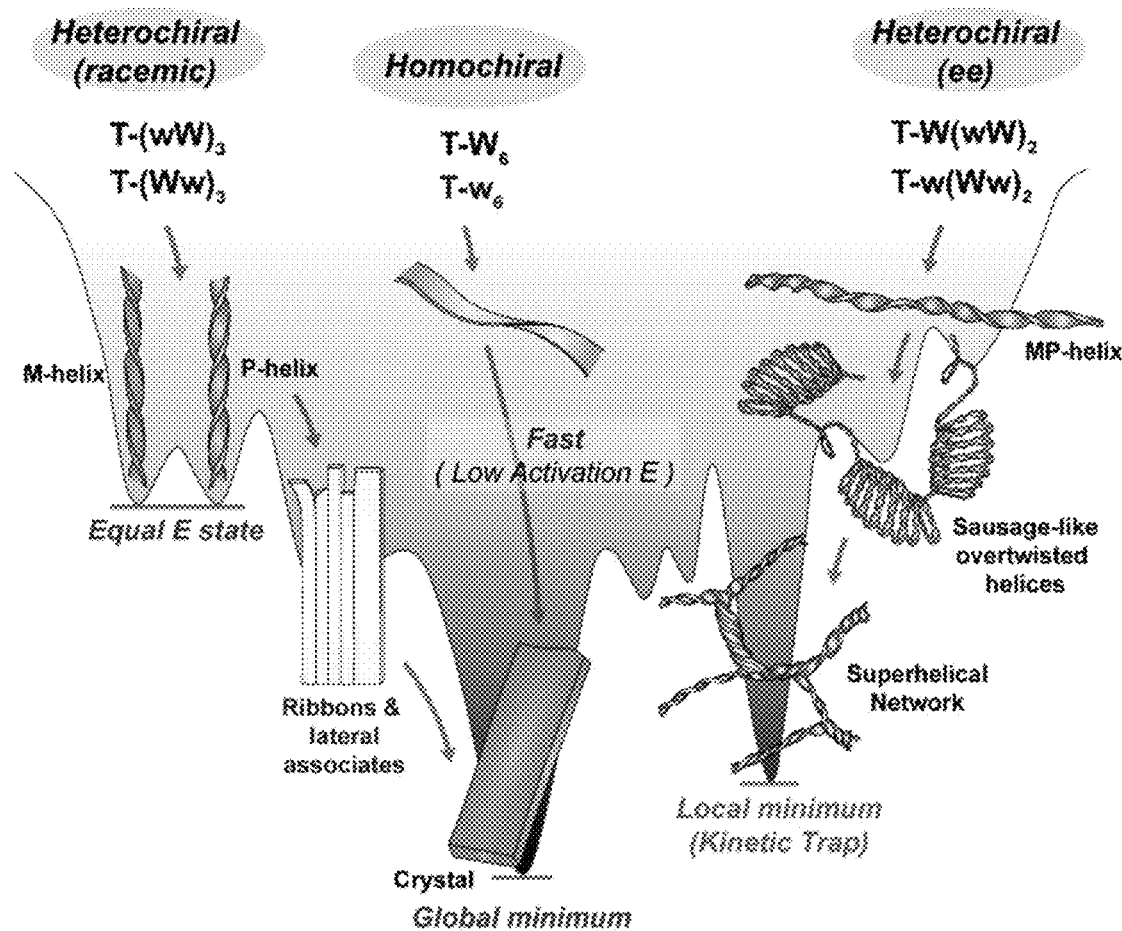
FIG. 15 schematically illustrates the self-assembly pathways of a heterochiral peptide complex and a homochiral peptide complex of the present disclosure.

Taken together, it was confirmed that the homochiral peptide complexes of Comparative Example 1 and Comparative Example 2 (T-W$_6$ and T-w$_6$) and the heterochiral peptide complex prepared in Example 1 (T-(wW)$_3$) have almost the same final self-assembled structure despite the difference in chiral compositions and molecular conformations (FIG. 15).

Experimental Example 5. Structural Analysis of Asymmetric Heterochiral (ee) Peptide Complex To further explore the structural space of the heterochiral peptide, another type of a heterochiral peptide in which one of the tryptophan stereoisomer is in enantiomeric excess was designed (FIG. 2e, f; heterochiral ee in FIG. 15).

In the designed asymmetric heterochiral (ee) peptides (T-W(wW)$_2$ and T-w(Ww)$_2$) of Examples 3-4, one of the stereoisomers is expected to provide a stronger contribution than the other during self-assembly.

Figure 16A:
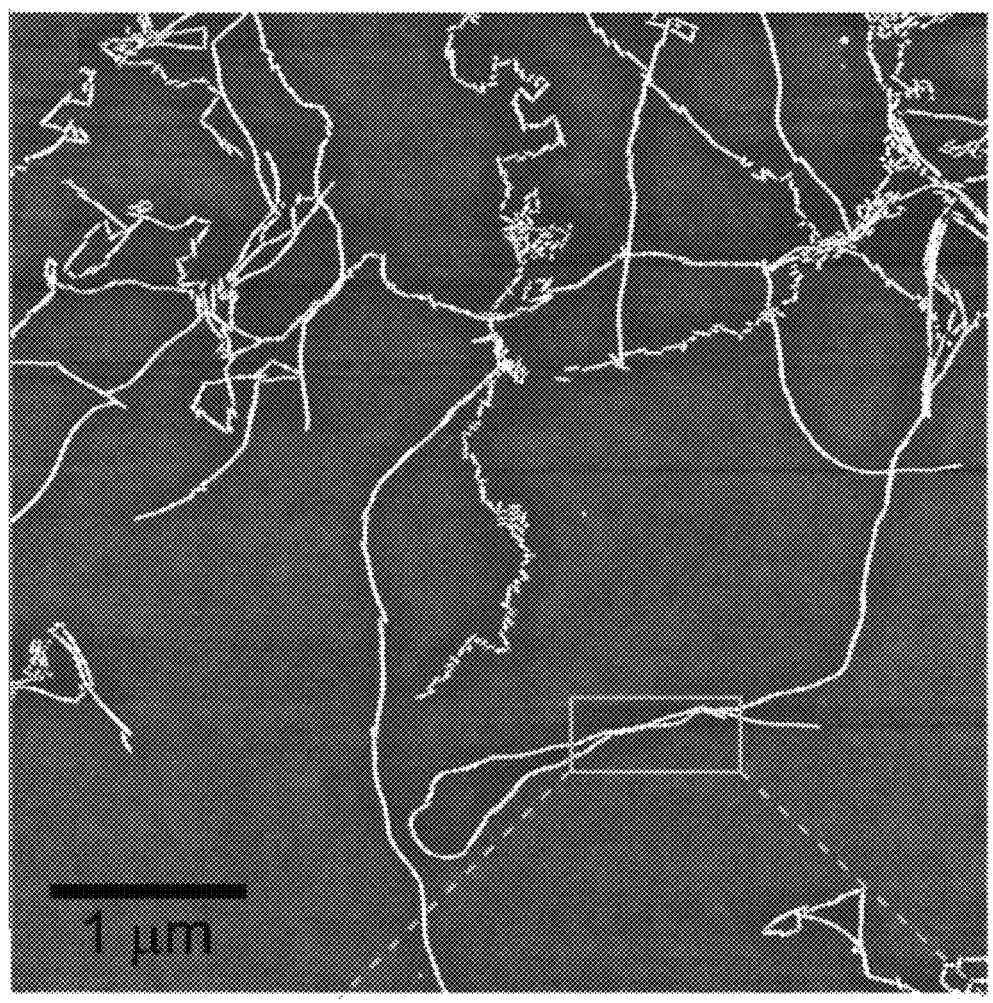
FIG. 16a shows the AFM images of the asymmetric heterochiral peptide (ee) complexes of Examples 3-4 (T-W(wW)$_2$ and T-w(Ww)$_2$) at the initial stage of self-assembly (after 2 hours)
Figure 16B:
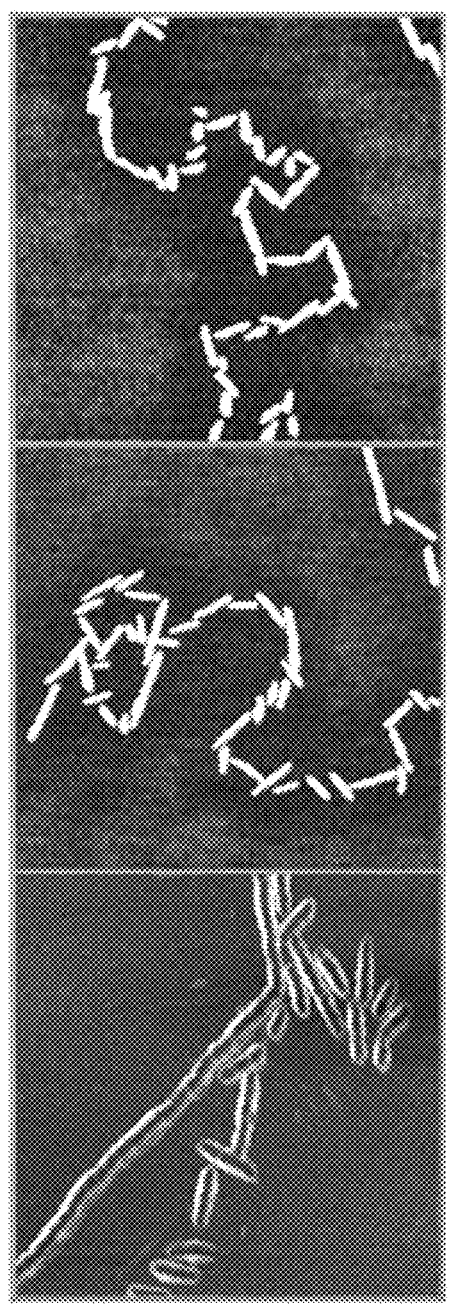
FIG. 16b shows the enlarged images of FIG. 16a, and FIG. 16c shows the unusual helical structures of the asymmetric heterochiral peptide (ee) complexes of Examples 3-4 (T-W(wW)$_2$ and T-w(Ww)$_2$).
Figure 16C:
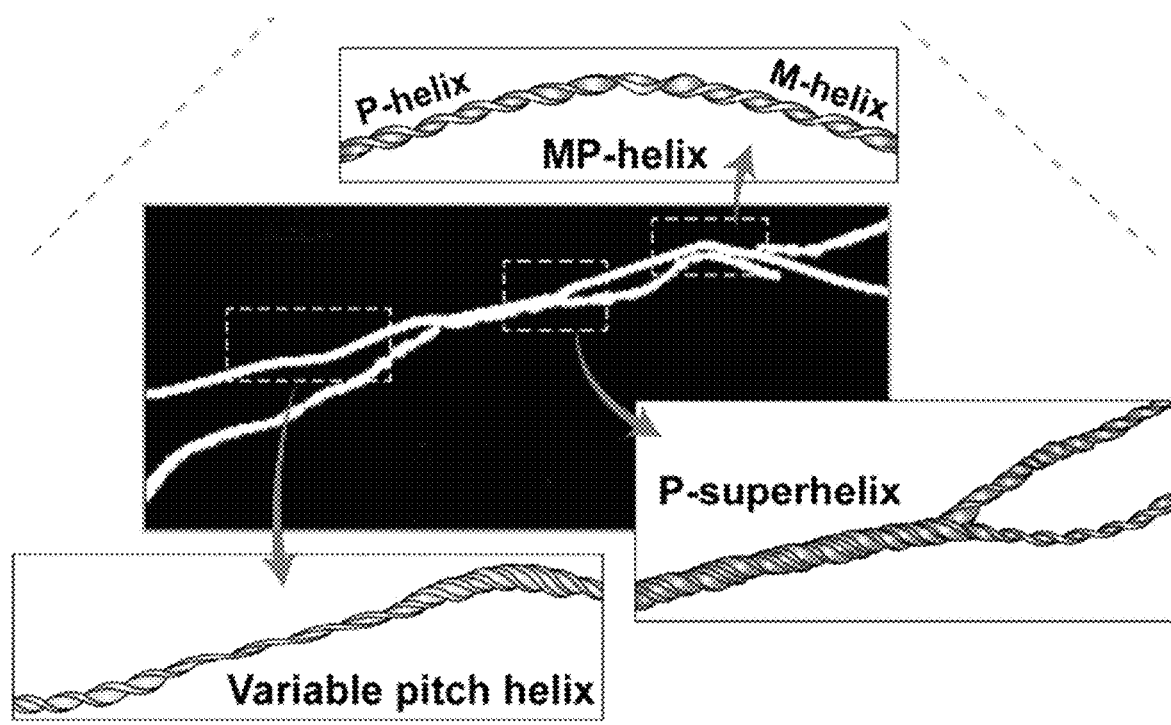
FIG. 16 shows a result of investigating the structure of asymmetric heterochiral peptide (ee) complexes of Examples 3-4 (T-W(wW)$_2$ and T-w(Ww)$_2$) at the initial stage of self-assembly.

FIG. 16 shows a result of investigating the structure of the asymmetric heterochiral peptide (ee) complexes of Examples 3-4 (T-W(wW)$_2$ and T-w(Ww)$_2$) at the initial stage of self-assembly. FIG. 16a shows the AFM images of the asymmetric heterochiral peptide (ee) complexes of Examples 3-4 (T-W(wW)$_2$ and T-w(Ww)$_2$) at the initial stage of self-assembly (after 2 hours), FIG. 16b shows the enlarged images of FIG. 16a, and FIG. 16c shows the unusual helical structures of the asymmetric heterochiral peptide (ee) complexes of Examples 3-4 (T-W(wW)$_2$ and T-w(Ww)$_2$).

Figure 17:
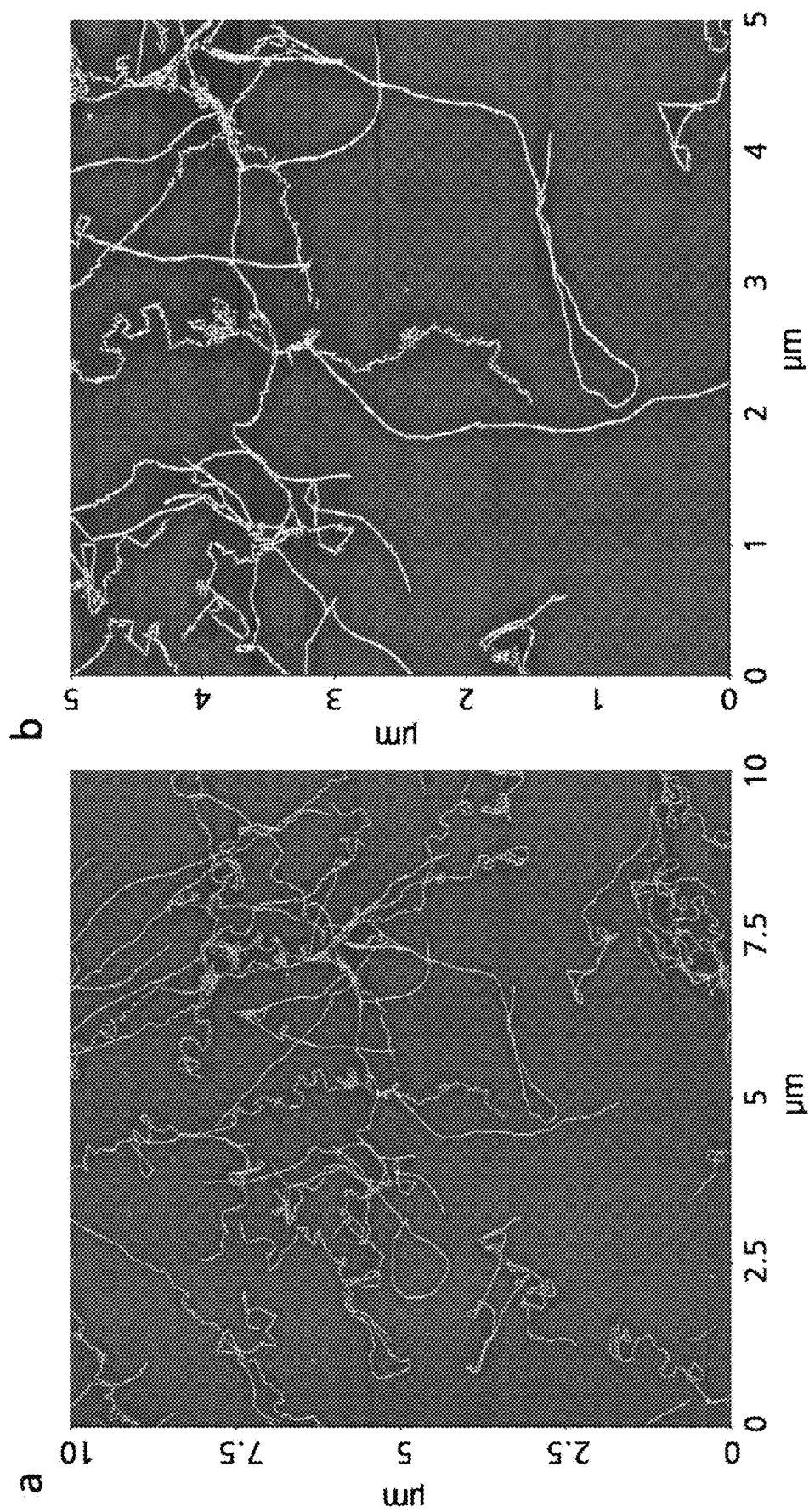
FIG. 17 shows the AFM images of an asymmetric heterochiral peptide (ee) complex of Example 3 (T-W(wW)$_2$) at the initial stage of self-assembly (after 2 hours).
Figure 18:
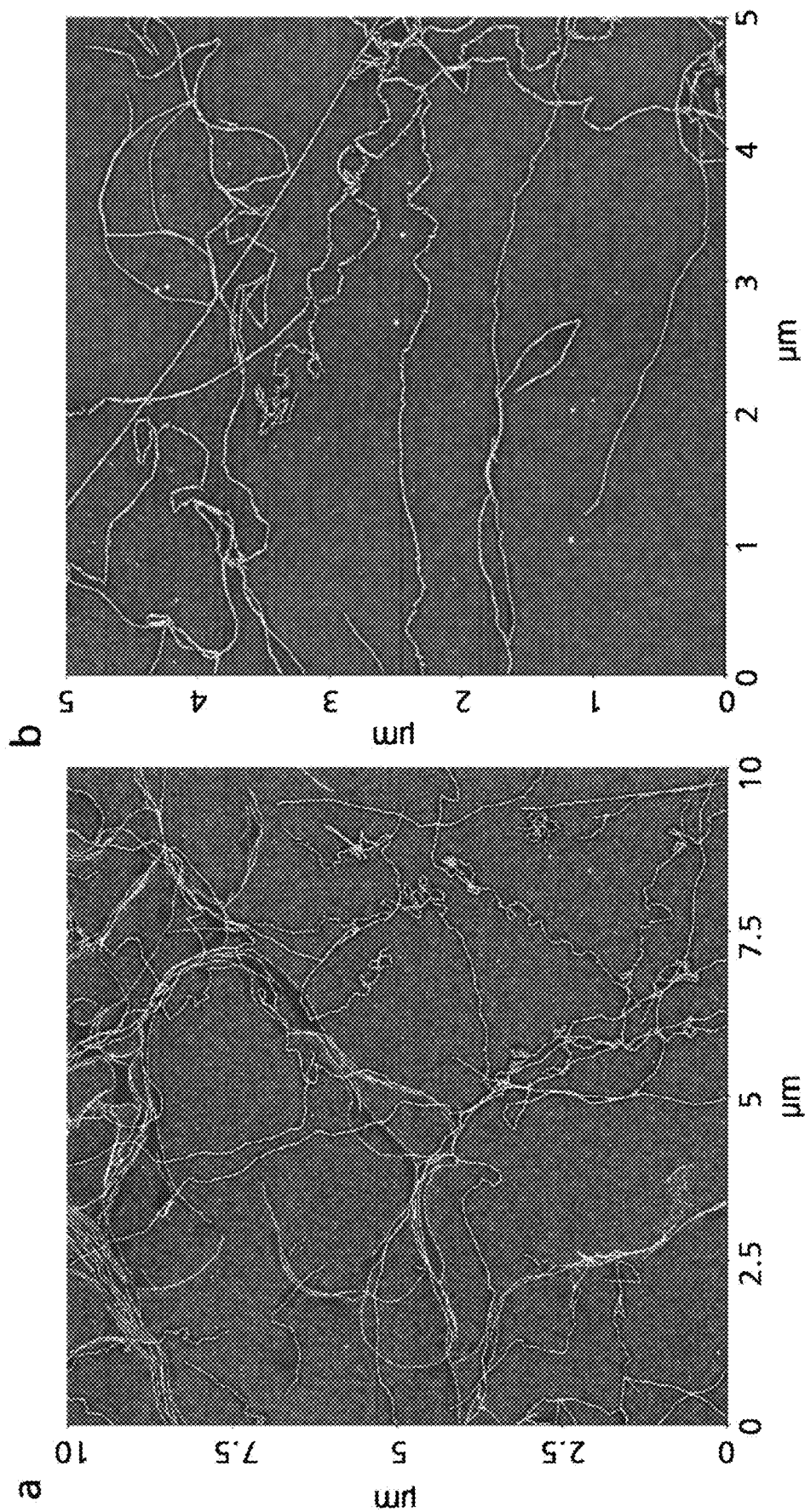
FIG. 18 shows the AFM images of an asymmetric heterochiral peptide (ee) complex of Example 4 (T-w(Ww)$_2$) at the initial stage of self-assembly (after 2 hours).
Figure 19:
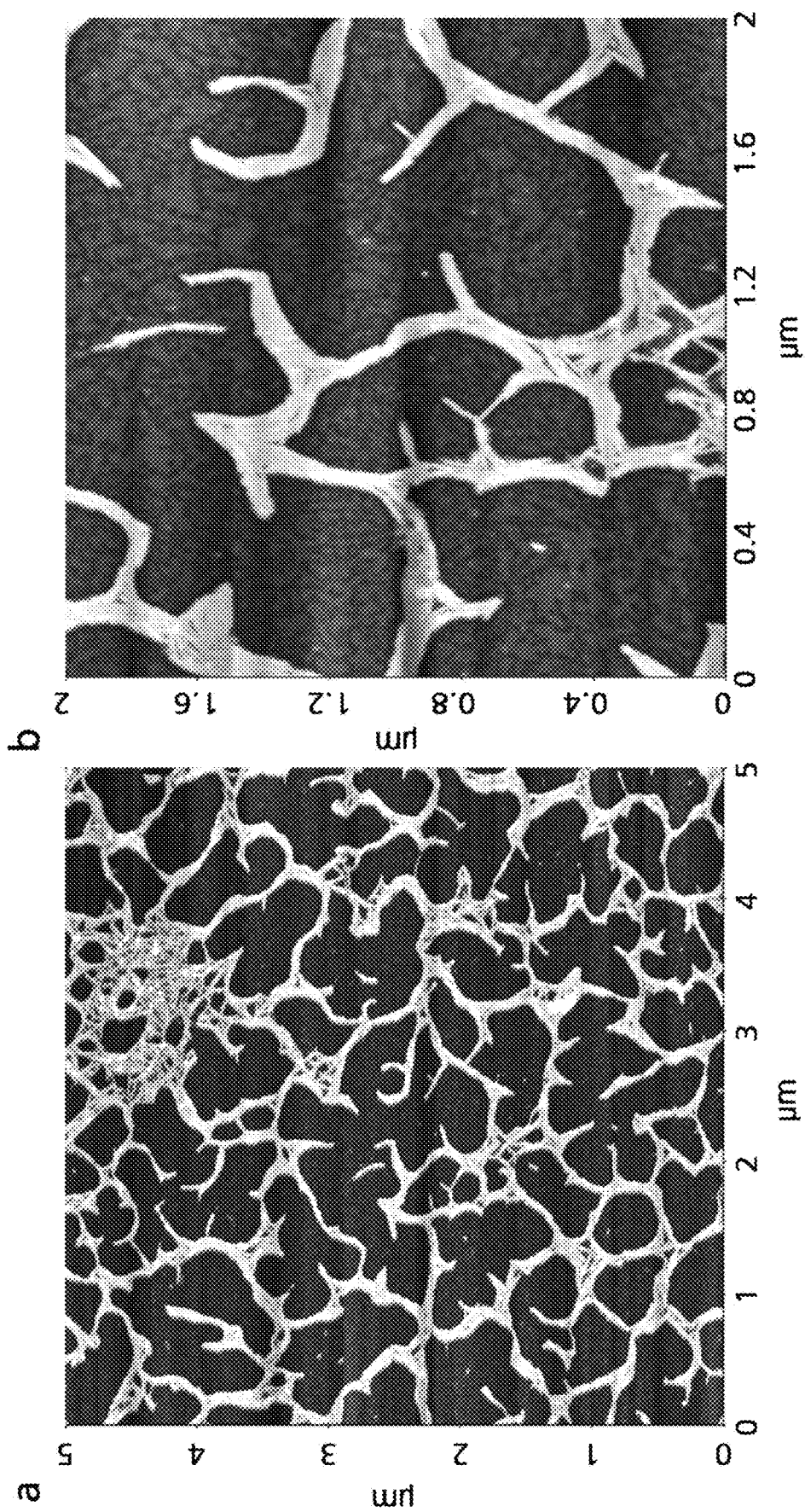
FIG. 19 shows the AFM images of an asymmetric heterochiral peptide (ee) complex of Example 3 (T-W(wW)$_2$) at the final stage of self-assembly (after 2 weeks, kinetically trapped state).
Figure 20:
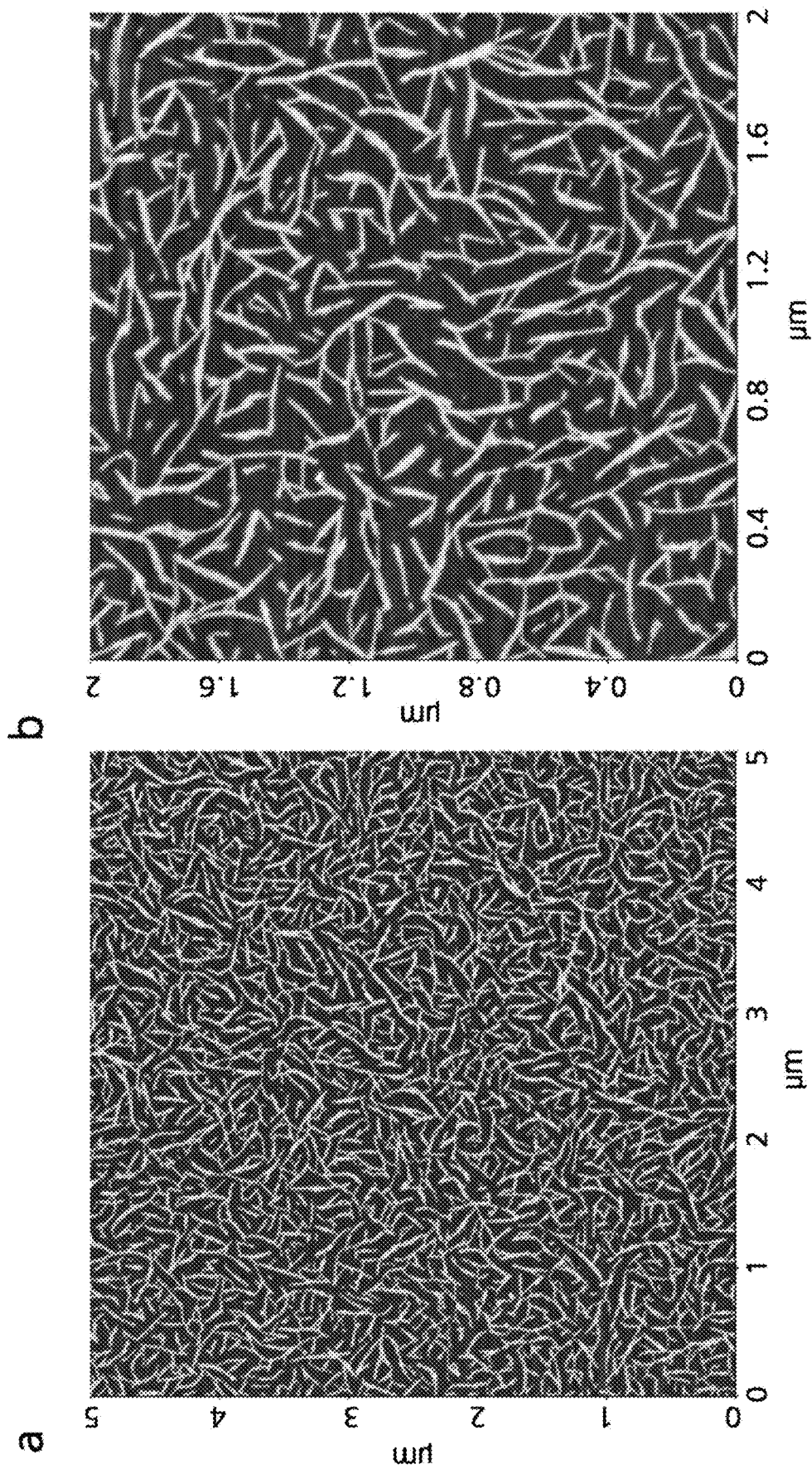
FIG. 20 shows the AFM images of an asymmetric heterochiral peptide (ee) complex of Example 4 (T-w(Ww)$_2$) at the final stage of self-assembly (after 2 weeks, kinetically trapped state).

FIG. 17 shows the AFM images of the asymmetric heterochiral peptide (ee) complex of Example 3 (T-W(wW)$_2$) at the initial stage of self-assembly (after 2 hours), FIG. 18 shows the AFM images of the asymmetric heterochiral peptide (ee) complex of Example 4 (T-w(Ww)$_2$) at the initial stage of self-assembly (after 2 hours), FIG. 19 shows the AFM images of the asymmetric heterochiral peptide (ee) complex of Example 3 (T-W(wW)$_2$) at the final stage of self-assembly (after 2 weeks, kinetically trapped state), and FIG. 20 shows the AFM images of the asymmetric heterochiral peptide (ee) complex of Example 4 (T-w(Ww)$_2$) at the final stage of self-assembly (after 2 weeks, kinetically trapped state).

As shown in FIGS. 16-20, the asymmetric heterochiral peptide (ee) complexes of Examples 3-4 (T-W(wW)$_2$ and T-w(Ww)$_2$) were self-assembled slowly similarly to the heterochiral (racemic) peptide complexes of Examples 1-2. Notably, significant twisting of the 1 D helical fibers was observed at the initial stage of self-assembly. Moreover, the generation of unique self-assembled intermediates including a fiver containing a right-handed helix (β-helix) and a left-handed helix (M-helix) of variable pitch was identified.

Referring to FIG. 16b, sausage-like intermediates in which short fibers are connected in a swirling shape, similar to a string of sausages, were identified at the initial stage of self-assembly of the asymmetric heterochiral peptide (ee) complexes of Examples 3-4 (T-W(wW)$_2$ and T-w(Ww)$_2$). The sausage-like intermediate is likely to have been formed by the overtwisting of the 1 D helical fiber. The twisted 1 D helical fibers were further intertwined to form a superhelix (FIG. 16c). All these unusual structures are formed by the misalignment of the asymmetric peptide building blocks in combination with the slow and dynamic nature of heterochiral self-assembly.

After 2 weeks of self-assembly, the intertwining and overtwisting of the asymmetric heterochiral peptide (ee) complex of Example 3 (T-W(wW)$_2$) had progressed extensively, resulting in the formation of a porous superhelical network (FIGS. 19-20). The porous superhelical network state can be considered as a kinetically trapped state because the transition into crystal has been kinetically inhibited by the formation of an intertwined superhelical network.

The possibility of using the novel intermediate with a 1 D helical morphology as an alignment medium for NMR residual dipolar coupling (RDC) measurement was shown in order to demonstrate the application potential of the slow-motion self-assembly of the heterochiral peptide complex of the present disclosure. RDC can provide valuable information regarding long-range orientation restraints of internuclear vectors in solution NMR spectroscopy. Especially, the distance restraints derived from nuclear Overhauser effect (NOE) are difficult to obtain for proteins which are 15 kDa or larger in size.

Thus, RDC can serve as the reliable source to improve the quality of NMR structure analysis. Specifically, when a sample is in an aqueous environment, dipolar couplings are degenerated due to randomized molecular motion. Therefore, the direction of the dipole should be limited to anisotropic preference in order to measure RDC. The alignment medium of the present disclosure may act as angular restraints as the degree of arrangement increases. As such alignment media, nematic liquid crystal molecules, compressed or stretched polymer gels, Pf1 filamentous phages, bicelles, etc. have been developed thus far. Because the alignment medium for RDC has its own specific characteristics such as the appropriate temperature and pH ranges, compatible solvents and the charge state of the alignment medium, there is an ongoing need of new alignment media applicable to various applications.

The self-assembled helical 1 D intermediate of the heterochiral peptide complex of Example 1 (T-(wW)$_3$) of the present disclosure can be used as an alignment medium for measuring RDC, similarly to the Pg1 filamentous phage having a 1 D structure.

Experimental Example 6. $^2$H-NMR Analysis Result

The ordering of water molecules was measured using the peptide complex of the present disclosure as an alignment medium. $^2$H-NMR was used and the analysis condition was as follows. The quadrupolar coupling of deuterium in D$_2$O was measured with one-pulse experiment. For identification of signal splitting from the NMR spectrum, the measurement values at 4.8 ppm were monitored based on the signal in general 10% (v/v) D$_2$O aqueous solution (H$_2$O/D$_2$O (90/10; v/v)). The result is shown in FIG. 21.

Figure 21:
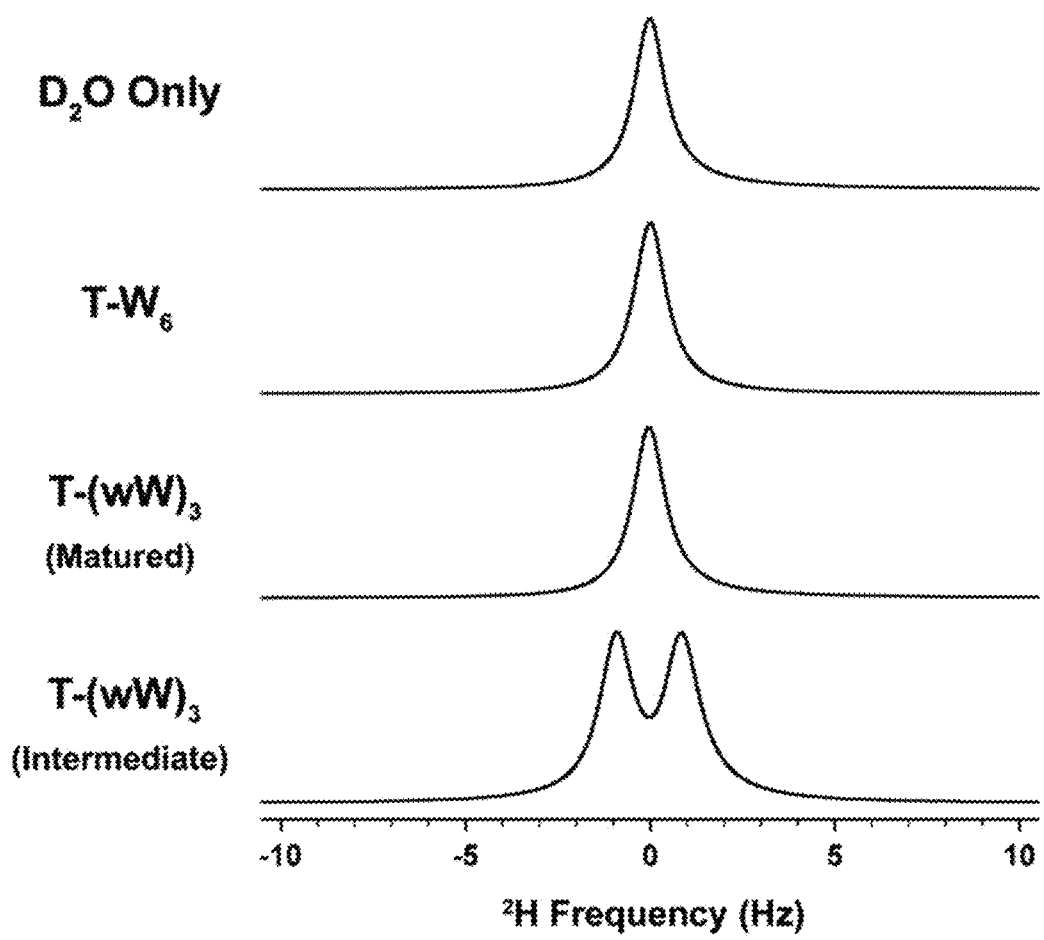
FIG. 21 shows the deuterium NMR spectra of a heterochiral peptide complex of Example 1 and a homochiral peptide complex of Comparative Example 1 with a varying assembly state in 10% (v/v) D$_2$O at 298 K. All spectra were acquired using a 700-MHz NMR spectrometer.

The homochiral peptide complex of Comparative Example 1 (crystal), the heterochiral peptide complex of Example 1 (T-(wW)$_3$) (matured; crystal) and the heterochiral peptide complex of Example 1 (T-(wW)$_3$) (intermediate; self-assembled 1 D intermediate) were evaluated and the result is shown in FIG. 21.

FIG. 21 shows the deuterium NMR spectra of the heterochiral peptide complex of Example 1 and the homochiral peptide complex of Comparative Example 1 with a varying assembly state in 10% (v/v) D$_2$O at 298 K. All spectra were acquired using a 700-MHz NMR spectrometer.

As shown in FIG. 21, quadrupolar splitting of the deuterium peaks of the samples containing different peptides was measured in 10% (v/v) D$_2$O. The concentration of all the peptide complexes was set to 8 mg/mL.

The homochiral peptide complex of Comparative Example 1 (T-W$_6$) formed planar supramolecular structures (crystal), and the heterochiral peptide complex of Example 1 (T-(wW)$_3$) formed helical 1 D self-assembly as the self-assembled intermediate and formed crystal at the final stage of self-assembly. The self-assembled 1 D intermediate of the heterochiral peptide complex of Example 1 (T-(wW)$_3$) was aligned in much the same way as the nematic liquid crystal molecules do because it is an anisotropic self-assembled nanostructure. This result showed that the quadrupolar splitting of deuterium peak was most effective with the heterochiral peptide complex of Example 1 (T-(wW)$_3$) in the self-assembled 1 D intermediate state.

The 1D self-assembly of the heterochiral peptide complex of Example 1 (T-(wW)$_3$) yielded $^2$H quadrupolar splitting of 1.74 Hz at 8 mg/mL. The relatively small degree of $^2$H quadrupolar splitting is likely due to the low concentration of the heterochiral peptide complex of Example 1 (T-(wW)$_3$), which would limit the degree of alignment.

In contrast, quadrupole coupling was not observed at all for the homochiral peptide complex of Comparative Example 1 (crystal) and the heterochiral peptide complex of Example 1 (final state: crystal). The result is due to the difference in the degree of alignment depending on the supramolecular morphology and dimension. That is to say, it was confirmed that the heterochiral peptide complex of Example 1 (T-(wW)$_3$) can be used as a new alignment medium in which the degree of quadrupolar splitting changes depending on the extent of molecular self-assembly. An alignment medium for NMR measurement which shows the time-dependent quadrupolar splitting changes has not been reported yet. Conventionally, two different samples, i.e., the samples with or without the alignment medium, have been prepared for RDC measurement. However, only one sample will suffice to measure RDC with the heterochiral peptide complex of Example 1 (T-(wW)$_3$) of the present disclosure. In conclusion, the inventors of the present disclosure have developed a novel, slowly self-assembling heterochiral peptide complex and found previously unobserved self-assembled intermediates of the peptide. It has been shown that the heterochiral peptide complex is self-assembled in solution to form a self-assembled intermediate having strong anisotropy, and can be used to induce stable alignment of a sample for NMR measurement, especially for RDC analysis. In addition, the heterochiral peptide complex can be used as a drug carrier which delivers a hydrophobic drug by entrapping it in the hydrophobic region in the self-assembled structure. Besides, it may be used as a scaffold for 3D culture of tissues such as artificial skin, etc.

Experimental Example 7. Structural Analysis of Various Heterochiral (Ee) Peptide Complexes Various heterochiral peptide complexes were prepared and their structure was identified by AFM analysis.

Figure 26A:
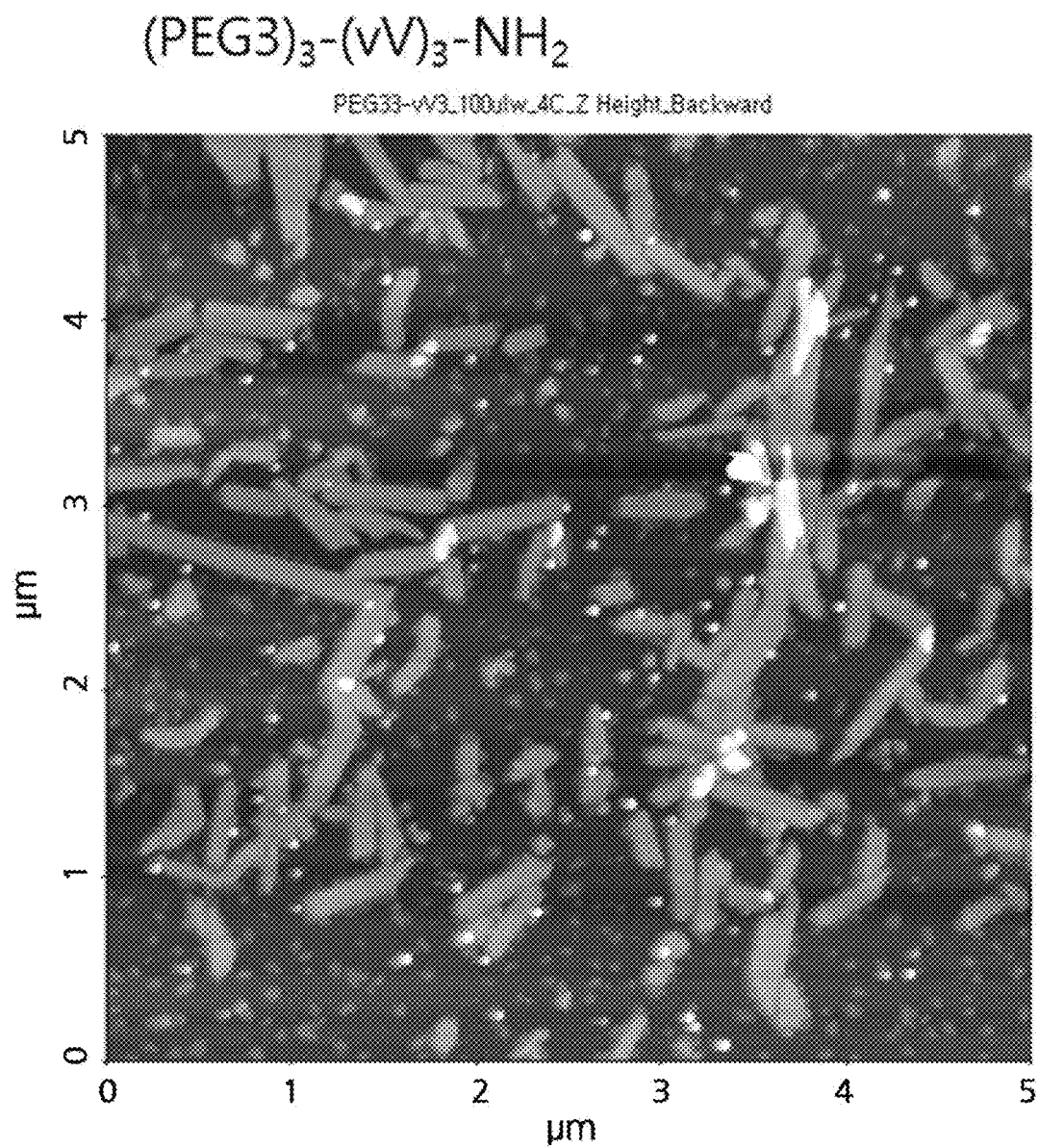
FIG. 26a shows the AFM images of a heterochiral peptide complex of Example 5 (T-(vV)$_3$)
Figure 26B:
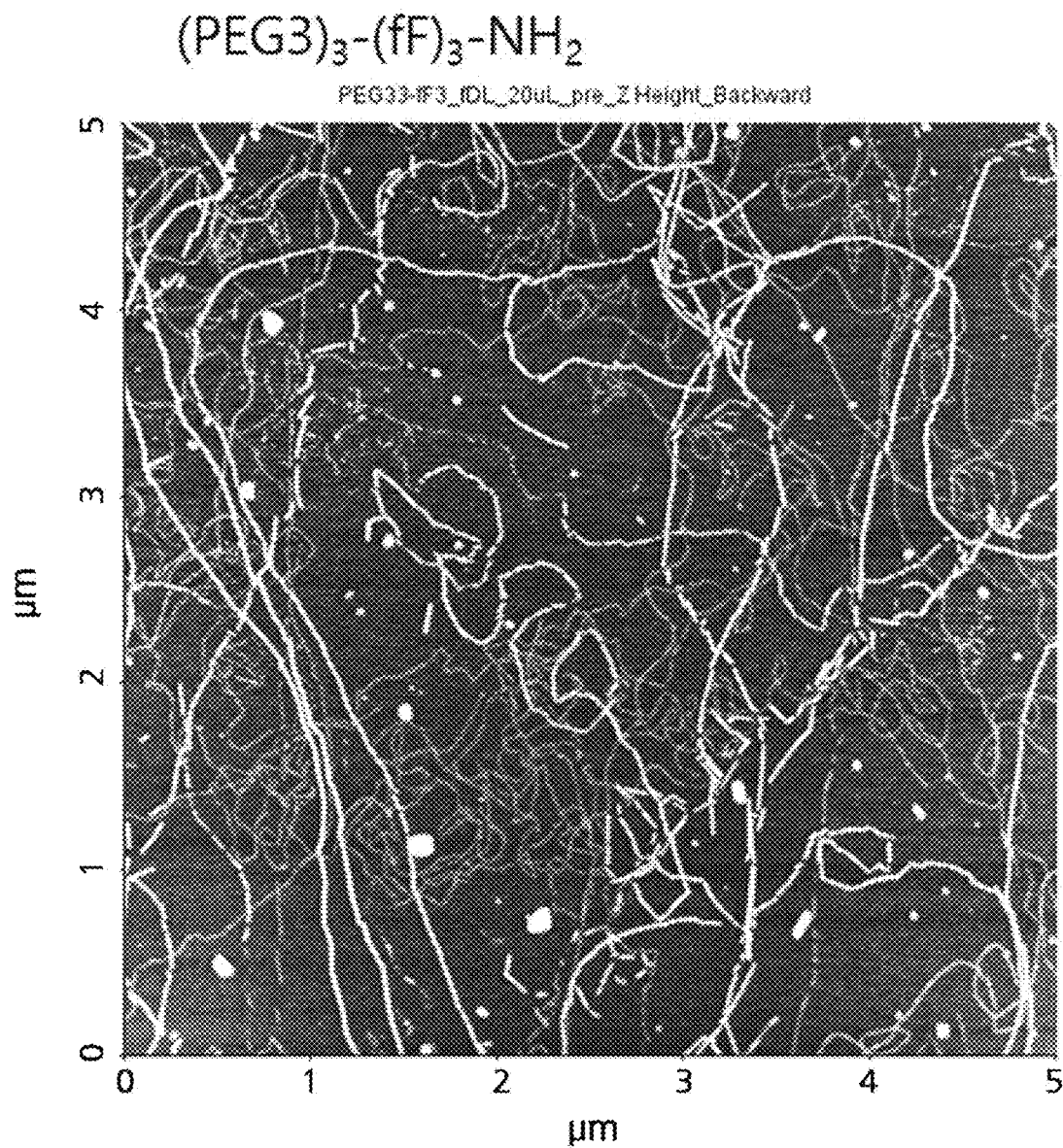
FIG. 26b shows the AFM images of a heterochiral peptide complex of Example 6 (T-(fF)₃)
Figure 26C:
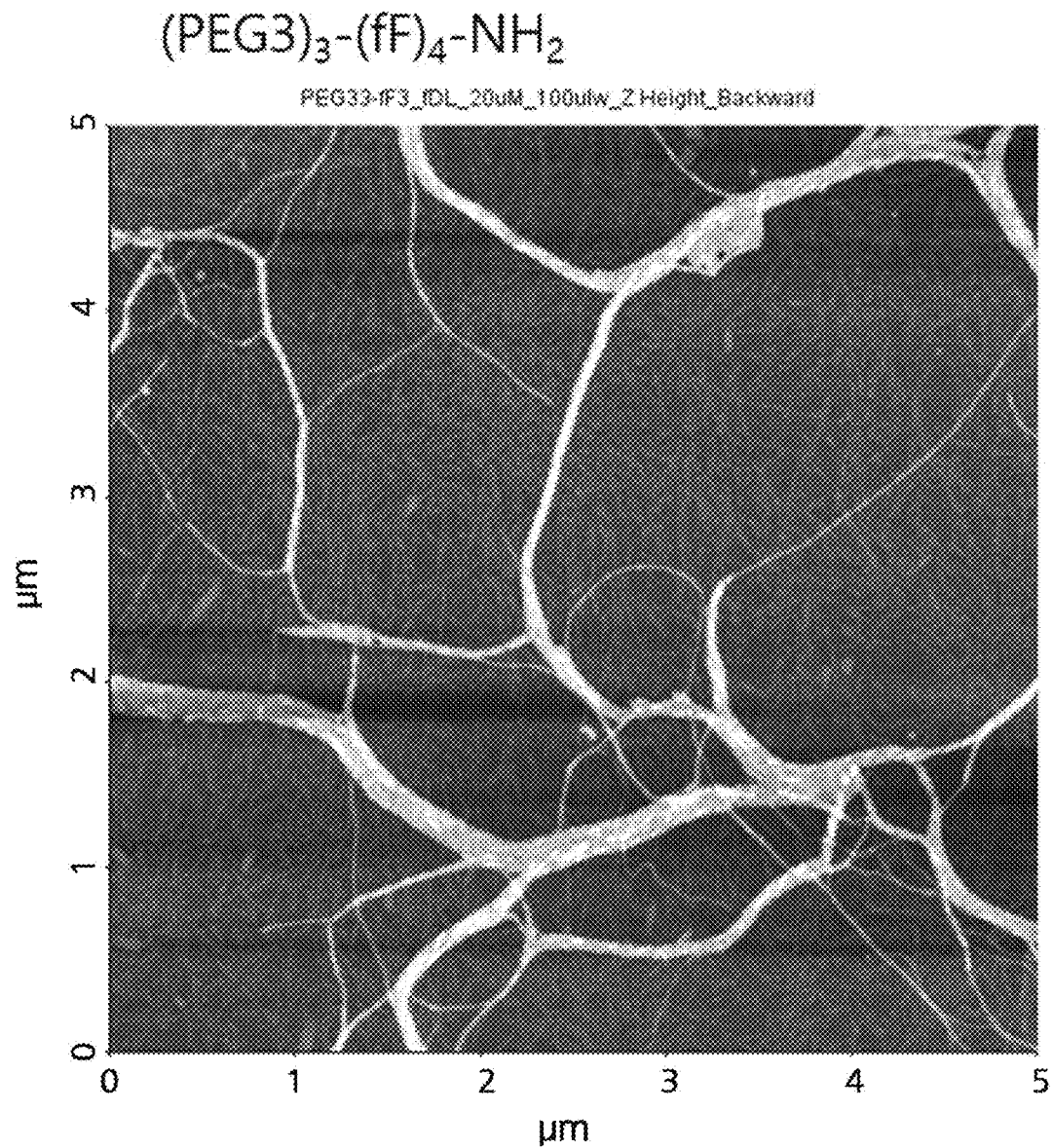
FIG. 26c shows the AFM images of a heterochiral peptide complex of Example 7 (T-(fF)₄).

FIG. 26a shows the AFM images of the heterochiral peptide complex of Example 5 (T-(vV)$_3$), FIG. 26b shows the AFM images of the heterochiral peptide complex of Example 6 (T-(fF)$_3$), and FIG. 26c shows the AFM images of the heterochiral peptide complex of Example 7 (T-(fF)$_4$).

Figure 27A:
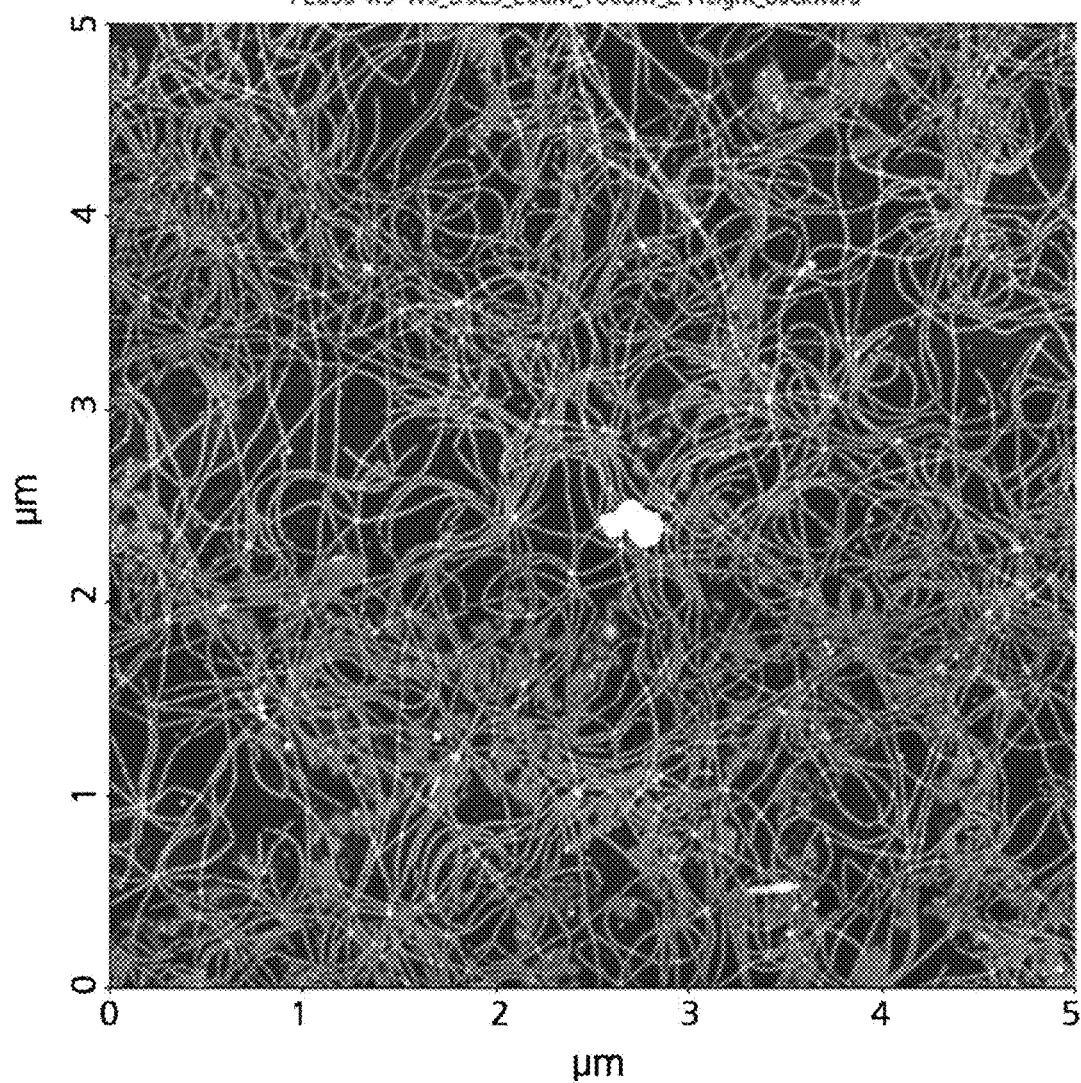
FIG. 27a shows the AFM images of a heterochiral peptide complex of Example 9 (T-w₃-W₃)
Figure 27B:
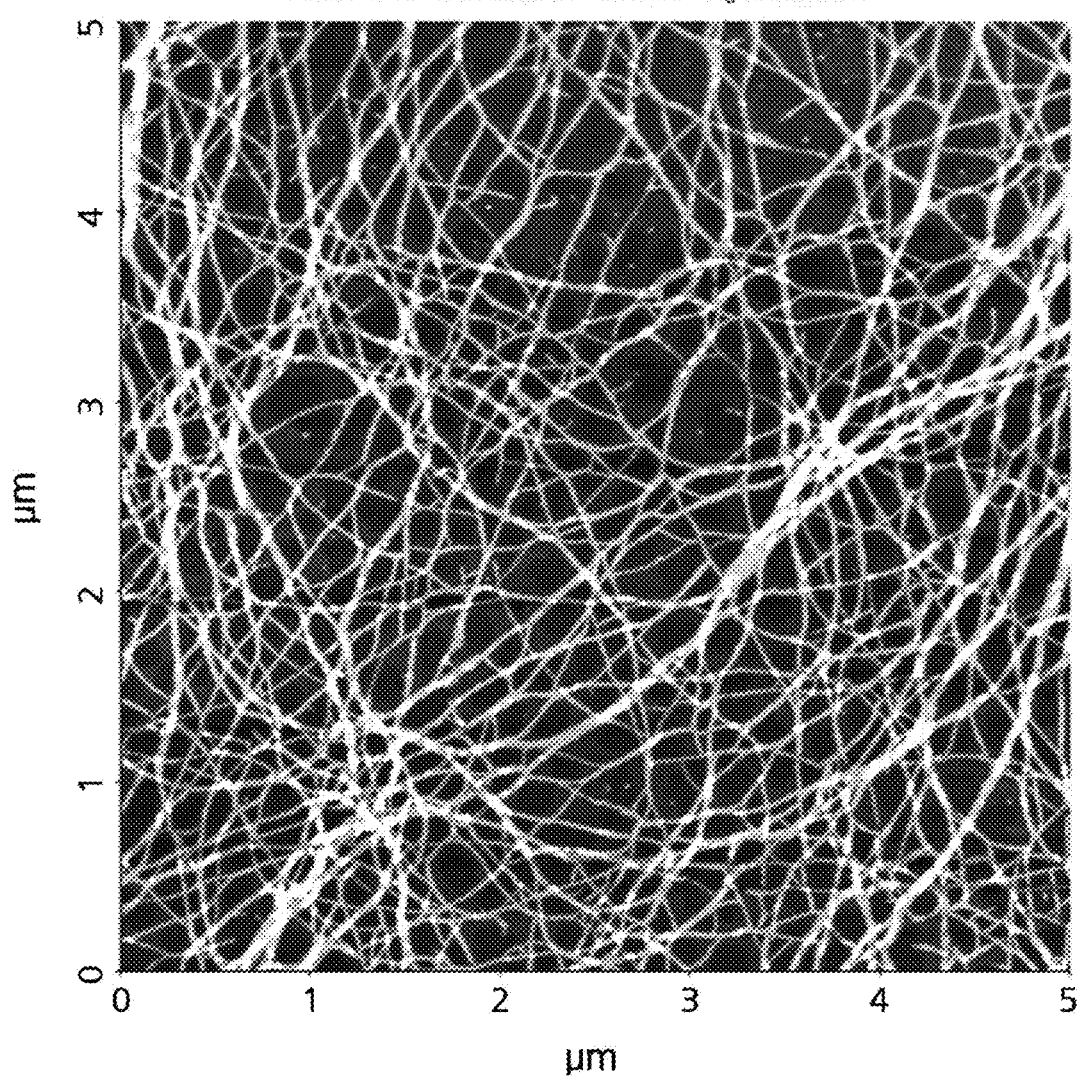
FIG. 27b shows the AFM images of a heterochiral peptide complex of Example 10 (T-(wW)₂-w₂)
Figure 27C:
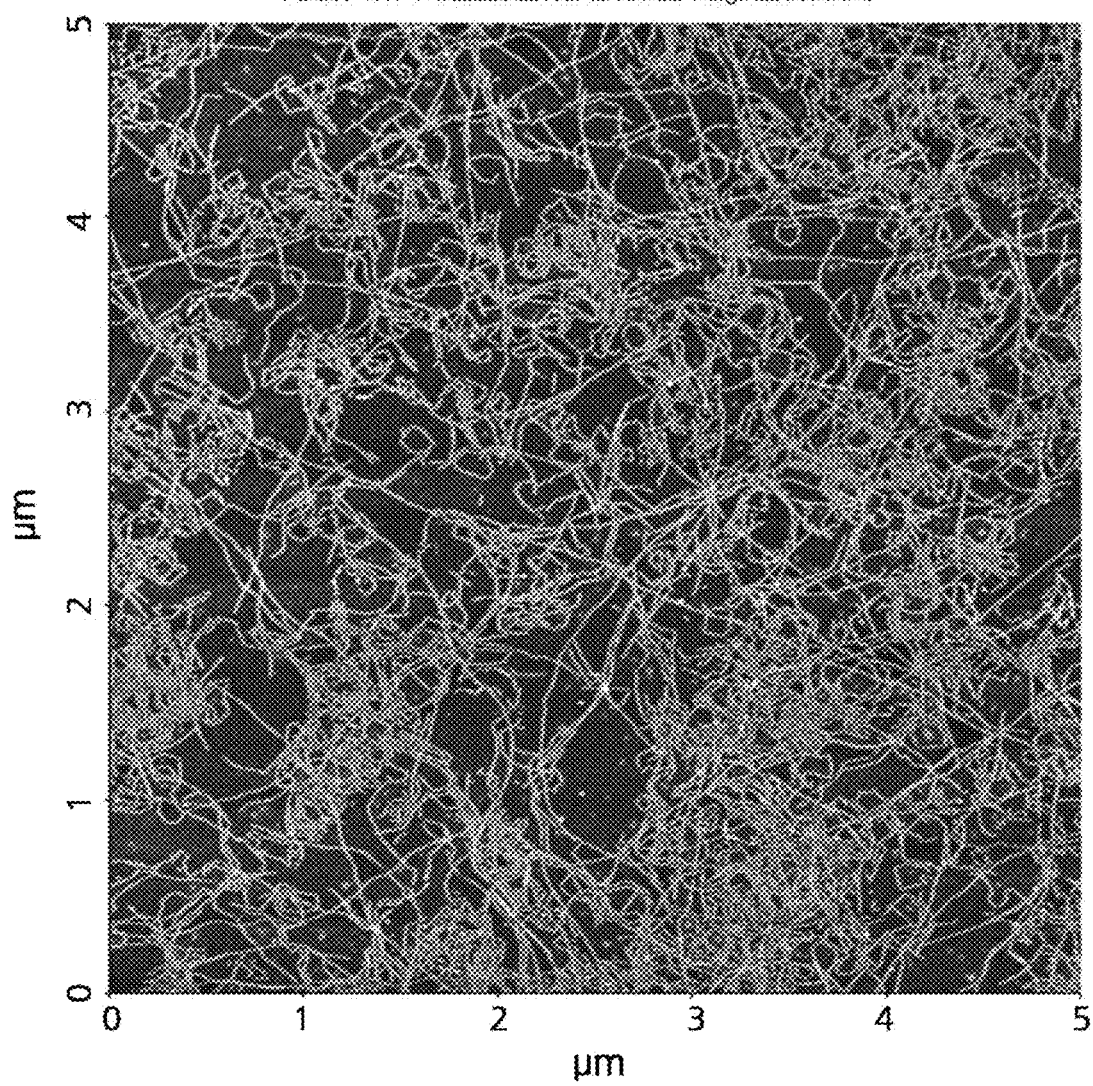
FIG. 27c shows the AFM images of a heterochiral peptide complex of Example 11 (T-W₂-(wW)₂)
Figure 27D:
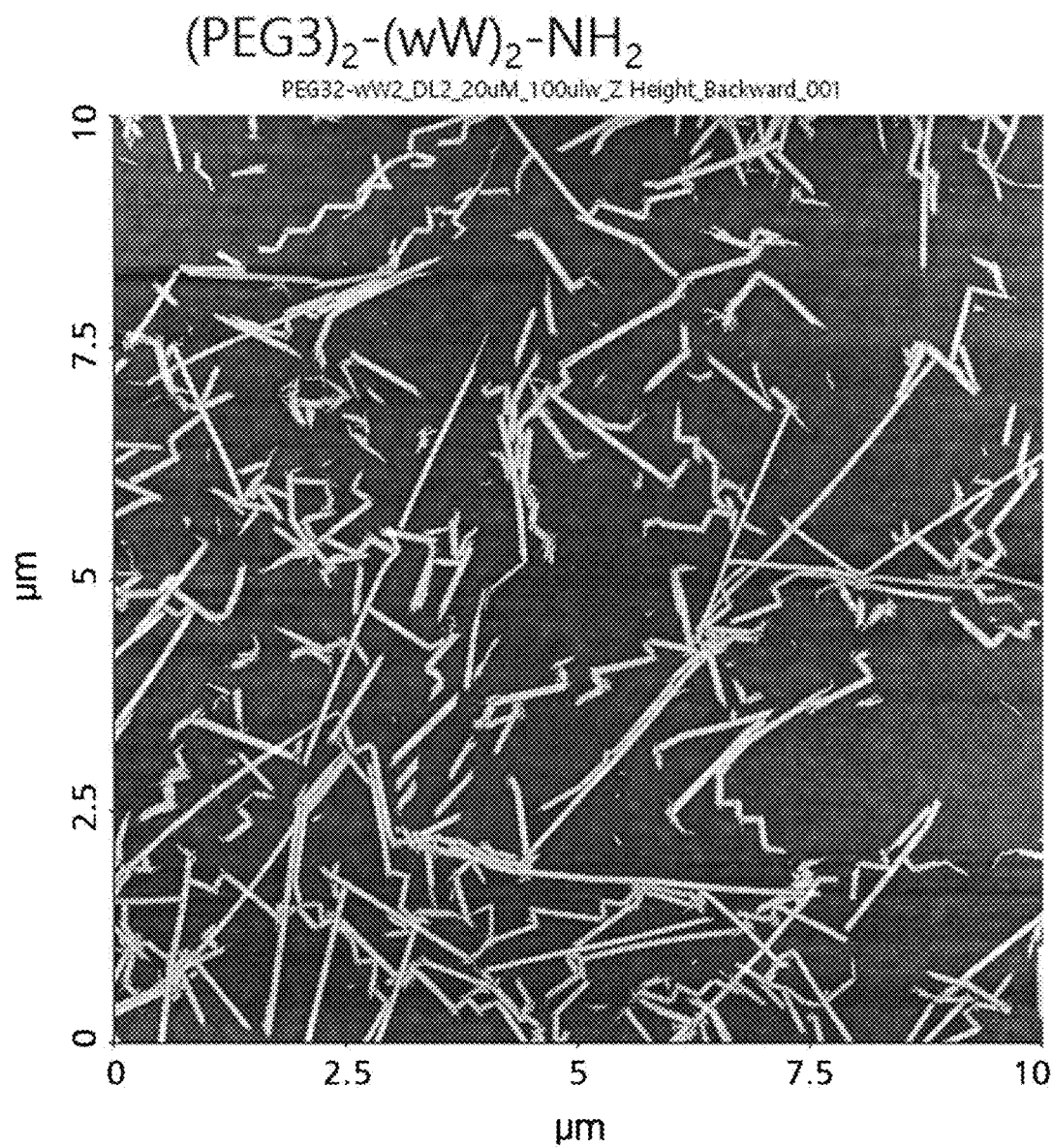
FIG. 27d shows the AFM images of a heterochiral peptide complex of Example 15 ((PEG3-PA)₂-(wW)₂).

FIG. 27a shows the AFM images of the heterochiral peptide complex of Example 9 (T-w$_3$-W$_3$), FIG. 27b shows the AFM images of the heterochiral peptide complex of Example 10 (T-(wW)$_2$-w$_2$), FIG. 27c shows the AFM images of the heterochiral peptide complex of Example 11 (T-W$_2$-(wW)$_2$), and FIG. 27d shows the AFM images of the heterochiral peptide complex of Example 15 ((PEG3-PA)$_2$-(wW)$_2$).

Figure 28A:
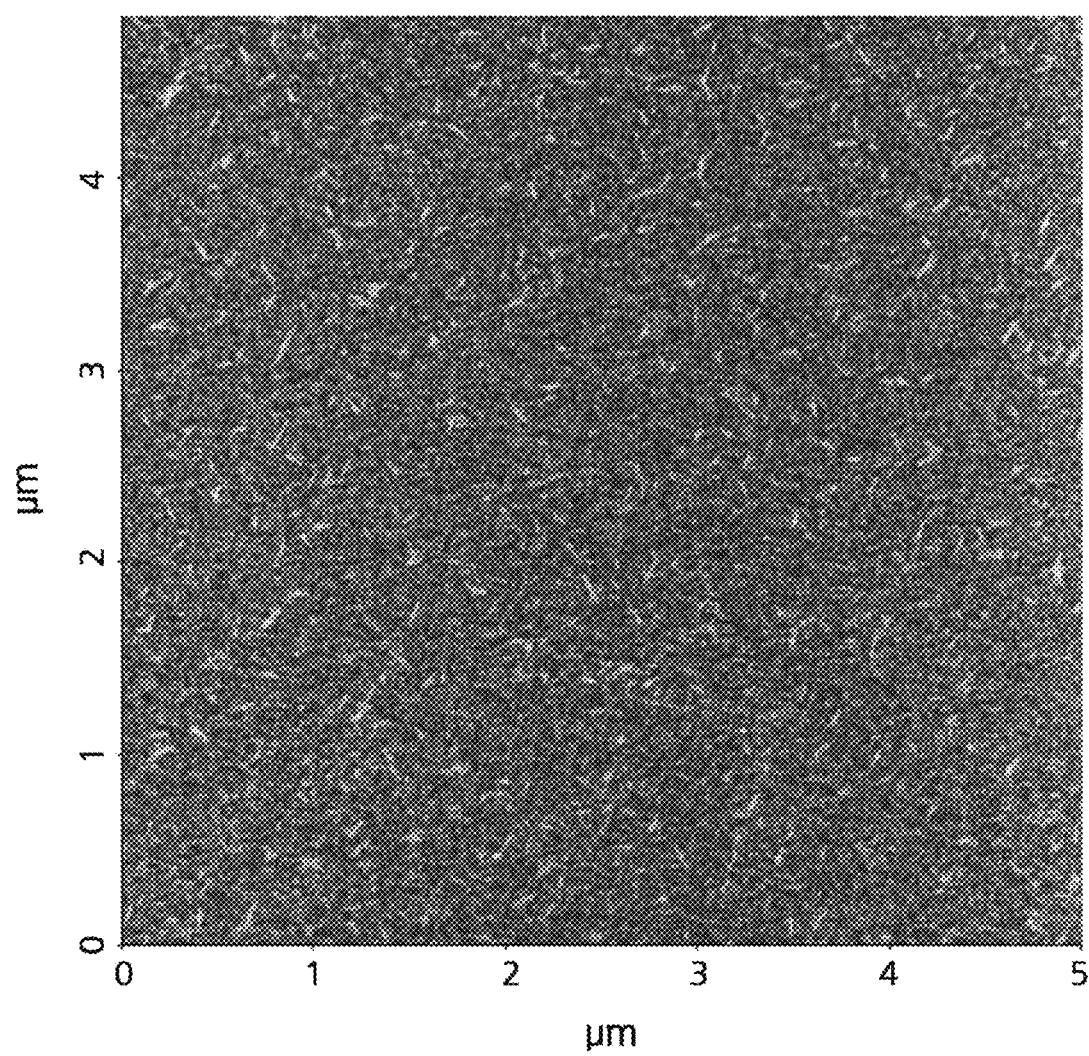
FIG. 28a shows the AFM images of a heterochiral peptide complex of Example 17 ((PEG10-PA)-V-(vV)₂)
Figure 28B:
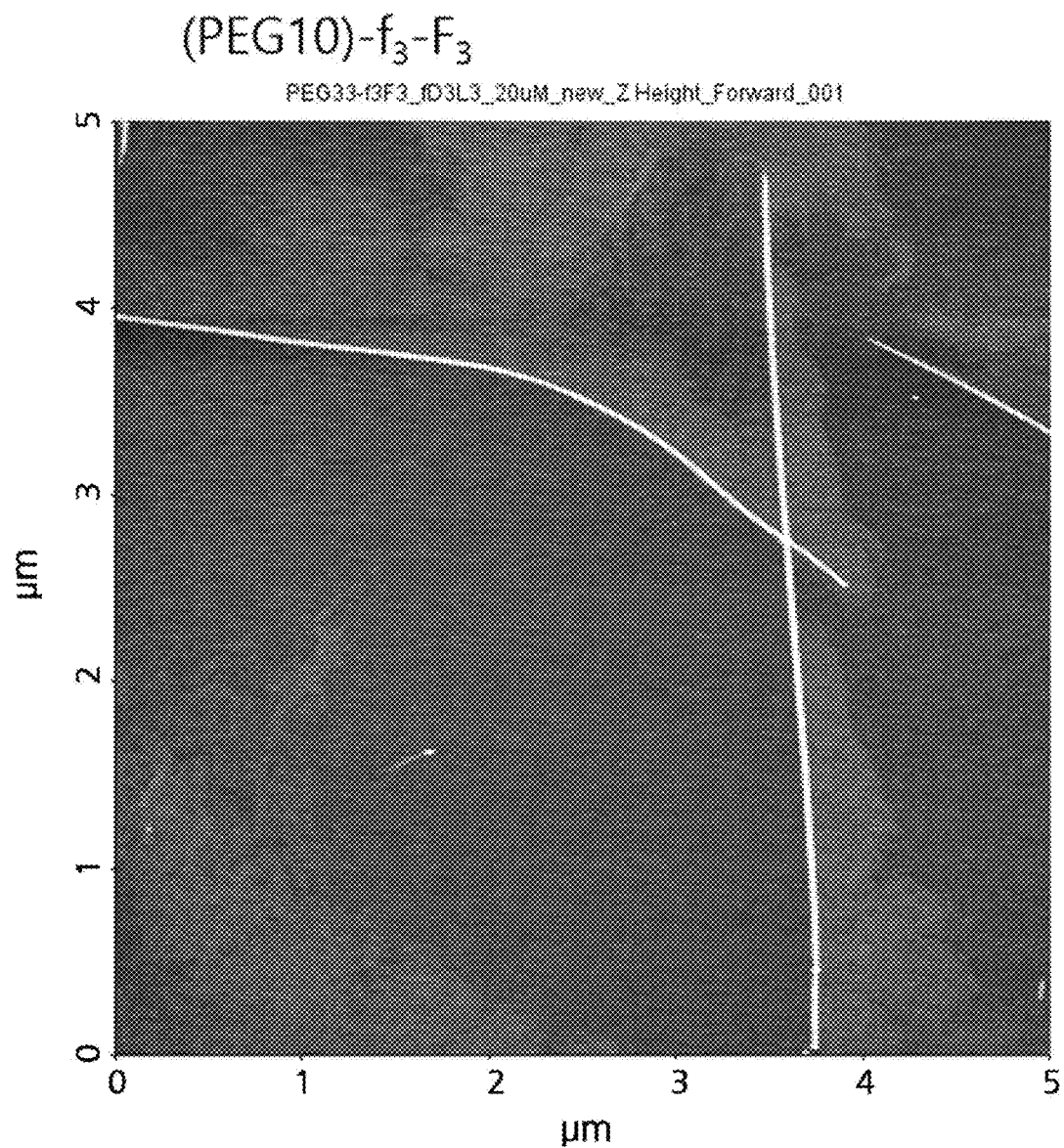
FIG. 28b shows the AFM images of a heterochiral peptide complex of Example 18 ((PEG10-PA)-f₃-F₃)
Figure 28C:
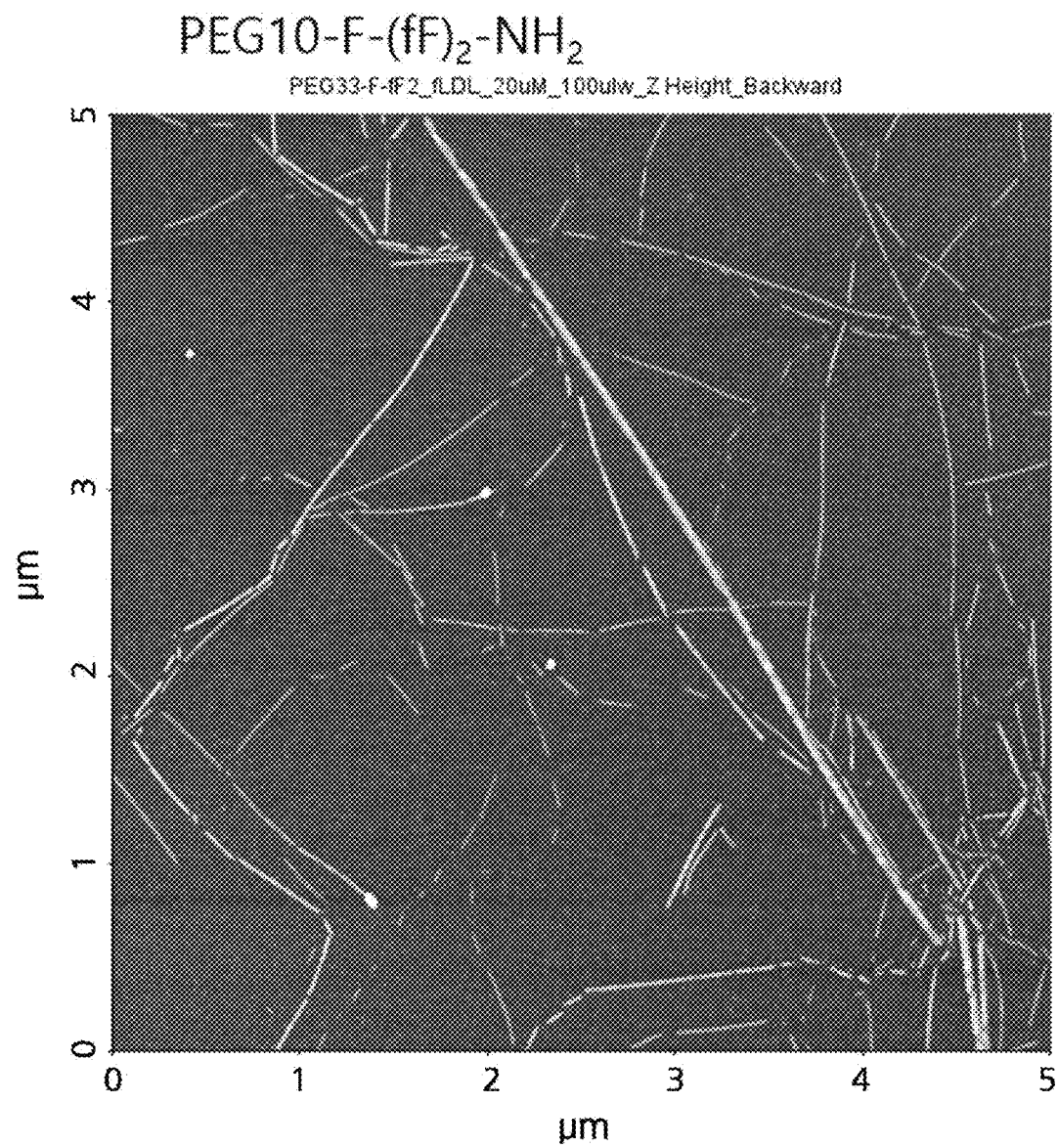
FIG. 28c shows the AFM images of a heterochiral peptide complex of Example 19 ((PEG10-PA)-F-(fF)₂).

FIG. 28a shows the AFM images of the heterochiral peptide complex of Example 17 ((PEG10-PA)-V-(vV)$_2$), FIG. 28b shows the AFM images of the heterochiral peptide complex of Example 18 ((PEG10-PA)-f$_3$-F$_3$), and FIG. 28c shows the AFM images of the heterochiral peptide complex of Example 19 ((PEG10-PA)-F-(fF)$_2$).

Referring to FIGS. 26-28, it was confirmed that the heterochiral peptide complexes of Examples 5-20 are self-assembled slowly similarly to the heterochiral peptide complexes of Examples 1-4 and form unique self-assembled intermediates.

Accordingly, the heterochiral peptide complexes of Examples 5-20 according to the present disclosure, in addition to the heterochiral peptide complexes of Examples 1-4, can be used to induce stable alignment of a sample for NMR measurement, especially for RDC analysis, since they are self-assembled slowly in solution and form self-assembled intermediates having strong anisotropy.

What is claimed is:

1. A method for analyzing an NMR spectrum of a biomolecule, comprising:
   (a) a step of mixing a peptide complex in a mixture solvent;
   (b) a step of adding a biomolecule to be measured in the mixture solution; and
   (c) a step of conducting NMR measurement for the mixture of the biomolecule and the peptide complex, wherein the peptide complex comprises a peptide represented by General Formula 1 or 2, comprising a heterochiral peptide; and a compound represented by Chemical Formula 1, covalently bound to N-terminal of the peptide:

   [General Formula 1]

   [General Formula 2]

wherein
   each of X1 and X2, which are identical to or different from each other, is independently an amino acid selected from D-Trp, D-Phe, D-Tyr, D-Val, D-Leu and D-Ile,
   each of Y1 and Y2, which are identical to or different from each other, is independently an amino acid selected from L-Trp, L-Phe, L-Tyr, L-Val, L-Leu and L-Ile, and
   each of a, f, e and j is independently an integer selected from 0 to 2, each of b, c, g and h is independently an integer selected from 1 to 5, each of d and i is independently an integer selected from 1 to 10,

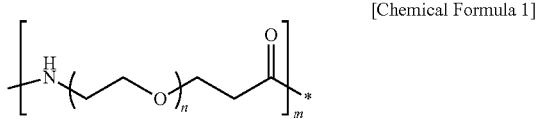
   [Chemical Formula 1]

wherein each of n and m is independently an integer selected from 1 to 12,
   wherein the peptide represented by General Formula 1 or General Formula II comprises at least five amino acid residues,
   wherein the amino acid in position 3, relative to the N-terminal of the peptide, is selected from the group consisting of D-Trp, D-Phe, D-Tyr, D-Val, D-Leu, D-Ile, L-Trp, L-Tyr, L-Val, L-Leu and L-Ile.

2. The method for analyzing an NMR spectrum of a biomolecule according to claim 1, wherein the NMR measurement is conducted by any one selected from a group consisting of $^1$H, $^1$H edit and 2D NMR.

3. The method for analyzing an NMR spectrum of a biomolecule according to claim 1, wherein the mixture solvent is a mixture of a deuterium solvent and a solvent.

4. The method for analyzing an NMR spectrum of a biomolecule according to claim 1, wherein in General Formulas 1 or 2,
   each of X1 and X2, which are identical to or different from each other, is independently an amino acid selected from D-Trp, D-Val and D-Phe, and
   each of Y1 and Y2, which are identical to or different from each other, is independently an amino acid selected from L-Trp, D-Val and L-Phe.

5. The method for analyzing an NMR spectrum of a biomolecule according to claim 1, wherein in General Formulas 1 or 2,
   X1 and X2 are identical to each other, and Y1 and Y2 are identical to each other.

6. The method for analyzing an NMR spectrum of a biomolecule according to claim 1, wherein in General Formulas 1 or 2,
   each of a, f, e and j is independently an integer selected from 0 to 2, each of b, c, g and h is independently an integer selected from 1 to 3, and each of d and i is independently an integer selected from 1 to 4.

7. A method for analyzing an NMR spectrum of a biomolecule, comprising:
   (a) a step of mixing a peptide complex in a mixture solvent;
   (b) a step of adding a biomolecule to be measured in the mixture solution; and
   (c) a step of conducting NMR measurement for the mixture of the biomolecule and the peptide complex, wherein the peptide complex comprises a peptide represented by General Formula 1 or 2, comprising a heterochiral peptide; and a compound represented by Chemical Formula 1, covalently bound to N-terminal of the peptide:

   [General Formula 1]

   [General Formula 2]

wherein
   each of X1 and X2, which are identical to or different from each other, is independently an amino acid selected from D-Trp, D-Phe, D-Tyr, D-Val, D-Leu and D-Ile,
   each of Y1 and Y2, which are identical to or different from each other, is independently an amino acid selected from L-Trp, L-Phe, L-Tyr, L-Val, L-Leu and L-Ile,
   each of a, f, e and j is independently an integer selected from 0 to 2, each of b, c, g and h is independently an integer selected from 1 to 5, each of d and i is independently an integer selected from 1 to 10,

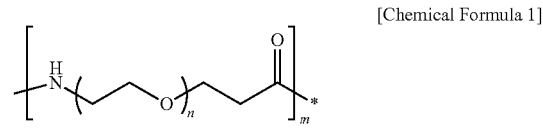
   [Chemical Formula 1]

wherein each of n and m is independently an integer selected from 1 to 12, and
   wherein the peptide is any one selected from the heterochiral peptides represented by SEQ ID NOS: 1 to 12:

(D)Trp-(L)Trp-(D)Trp-(L)Trp-(D)Trp-(L)Trp   [SEQ ID NO: 1]

(D)Val-(L)Val-(D)Val-(L)Val-(D)Val-(L)Val   [SEQ ID NO: 2]

(D)Phe-(L)Phe-(D)Phe-(L)Phe-(D)Phe-(L)Phe   [SEQ ID NO: 3]

| | |
|---|---|
| (L)Trp-(D)Trp-(L)Trp-(D)Trp-(L)Trp-(D)Trp | [SEQ ID NO: 4] |
| (L)Val-(D)Val-(L)Val-(D)Val-(L)Val-(D)Val | [SEQ ID NO: 5] |
| (L)Phe-(D)Phe-(L)Phe-(D)Phe-(L)Phe-(D)Phe | [SEQ ID NO: 6] |
| (L)Trp-(D)Trp-(L)Trp-(D)Trp-(L)Trp | [SEQ ID NO: 7] |
| (L)Val-(D)Val-(L)Val-(D)Val-(L)Val | [SEQ ID NO: 8] |
| (L)Phe-(D)Phe-(L)Phe-(D)Phe-(L)Phe | [SEQ ID NO: 9] |
| (D)Trp-(L)Trp-(D)Trp-(L)Trp-(D)Trp | [SEQ ID NO: 10] |
| (D)Val-(L)Val-(D)Val-(L)Val-(D)Val | [SEQ ID NO: 11] |
| (D)Phe-(L)Phe-(D)Phe-(L)Phe-(D)Phe. | [SEQ ID NO: 12] |

8. The method for analyzing an NMR spectrum of a biomolecule according to claim 1, wherein, in the peptide complex, the compound is represented by Chemical Formula 2:

[Chemical Formula 2]

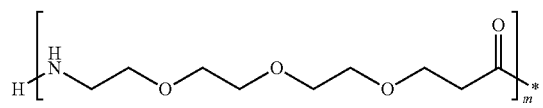

wherein m is an integer from 1 to 12.

9. The method for analyzing an NMR spectrum of a biomolecule according to claim 1, wherein the peptide complex is represented by any one of Chemical Formulas 3 to 6:

[Chemical Formula 3]

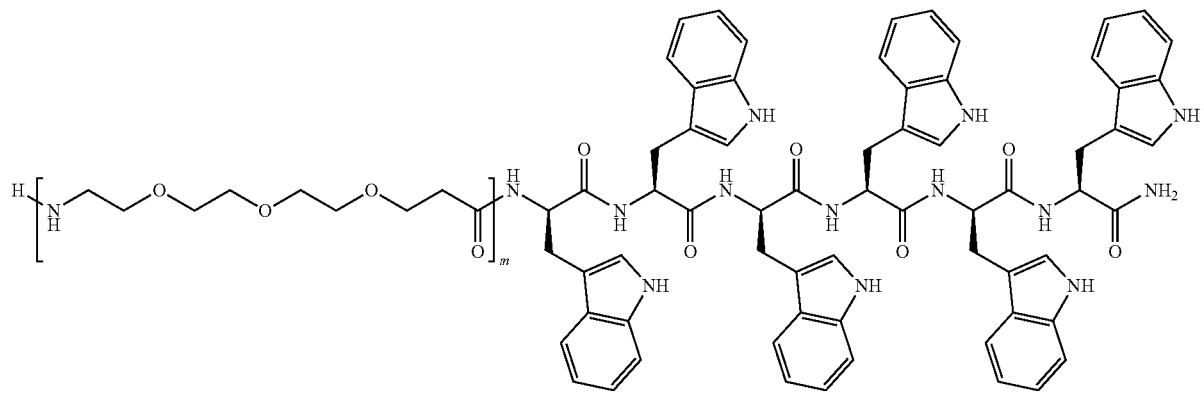

[Chemical Formula 4]

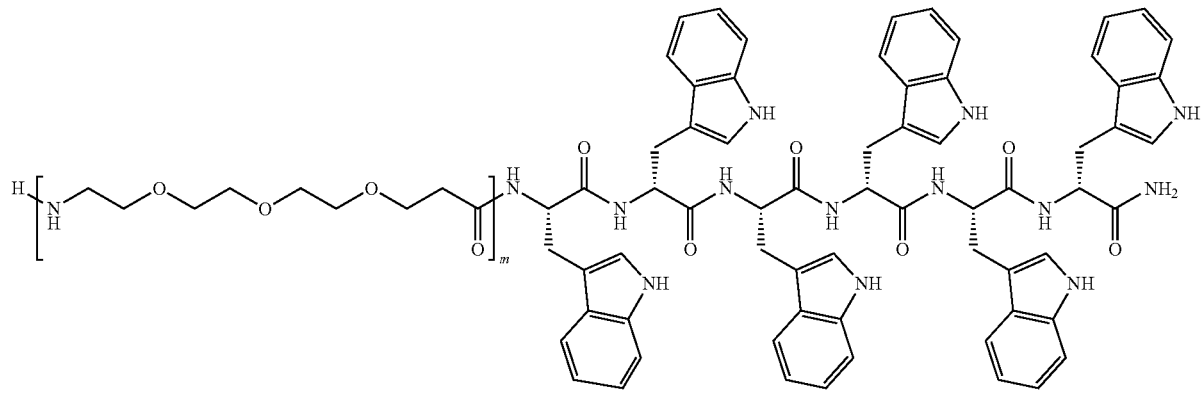

[Chemical Formula 5]
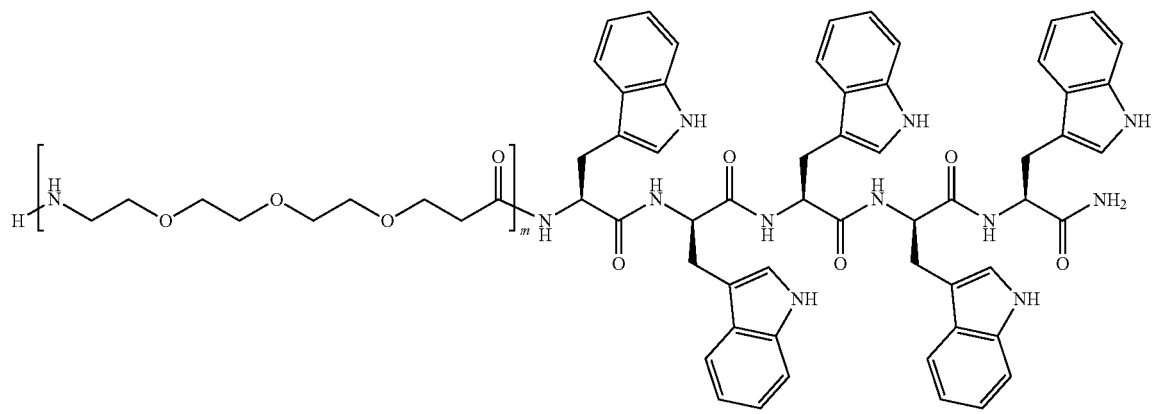
[Chemical Formula 6]
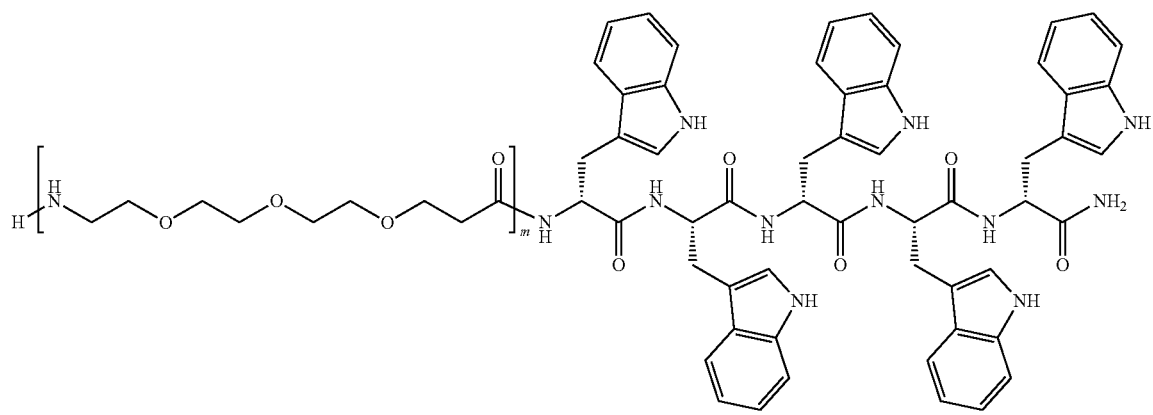
wherein m is an integer from 1 to 5.
* * * * *

SEQUENCE LISTING

```
<160> NUMBER OF SEQ ID NOS: 40

<210> SEQ ID NO 1
<211> LENGTH: 6
<212> TYPE: PRT
<213> ORGANISM: Artificial Sequence
<220> FEATURE:
<223> OTHER INFORMATION: The first, the third and the fifth tryptophan
      are D-tryptophan which is D-enantiomer.

<400> SEQUENCE: 1

Trp Trp Trp Trp Trp Trp
1               5

<210> SEQ ID NO 2
<211> LENGTH: 6
<212> TYPE: PRT
<213> ORGANISM: Artificial Sequence
<220> FEATURE:
<223> OTHER INFORMATION: The first, the third and the fifth valine are
      D-valine which is D-enantiomer.

<400> SEQUENCE: 2

Val Val Val Val Val Val
```

```
1               5

<210> SEQ ID NO 3
<211> LENGTH: 6
<212> TYPE: PRT
<213> ORGANISM: Artificial Sequence
<220> FEATURE:
<223> OTHER INFORMATION: The first, the third and the fifth
      phenylalanine are D-phenylalanine which is D-enantiomer.

<400> SEQUENCE: 3

Phe Phe Phe Phe Phe Phe
1               5

<210> SEQ ID NO 4
<211> LENGTH: 6
<212> TYPE: PRT
<213> ORGANISM: Artificial Sequence
<220> FEATURE:
<223> OTHER INFORMATION: The second, the fourth and the sixth tryptophan
      are D-tryptophan which is D-enantiomer.

<400> SEQUENCE: 4

Trp Trp Trp Trp Trp Trp
1               5

<210> SEQ ID NO 5
<211> LENGTH: 6
<212> TYPE: PRT
<213> ORGANISM: Artificial Sequence
<220> FEATURE:
<223> OTHER INFORMATION: The second valine, the  fourth valine, and the
      sixth valine are D-valine, D-enantiomer of valine.

<400> SEQUENCE: 5

Val Val Val Val Val Val
1               5

<210> SEQ ID NO 6
<211> LENGTH: 6
<212> TYPE: PRT
<213> ORGANISM: Artificial Sequence
<220> FEATURE:
<223> OTHER INFORMATION: The second, the fourth and the sixth
      phenylalanine are D-phenylalanine which is D-enantiomer.

<400> SEQUENCE: 6

Phe Phe Phe Phe Phe Phe
1               5

<210> SEQ ID NO 7
<211> LENGTH: 5
<212> TYPE: PRT
<213> ORGANISM: Artificial Sequence
<220> FEATURE:
<223> OTHER INFORMATION: The second and the fourth tryptophan are
      D-tryptophan which is D-enantiomer.

<400> SEQUENCE: 7

Trp Trp Trp Trp Trp
1               5

<210> SEQ ID NO 8
<211> LENGTH: 5
<212> TYPE: PRT
<213> ORGANISM: Artificial Sequence
<220> FEATURE:
<223> OTHER INFORMATION: The second and the fourth valine are D-valine
``` which is D-enantiomer.

<400> SEQUENCE: 8

Val Val Val Val Val
1               5

<210> SEQ ID NO 9
<211> LENGTH: 5
<212> TYPE: PRT
<213> ORGANISM: Artificial Sequence
<220> FEATURE:
<223> OTHER INFORMATION: The second and the fourth phenylalanine are
      D-phenylalanine which is D-enantiomer.

<400> SEQUENCE: 9

Phe Phe Phe Phe Phe
1               5

<210> SEQ ID NO 10
<211> LENGTH: 5
<212> TYPE: PRT
<213> ORGANISM: Artificial Sequence
<220> FEATURE:
<223> OTHER INFORMATION: The first, the third and the fifth tryptophan
      are D-tryptophan which is D-enantiomer.

<400> SEQUENCE: 10

Trp Trp Trp Trp Trp
1               5

<210> SEQ ID NO 11
<211> LENGTH: 5
<212> TYPE: PRT
<213> ORGANISM: Artificial Sequence
<220> FEATURE:
<223> OTHER INFORMATION: The first, the third and the fifth valine are
      D-valine which is D-enantiomer.

<400> SEQUENCE: 11

Val Val Val Val Val
1               5

<210> SEQ ID NO 12
<211> LENGTH: 5
<212> TYPE: PRT
<213> ORGANISM: Artificial Sequence
<220> FEATURE:
<223> OTHER INFORMATION: The first, the third and the fifth
      phenylalanine are D-phenylalanine which is D-enantiomer.

<400> SEQUENCE: 12

Phe Phe Phe Phe Phe
1               5

<210> SEQ ID NO 13
<211> LENGTH: 8
<212> TYPE: PRT
<213> ORGANISM: Artificial Sequence
<220> FEATURE:
<223> OTHER INFORMATION: The first, the third, the fifth and the seventh
      tryptophan are D-tryptophan which is D-enantiomer.

<400> SEQUENCE: 13

Trp Trp Trp Trp Trp Trp Trp Trp
1               5

<210> SEQ ID NO 14

```
<211> LENGTH: 8
<212> TYPE: PRT
<213> ORGANISM: Artificial Sequence
<220> FEATURE:
<223> OTHER INFORMATION: The first, the third, the fifth and the seventh
      valine are D-valine which is D-enantiomer.

<400> SEQUENCE: 14

Val Val Val Val Val Val Val Val
1               5

<210> SEQ ID NO 15
<211> LENGTH: 8
<212> TYPE: PRT
<213> ORGANISM: Artificial Sequence
<220> FEATURE:
<223> OTHER INFORMATION: The first, the third, the fifth and the seventh
      phenylalanine are D-phenylalanine which is D-enantiomer.

<400> SEQUENCE: 15

Phe Phe Phe Phe Phe Phe Phe Phe
1               5

<210> SEQ ID NO 16
<211> LENGTH: 6
<212> TYPE: PRT
<213> ORGANISM: Artificial Sequence
<220> FEATURE:
<223> OTHER INFORMATION: The first, the fourth and the fifth tryptophan
      are D-tryptophan which is D-enantiomer.

<400> SEQUENCE: 16

Trp Trp Trp Trp Trp Trp
1               5

<210> SEQ ID NO 17
<211> LENGTH: 6
<212> TYPE: PRT
<213> ORGANISM: Artificial Sequence
<220> FEATURE:
<223> OTHER INFORMATION: The first, the fourth and the fifth valine are
      D-valine which is D-enantiomer.

<400> SEQUENCE: 17

Val Val Val Val Val Val
1               5

<210> SEQ ID NO 18
<211> LENGTH: 6
<212> TYPE: PRT
<213> ORGANISM: Artificial Sequence
<220> FEATURE:
<223> OTHER INFORMATION: The first, the fourth and the fifth
      phenylalanine are D-phenylalanine which is D-enantiomer.

<400> SEQUENCE: 18

Phe Phe Phe Phe Phe Phe
1               5

<210> SEQ ID NO 19
<211> LENGTH: 6
<212> TYPE: PRT
<213> ORGANISM: Artificial Sequence
<220> FEATURE:
<223> OTHER INFORMATION: The first, the second and the third tryptophan
      are D-tryptophan which is D-enantiomer.

<400> SEQUENCE: 19
```

```
Trp Trp Trp Trp Trp Trp
1               5

<210> SEQ ID NO 20
<211> LENGTH: 6
<212> TYPE: PRT
<213> ORGANISM: Artificial Sequence
<220> FEATURE:
<223> OTHER INFORMATION: The first, the second and the third valine are
      D-valine which is D-enantiomer.

<400> SEQUENCE: 20

Val Val Val Val Val Val
1               5

<210> SEQ ID NO 21
<211> LENGTH: 6
<212> TYPE: PRT
<213> ORGANISM: Artificial Sequence
<220> FEATURE:
<223> OTHER INFORMATION: The first, the second and the third
      phenylalanine are D-phenylalanine which is D-enantiomer.

<400> SEQUENCE: 21

Phe Phe Phe Phe Phe Phe
1               5

<210> SEQ ID NO 22
<211> LENGTH: 6
<212> TYPE: PRT
<213> ORGANISM: Artificial Sequence
<220> FEATURE:
<223> OTHER INFORMATION: The first, the third, the fifth and the sixth
      tryptophan are D-tryptophan which is D-enantiomer.

<400> SEQUENCE: 22

Trp Trp Trp Trp Trp Trp
1               5

<210> SEQ ID NO 23
<211> LENGTH: 6
<212> TYPE: PRT
<213> ORGANISM: Artificial Sequence
<220> FEATURE:
<223> OTHER INFORMATION: The first, the third, the fifth and the sixth
      valine are D-valine which is D-enantiomer.

<400> SEQUENCE: 23

Val Val Val Val Val Val
1               5

<210> SEQ ID NO 24
<211> LENGTH: 6
<212> TYPE: PRT
<213> ORGANISM: Artificial Sequence
<220> FEATURE:
<223> OTHER INFORMATION: The first, the third, the fifth and the sixth
      phenylalanine are D-phenylalanine which is D-enantiomer.

<400> SEQUENCE: 24

Phe Phe Phe Phe Phe Phe
1               5

<210> SEQ ID NO 25
<211> LENGTH: 6
<212> TYPE: PRT
<213> ORGANISM: Artificial Sequence
<220> FEATURE:
```

```
<223> OTHER INFORMATION: the third and the fifth tryptophan are
      D-tryptophan which is D-enantiomer.

<400> SEQUENCE: 25

Trp Trp Trp Trp Trp Trp
1               5

<210> SEQ ID NO 26
<211> LENGTH: 6
<212> TYPE: PRT
<213> ORGANISM: Artificial Sequence
<220> FEATURE:
<223> OTHER INFORMATION: the third and the fifth valine are D-valine
      which is D-enantiomer.

<400> SEQUENCE: 26

Val Val Val Val Val Val
1               5

<210> SEQ ID NO 27
<211> LENGTH: 6
<212> TYPE: PRT
<213> ORGANISM: Artificial Sequence
<220> FEATURE:
<223> OTHER INFORMATION: the third and the fifth phenylalanine are
      D-phenylalanine which is D-enantiomer.

<400> SEQUENCE: 27

Phe Phe Phe Phe Phe Phe
1               5

<210> SEQ ID NO 28
<211> LENGTH: 7
<212> TYPE: PRT
<213> ORGANISM: Artificial Sequence
<220> FEATURE:
<223> OTHER INFORMATION: The second, the fourth and the sixth tryptophan
      are D-tryptophan which is D-enantiomer.

<400> SEQUENCE: 28

Trp Trp Trp Trp Trp Trp Trp
1               5

<210> SEQ ID NO 29
<211> LENGTH: 7
<212> TYPE: PRT
<213> ORGANISM: Artificial Sequence
<220> FEATURE:
<223> OTHER INFORMATION: The second, the fourth and the sixth valine are
      D-valine which is D-enantiomer.

<400> SEQUENCE: 29

Val Val Val Val Val Val Val
1               5

<210> SEQ ID NO 30
<211> LENGTH: 7
<212> TYPE: PRT
<213> ORGANISM: Artificial Sequence
<220> FEATURE:
<223> OTHER INFORMATION: The second, the fourth and the sixth
      phenylalanine are D-phenylalanine which is D-enantiomer.

<400> SEQUENCE: 30

Phe Phe Phe Phe Phe Phe Phe
1               5
```

```
<210> SEQ ID NO 31
<211> LENGTH: 4
<212> TYPE: PRT
<213> ORGANISM: Artificial Sequence
<220> FEATURE:
<223> OTHER INFORMATION: The first and the third tryptophan are
      D-tryptophan which is D-enantiomer.

<400> SEQUENCE: 31

Trp Trp Trp Trp
1

<210> SEQ ID NO 32
<211> LENGTH: 4
<212> TYPE: PRT
<213> ORGANISM: Artificial Sequence
<220> FEATURE:
<223> OTHER INFORMATION: The first and the third valine are D-valine
      which is D-enantiomer.

<400> SEQUENCE: 32

Val Val Val Val
1

<210> SEQ ID NO 33
<211> LENGTH: 4
<212> TYPE: PRT
<213> ORGANISM: Artificial Sequence
<220> FEATURE:
<223> OTHER INFORMATION: The first and the third phenylalanine are
      D-phenylalanine which is D-enantiomer.

<400> SEQUENCE: 33

Phe Phe Phe Phe
1

<210> SEQ ID NO 34
<211> LENGTH: 4
<212> TYPE: PRT
<213> ORGANISM: Artificial Sequence
<220> FEATURE:
<223> OTHER INFORMATION: The first and the second tryptophan are
      D-tryptophan which is D-enantiomer.

<400> SEQUENCE: 34

Trp Trp Trp Trp
1

<210> SEQ ID NO 35
<211> LENGTH: 4
<212> TYPE: PRT
<213> ORGANISM: Artificial Sequence
<220> FEATURE:
<223> OTHER INFORMATION: The first and the second valine are D-valine
      which is D-enantiomer.

<400> SEQUENCE: 35

Val Val Val Val
1

<210> SEQ ID NO 36
<211> LENGTH: 4
<212> TYPE: PRT
<213> ORGANISM: Artificial Sequence
<220> FEATURE:
<223> OTHER INFORMATION: The first and the second phenylalanine are
      D-phenylalanine which is D-enantiomer.

<400> SEQUENCE: 36
```

Phe Phe Phe Phe
1

<210> SEQ ID NO 37
<211> LENGTH: 6
<212> TYPE: PRT
<213> ORGANISM: Artificial Sequence
<220> FEATURE:
<223> OTHER INFORMATION: Artificial Sequence

<400> SEQUENCE: 37

Trp Trp Trp Trp Trp Trp
1               5

<210> SEQ ID NO 38
<211> LENGTH: 6
<212> TYPE: PRT
<213> ORGANISM: Artificial Sequence
<220> FEATURE:
<223> OTHER INFORMATION: all of tryptophan is D-tryptophan which is
      D-enantiomer.

<400> SEQUENCE: 38

Trp Trp Trp Trp Trp Trp
1               5

<210> SEQ ID NO 39
<211> LENGTH: 6
<212> TYPE: PRT
<213> ORGANISM: Artificial Sequence
<220> FEATURE:
<223> OTHER INFORMATION: Artificial Sequence

<400> SEQUENCE: 39

Val Val Val Val Val Val
1               5

<210> SEQ ID NO 40
<211> LENGTH: 6
<212> TYPE: PRT
<213> ORGANISM: Artificial Sequence
<220> FEATURE:
<223> OTHER INFORMATION: all of valine is D-valine which is
      D-enantiomer.

<400> SEQUENCE: 40

Val Val Val Val Val Val
1               5